United States Patent
Argyros et al.

(10) Patent No.: US 11,814,629 B2
(45) Date of Patent: Nov. 14, 2023

(54) YEAST EXPRESSING GLUCOAMYLASE WITH ENHANCED STARCH HYDROLYSIS

(71) Applicant: Lallemand Hungary Liquidity Management LLC, Budapest (HU)

(72) Inventors: Aaron Argyros, Lebanon, NH (US); Alexandra-Elena Panaitiu, Enfield, NH (US)

(73) Assignee: Lallemand Hungary Liquidity Management LLC, Budapest (HU)

(*) Notice: Subject to any disclaimer, the term of this patent is extended or adjusted under 35 U.S.C. 154(b) by 0 days.

(21) Appl. No.: 17/206,900

(22) Filed: Mar. 19, 2021

(65) Prior Publication Data

US 2021/0292776 A1    Sep. 23, 2021

Related U.S. Application Data

(60) Provisional application No. 62/991,846, filed on Mar. 19, 2020.

(51) Int. Cl.
| | | |
|---|---|---|
| *C12N 9/34* | (2006.01) | |
| *C12N 1/18* | (2006.01) | |
| *C12P 7/06* | (2006.01) | |
| *C07K 14/395* | (2006.01) | |
| *C12N 15/81* | (2006.01) | |
| *C07K 14/39* | (2006.01) | |
| *C12N 9/30* | (2006.01) | |
| *C12R 1/865* | (2006.01) | |

(52) U.S. Cl.
CPC .............. *C12N 15/81* (2013.01); *C07K 14/39* (2013.01); *C12N 1/185* (2021.05); *C12N 9/242* (2013.01); *C12R 2001/865* (2021.05); *C12Y 302/01001* (2013.01)

(58) Field of Classification Search
CPC .................. C12N 9/2428; C12N 1/185; C12Y 302/01003
See application file for complete search history.

(56) References Cited

FOREIGN PATENT DOCUMENTS

| | | |
|---|---|---|
| CN | 108949590 B | 12/2018 |
| WO | 2017/037614 A1 | 3/2017 |
| WO | 2018/027131 A1 | 2/2018 |
| WO | 2018/167670 A1 | 9/2018 |

OTHER PUBLICATIONS

Barrero et al., "An improved secretion signal enhances the secretion of model proteins from *Pichia pastoris*," *Microb Cell Fact* 17:161, 2018, 13 pages.

Xu et al., "Efficient hydrolysis of raw starch and ethanol fermentation: a novel raw starch-digesting glucoamylase from *Penicillium oxalicum*," *Biotechnol Biofuels* 9:216, 2016, 18 pages.

*Primary Examiner* — Maryam Monshipouri
(74) *Attorney, Agent, or Firm* — Seed IP Law Group LLP

(57) ABSTRACT

The present disclosure concerns recombinant yeast host cell for saccharification of a biomass. The recombinant yeast host cell has a genetic modification for expressing a heterologous polypeptide having glucoamylase activity (*Penicillum oxalicum* glucoamylase). In some embodiments, the heterologous polypeptide can comprise a signal sequence. The present disclosure also concerns a process for saccharification of a biomass using the recombinant yeast host cell as well as a process for fermenting the saccharified biomass into a fermentation product.

16 Claims, 9 Drawing Sheets

Specification includes a Sequence Listing.

YEAST EXPRESSING GLUCOAMYLASE WITH ENHANCED STARCH HYDROLYSIS

CROSS-REFERENCE TO RELATED APPLICATIONS AND DOCUMENTS

The present application claims priority from U.S. provisional application 62/991,846 filed on Mar. 19, 2020 and herewith incorporated in its entirety. The Sequence Listing associated with this application is provided in text format in lieu of a paper copy, and is hereby incorporated by reference into the specification. The name of the text file containing the Sequence Listing is 580127_428_SEQUENCE_LISTING.txt. The text file is 163 KB, was created on Mar. 18, 2021, and is being submitted electronically via EFS-Web.

TECHNOLOGICAL FIELD

The present disclosure relates to a robust recombinant yeast host cell expressing enzymes and acting as a source of enzyme activity for saccharification and fermentation.

BACKGROUND

*Saccharomyces cerevisiae* is the primary biocatalyst used in the commercial production of fuel ethanol. This organism is proficient in fermenting glucose to ethanol, often to concentrations greater than 20% v/v. However, *S. cerevisiae* lacks the ability to hydrolyze polysaccharides. Consequently, in addition to yeast, industrial ethanol production requires the exogenous addition of expensive enzymes to convert complex sugars to glucose. For example, in the United States, the primary source of fuel ethanol is corn starch. Regardless of the mashing process, corn starch fermentation by yeast requires the exogenous addition of both α-amylase and glucoamylase.

The fermentation processes employed in the corn ethanol industry can be broadly classified based on utilized substrate into liquefied corn mash and raw corn flour fermentations. In the mashing process, corn is both thermally and enzymatically liquefied prior to fermentation using α-amylase, which breaks down long chain starch polymers into smaller dextrins. The mash is then cooled and inoculated with *S. cerevisiae*. Concomitantly, the exogenous purified glucoamylase is added. Glucoamylases (GAs) break down the branched dextrin into glucose molecules that are utilizable by yeast. GAs primarily hydrolyze α-1,4-glycosidic linkages from non-reducing ends in starch chain (they are, hence, exo-acting enzymes), while α-amylases can also hydrolyze α-1,6-glycosidic linkages from the inner starch chains (and are, therefore, endo-acting enzymes). The availability of a robust, ethanol-tolerant yeast strain is required to ferment the hydrolyzed starch into the desired final product, ethanol.

Since fermentation involves a number of stressors, improved and/or more efficient yeast trains are needed with greater robustness.

BRIEF SUMMARY

The present disclosure provides recombinant yeast host cells which expresses starch digesting glucoamylases that can be used in saccharification and fermentation of a biomass. The recombinant yeast host cells of the present disclosure exhibit increased robustness. The present disclosure concerns recombinant yeast host cells expressing a heterologous starch digesting glucoamylase by introducing a heterologous nucleic acid molecule encoding for the glucoamylase enzyme as well as a signal sequence allowing the secretion of the glucoamylase.

According to a first aspect, the present disclosure provides a recombinant yeast host cell for saccharification and fermentation of a biomass. The recombinant yeast host cell has a heterologous nucleic acid molecule encoding a heterologous polypeptide having glucoamylase activity. The heterologous nucleic acid molecule comprises a first polynucleotide encoding the heterologous polypeptide having glucoamylase activity. The polypeptide having glucoamylase activity has the amino acid sequence of SEQ ID NO: 6, is a variant of the amino acid sequence of SEQ ID NO: 6 having glucoamlyase activity, or is a fragment of the amino acid sequence of SEQ ID NO: 6 having glucoamylase activity. In some embodiments, the recombinant yeast host cell exhibits higher robustness during a fermentation, when compared to a control recombinant yeast host cell lacking the heterologous nucleic acid molecule and comprising a control nucleic acid molecule encoding a further glucoamylase (which is different from the polypeptide having glucoamylase activity of SEQ ID NO: 6). In an embodiment, the first polynucleotide comprises the nucleic acid sequence of SEQ ID NO: 20 or a degenerate sequence encoding SEQ ID NO: 6. In an embodiment, the recombinant yeast host cell further comprises a second polynucleotide encoding a signal sequence. In such embodiment, the second polynucleotide is operatively associated with the first polynucleotide. In an embodiment, the signal sequence has the amino acid sequence of SEQ ID NO: 21, is a variant the amino acid sequence of SEQ ID NO: 21 having signal sequence activity or is a fragment of the amino acid sequence of SEQ ID NO: 21 having signal sequence activity. In a further embodiment, the heterologous polypeptide has the amino acid sequence of SEQ ID NO: 29, is a variant of the amino acid sequence of SEQ ID NO: 29 having glucoamylase activity, or is a fragment of the amino acid sequence of SEQ ID NO: 29 having glucoamylase activity. In an embodiment, the heterologous polypeptide having the amino acid sequence of SEQ ID NO: 29 (a variant thereof or a fragment thereof) has, once secreted, the amino acid sequence of SEQ ID NO: 6 (a variant thereof or a fragment thereof). In yet another embodiment, the second polynucleotide comprises the nucleic acid sequence of SEQ ID NO: 22 or a degenerate sequence coding SEQ ID NO: 21 and/or the nucleic acid sequence of SEQ ID NO: 30, 38 or a degenerate sequence encoding SEQ ID NO: 29. In another embodiment, the signal sequence has the amino acid sequence of SEQ ID NO: 28, is a variant the amino acid sequence of SEQ ID NO: 28 having signal sequence activity or is a fragment of the amino acid sequence of SEQ ID NO: 28 having signal sequence activity. In a further embodiment, the heterologous polypeptide has the amino acid sequence of SEQ ID NO: 5, is a variant of the amino acid sequence of SEQ ID NO: 5 having glucoamylase activity, or is a fragment of the amino acid sequence of SEQ ID NO: 5 having glucoamylase activity. In an embodiment, the heterologous polypeptide having the amino acid sequence of SEQ ID NO: 5 (a variant thereof or a fragment thereof) has, once secreted, the amino acid sequence of SEQ ID NO: 6 (a variant thereof or a fragment thereof). In yet another embodiment, the second polynucleotide comprises the nucleic acid sequence of SEQ ID NO: 37 or a degenerate sequence coding SEQ ID NO: 28 and/or the nucleic acid sequence of SEQ ID NO: 4 or a degenerate sequence coding for SEQ ID NO: 5. In yet another embodiment, the signal sequence has the amino acid sequence of SEQ ID NO: 25, is a variant the amino acid sequence of SEQ ID NO: 25 having signal sequence activity or is a fragment of the amino acid sequence of SEQ ID NO: 25 having signal sequence activity. In an embodiments, the heterologous polypeptide has the amino acid sequence of SEQ ID NO: 31, is a variant of the amino acid sequence of SEQ ID NO: 31 having glucoamylase activity, or is a fragment of the amino acid sequence of SEQ ID NO: 31 having glucoamylase activity. In an embodiment, the heterologous polypeptide having the amino acid sequence of SEQ ID NO: 31 (a variant thereof or a fragment thereof) has, once secreted, the amino acid sequence of SEQ ID NO: 6 (a variant thereof or a fragment thereof). In still a further embodiment, the second polynucleotide comprises the nucleic acid sequence of SEQ ID NO: 42 or a degenerate sequence coding SEQ ID: 25 and/or the nucleic acid sequence of SEQ ID NO: 56 or a degenerate sequence coding for SEQ ID NO: 31. In yet another embodiment, the signal sequence has the amino acid sequence of SEQ ID NO: 27, is a variant the amino acid sequence of SEQ ID NO: 27 having signal sequence activity or is a fragment of the amino acid sequence of SEQ ID NO: 27 having signal sequence activity. In an embodiments, the heterologous polypeptide has the amino acid sequence of SEQ ID NO: 43, is a variant of the amino acid sequence of SEQ ID NO: 43 having glucoamylase activity, or is a fragment of the amino acid sequence of SEQ ID NO: 43 having glucoamylase activity. In an embodiment, the heterologous polypeptide having the amino acid sequence of SEQ ID NO: 43 (a variant thereof or a fragment thereof) has, once secreted, the amino acid sequence of SEQ ID NO: 6 (a variant thereof or a fragment thereof). In yet another embodiment, the second polynucleotide comprise the nucleic acid sequence of SEQ ID NO: 55 or a degenerate sequence coding SEQ ID NO: 27 and/or the nucleic acid sequence of SEQ ID NO: 44 or a degenerate sequence coding for SEQ ID NO: 43. In yet another embodiment, the signal sequence has the amino acid sequence of SEQ ID NO: 47, is a variant the amino acid sequence of SEQ ID NO: 47 having signal sequence activity or is a fragment of the amino acid sequence of SEQ ID NO: 47 having signal sequence activity. In an embodiments, the heterologous polypeptide has the amino acid sequence of SEQ ID NO: 45, is a variant of the amino acid sequence of SEQ ID NO: 45 having glucoamylase activity, or is a fragment of the amino acid sequence of SEQ ID NO: 45 having glucoamylase activity. In an embodiment, the heterologous polypeptide having the amino acid sequence of SEQ ID NO: 45 (a variant thereof or a fragment thereof) has, once secreted, the amino acid sequence of SEQ ID NO: 6 (a variant thereof or a fragment thereof). In still a further embodiment, the second polynucleotide comprises the nucleic acid sequence of SEQ ID NO: 48 or a degenerate sequence coding for SEQ ID NO: 47 and/or the nucleic acid sequence of SEQ ID NO: 46 or a degenerate sequence coding for SEQ ID NO: 45. In yet another embodiment, the signal sequence has the amino acid sequence of SEQ ID NO: 24, is a variant the amino acid sequence of SEQ ID NO: 24 having signal sequence activity or is a fragment of the amino acid sequence of SEQ ID NO: 24 having signal sequence activity. In an embodiments, the heterologous polypeptide has the amino acid sequence of SEQ ID NO: 49, is a variant of the amino acid sequence of SEQ ID NO: 49 having glucoamylase activity, or is a fragment of the amino acid sequence of SEQ ID NO: 49 having glucoamylase activity. In an embodiment, the heterologous polypeptide having the amino acid sequence of SEQ ID NO: 49 (a variant thereof or a fragment thereof) has, once secreted, the amino acid sequence of SEQ ID NO: 6 (a variant thereof or a fragment thereof). In the second polynucleotide comprises the nucleic acid sequence of SEQ ID NO: 51 or a degenerate sequence encoding SEQ ID NO: 24 and/or the nucleic acid sequence of SEQ ID NO: 50 or a degenerate sequence coding for SEQ ID NO: 49. In an embodiment, the heterologous nucleic acid molecule further comprises a third polynucleotide comprising a heterologous promoter operatively associated with the first polynucleotide and the second polynucleotide allowing the expression of the heterologous polypeptide having glucoamylase activity. In an embodiment, the third polynucleotide comprises a tef2p, a adh1p and/or a qcr8p. In an embodiment, the third polynucleotide comprises a nucleic acid sequence of SEQ ID NO: 52, a variant of the nucleic acid sequence of SEQ ID NO: 52 having tef2p activity or a fragment of the nucleic acid sequence of SEQ ID NO: 52 having tep2p activity. In an embodiment, the third polynucleotide comprises a nucleic acid sequence of SEQ ID NO: 53, a variant of the nucleic acid sequence of SEQ ID NO: 53 having adh1p activity or a fragment of the nucleic acid sequence of SEQ ID NO: 53 having adh1p activity. In an embodiment, the third polynucleotide comprises a nucleic acid sequence of SEQ ID NO: 54, a variant of the nucleic acid sequence of SEQ ID NO: 54 having qcr8p activity or a fragment of the nucleic acid sequence of SEQ ID NO: 54 having qcr8p activity. In yet another embodiment, the heterologous polypeptide having glucoamylase activity is a secreted polypeptide. In yet a further embodiment, the heterologous polypeptide having glucoamylase activity is a membrane-associated polypeptide, such as, for example, a tethered polypeptide. In an embodiment, the recombinant yeast host cell is from the genus *Saccharomyces*, such as, for example, from the species *Saccharomyces cerevisiae*.

According to a second aspect, the present disclosure provides a composition comprising the recombinant yeast host cell described herein and starch.

According to a third aspect, the present disclosure provides a process for saccharification and fermentation of a biomass into a fermentation product, the process comprises contacting the biomass with the recombinant yeast host cell described herein or the composition described herein, under a condition that allows the conversion of at least a part of the biomass into the fermentation product. In an embodiment, the biomass is derived from or comprises corn, potato, cassava, rice, wheat, lignocellulosic material or buckwheat. In yet another embodiment, the biomass is derived from or comprises corn, for example, the biomass can comprise or is corn mash. In another example, the biomass comprises raw starch. In an embodiment, the fermentation product is ethanol. In yet a further embodiment, the fermentation is conducted in the presence of a stressor. In a specific embodiment, the stressor comprises low pH, such as, for example, a pH of 5.0 or lower or a pH of 4.0 or lower. In another embodiment, the stressor comprises an elevated temperature.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION

Figure 1:
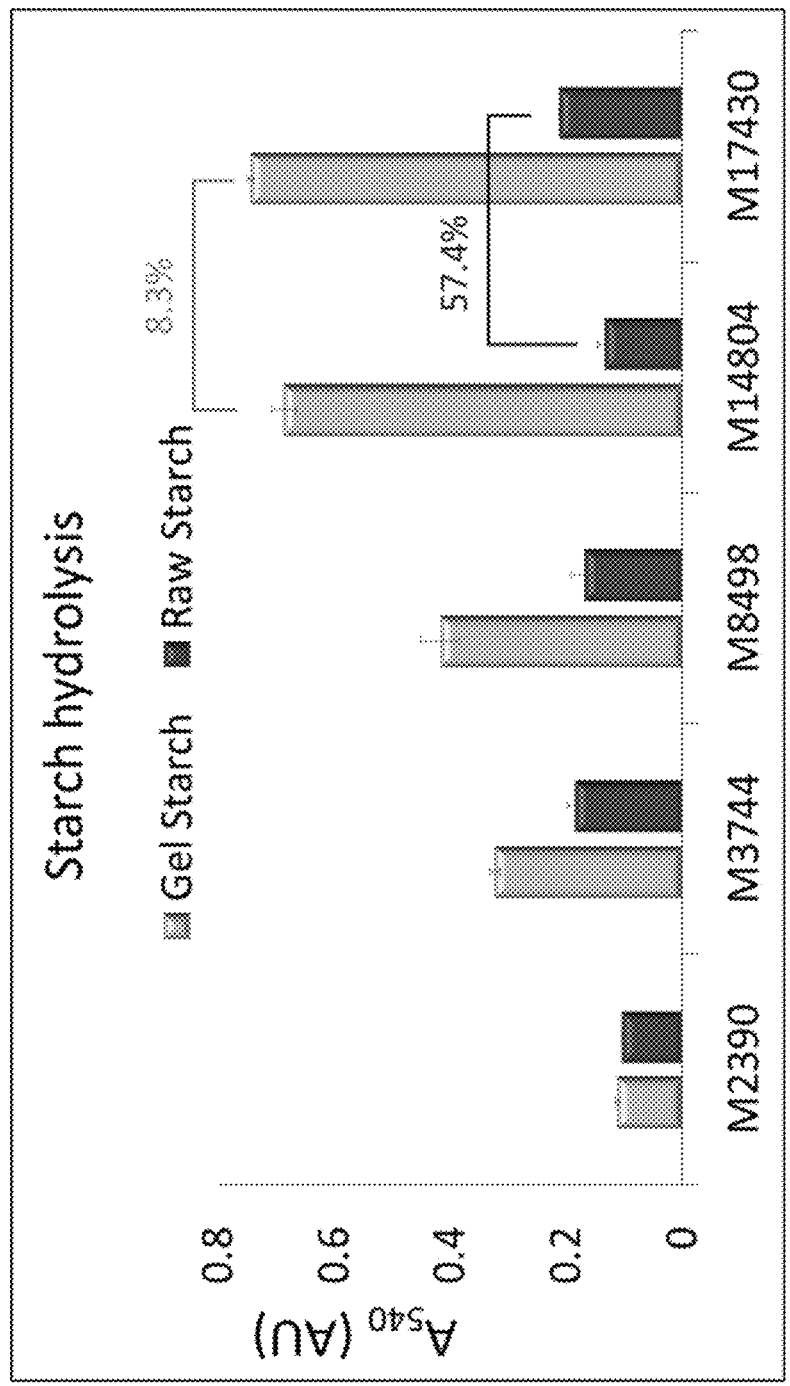
FIG. 1 illustrates starch hydrolysis activity of various yeast strains in gel (left bars) and raw (right bars) corn. Data is shown as absorbance at 540 nm in function of yeast strain or substrate used. Results are shown for strains M2390, M3744, M8498, M14804, and M17430. Data represent average absorbance readings of three replicates at 540 nm of 3,5-dinitrosalicylic acid (DNS). Error bars denote standard deviation of the mean.

The present disclosure provides recombinant yeast host cells that can be used under conditions of saccharification and fermentation of a biomass. The recombinant yeast host cells of the present disclosure express a heterologous glucoamylase from *Penicillum oxalicum*. In some embodiments, the heterologous glucoamylase is expressed with a heterologous signal sequence (which is cleaved upon the secretion of the heterologous glucoamylase). As it will be discussed in more detail below, a recombinant yeast host cell capable of expressing a heterologous glucoamylase from *Penicillum oxalicum* is capable of exhibiting activity towards raw starch. In some specific embodiments, the supernatant of an overnight culture of the recombinant yeast host cell of the present disclosure is capable of hydrolyzing raw corn starch when incubated for 20 hours in a solution of 50 mM sodium acetate, pH=5.0, at 35° C. As it will be further discussed in more detail below, a recombinant yeast host cell capable of expressing a heterologous glucoamylase from *Penicillum oxalicum* is capable producing ethanol in the presence of a stressor, such as for example, a low pH 5.0, 4.6, 4.2, 3.8 or 3.4). In some specific embodiments, when the recombinant yeast host cell of the present disclosure is used during a fermentation conducted in the presence of 33.5% total solids, 300 ppm urea, at pH 5.0 and at a temperature of 33° C. (1-20 hours) and of 31° C. (20-53 hours) is capable of producing, at the end of the fermentation at least 146.0, 146.8 or 146.9 g/L of ethanol. In some specific embodiments, when the recombinant yeast host cell of the present disclosure is used during a fermentation conducted in the presence of 33.5% total solids, 300 ppm urea, at pH 4.6 and at a temperature of 33° C. (1-20 hours) and of 31° C. (20-53 hours) is capable of producing, at the end of the fermentation at least 145.5 or 146.5 g/L of ethanol. In some specific embodiments, when the recombinant yeast host cell of the present disclosure is used during a fermentation conducted in the presence of 33.5% total solids, 300 ppm urea, at pH 4.2 and at a temperature of 33° C. (1-20 hours) and of 31° C. (20-53 hours) is capable of producing, at the end of the fermentation at least 144.7, 144.9 or 147.0 g/L of ethanol. In some specific embodiments, when the recombinant yeast host cell of the present disclosure is used during a fermentation conducted in the presence of 33.5% total solids, 300 ppm urea, at pH 3.8 and at a temperature of 33° C. (1-20 hours) and of 31° C. (20-53 hours) is capable of producing, at the end of the fermentation at least 143.2, 144.3 or 145.6 g/L of ethanol. In some specific embodiments, when the recombinant yeast host cell of the present disclosure is used during a fermentation conducted in the presence of 33.5% total solids, 300 ppm urea, at pH 3.4 and at a temperature of 33° C. (1-20 hours) and of 31° C. (20-53 hours) is capable of producing, at the end of the fermentation at least 133.4 or 140.8 g/L of ethanol.

In some additional embodiments, the recombinant yeast host cell of the present disclosure exhibits higher robustness during fermentation than a control recombinant yeast host cell capable of expressing a different heterologous glucoamylase (which is not a heterologous glucoamylase from *Penicillum oxalicum*, which can be, in some specific embodiments, a heterologous glucoamylase from or derived from *Saccharomycopsis fibuligera* which can, in some embodiments, have the amino acid sequence of SEQ ID NO: 1, 2 or 3). The recombinant yeast host cells of the present disclosure exhibit robustness during fermentation, especially in the presence of a stressor. In the context of the present disclosure, the term "robustness" refers to the recombinant yeast host cell's ability to tolerate or to lack sensibility to perturbations associated with a stress, such as, for example, an increase in fermentation temperature and/or a decrease in fermentation pH. In the context of the present disclosure, robustness can be determined by measuring the cellular growth, the cellular growth rate, the cellular growth curve and/or the fermentation performance (including but limited to fermentation yield). When exposed to a stressor, the growth and fermentation performances of a more robust recombinant yeast strain will be less affected (and in some embodiments not affected) than the growth of a less robust strain. For example, when exposed to a stressor, the fermentation performance, the cellular growth, the cellular growth rate and/or the cellular growth curve of a more robust strain will less restrained (or, in some embodiments, not restrained) when compared to the fermentation yield, the cellular growth, the cellular growth rate and/or the cellular growth curve of a less robust strain exposed to the same stressor. The recombinant yeast host cells of the present disclosure are thus capable of converting a biomass into a fermentation product in the presence of a stressor (such as, for example, an elevated temperature and/or a low pH). The robustness of the recombinant yeast host cell of the present disclosure is increased with respect to a control recombinant yeast host cell lacking the heterologous nucleotide molecule. In some embodiments, the control recombinant yeast host cell includes a control heterologous nucleotide molecule encoding a heterologous glucoamylase which is not the *Penicillium oxalicum*'s glucoamylase.

Recombinant Yeast Host Cell

The heterologous polypeptides having glucoamylase activity are expressed in a recombinant yeast host cell. As such, the recombinant yeast host cell of the present disclosure thus includes at least one genetic modification. In the context of the present disclosure, when recombinant yeast cell is qualified as "having a genetic modification" or as being "genetically engineered", it is understood to mean that it has been manipulated to either add at least one or more heterologous or exogenous nucleic acid residue and/or remove at least one endogenous (or native) nucleic acid residue. The genetic manipulations did not occur in nature and are the results of in vitro manipulations of the recombinant host cell. When the genetic modification is the addition of a heterologous nucleic acid molecule, such addition can be made once or multiple times at the same or different integration sites. When the genetic modification is the modification of an endogenous nucleic acid molecule, it can be made in one or both copies of the targeted gene. In a specific embodiment, the recombinant yeast host cell having the genetic modification has a heterologous nucleic acid molecule encoding a heterologous polypeptide having glucoamylase activity.

When expressed in a recombinant yeast host cell, the heterologous polypeptide (having glucoamylase activity, e.g. a glucoamylase) described herein are encoded on one or more heterologous nucleic acid molecule. In some embodiments, the heterologous polypeptide described herein are encoded on one heterologous nucleic acid molecule (e.g., one copy), two heterologous nucleic acid molecules or copies, three heterologous nucleic acid molecules or copies, four heterologous nucleic acid molecules or copies, five heterologous nucleic acid molecules or copies, six heterologous nucleic acid molecules or copies, seven heterologous nucleic acid molecules or copies, or eight or more heterologous nucleic acid molecules or copies. The term "heterologous" when used in reference to a nucleic acid molecule (such as a promoter or a coding sequence) refers to a nucleic acid molecule that is not natively found in the recombinant yeast host cell. "Heterologous" also includes a native coding region, or portion thereof, that was removed from the organism (which can, in some embodiments, be a source organism) and subsequently reintroduced into the organism in a form that is different from the corresponding native gene, e.g., not in its natural location in the organism's genome. The heterologous nucleic acid molecule is purposively introduced into the recombinant yeast host cell. The term "heterologous" as used herein also refers to an element (nucleic acid or polypeptide) that is derived from a source other than the endogenous source. Thus, for example, a heterologous element could be derived from a different strain of host cell, or from an organism of a different taxonomic group (e.g., different kingdom, phylum, class, order, family genus, or species, or any subgroup within one of these classifications).

The heterologous nucleic acid molecule(s) present in the recombinant host cell can be integrated in the host cell's genome. The term "integrated" as used herein refers to genetic elements that are placed, through molecular biology techniques, into the genome of the host cell. For example, genetic elements can be placed into one or more chromosomes of the host cell as opposed to in a vector such as a plasmid carried by the host cell. Methods for integrating genetic elements into the chromosome of a host cell are well known in the art and include homologous recombination. The heterologous nucleic acid molecule(s) can be present in one or more copies in the yeast host cell's chromosome. Alternatively, the heterologous nucleic acid molecule can be independently replicating from the yeast's chromosome. In such embodiments, the nucleic acid molecule can be stable and self-replicating.

In the context of the present disclosure, the recombinant yeast host cell can be, for example, from the genus *Saccharomyces, Kluyveromyces, Arxula, Debaryomyces, Candida, Pichia, Phaffia, Schizosaccharomyces, Hansenula, Kloeckera, Schwanniomyces* or *Yarrowia*. Suitable yeast species can include, for example, *Saccharomyces cerevisiae, Saccharomyces bulderi, Saccharomyces barnetti, Saccharomyces exiguus, Saccharomyces uvarum, Saccharomyces diastaticus, Kluyveromyces lactis, Kluyveromyces marxianus* or *Kluyveromyces fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In some embodiments, the host cell can be an oleaginous yeast cell. For example, the oleaginous yeast host cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiments, the host cell can be an oleaginous microalgae host cell (e.g., for example, from the genus Thraustochytrium or Schizochytrium). In an embodiment, the recombinant yeast host cell is from the genus *Saccharomyces* and, in some additional embodiments, from the species *Saccharomyces cerevisiae*.

In some embodiments, the heterologous nucleic acid molecules introduced into the recombinant host cells are codon-optimized with respect to the intended recipient recombinant host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized heterologous nucleic acid molecule described herein corresponds to between about 0.8 and 1.0, between about 0.8 and 0.9, or about 1.0.

The heterologous nucleic acid molecules of the present disclosure can comprise a coding region for the heterologous polypeptide. A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

The heterologous nucleic acid molecules described herein can comprise transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

The heterologous nucleic acid molecule can be introduced in the host cell using a vector. A "vector," e.g., a "plasmid", "cosmid" or "artificial chromosome" (such as, for example, a yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Heterologous Polypeptides

The heterologous nucleic acid molecules of the present disclosure include a first polynucleotide encoding the heterologous polypeptide having glucoamylase activity. In some embodiments, the recombinant yeast host cell is obtained by introducing one or more heterologous nucleic acid molecule encoding the heterologous polypeptide in the recombinant yeast host cell. In some embodiments, the genetic modification(s) in the recombinant yeast host cell of the present disclosure comprise or consist essentially of or consist of expressing a heterologous polypeptide having starch digesting glucoamylase activity. In the context of the present disclosure, the expression "the genetic modification in the recombinant yeast host consist essentially of a genetic modification for expressing a heterologous polypeptide having starch digesting glucoamylase activity" refers to the fact that the recombinant yeast host cell only includes this genetic modification to modulate the expression of a polypeptide having starch digesting glucoamylase activity levels but can nevertheless include other genetic modifications which are unrelated to the expression of a glucoamylase (native or heterologous).

As indicated above, the heterologous polypeptide is a polypeptide having starch digesting glucoamylase activity. As used herein, a polypeptide having starch digesting glucoamylase activity refers to polypeptides having the ability to hydrolyze starch (which can be raw or have been heat-treated) directly to glucose. In some alternative embodiments, the heterologous polypeptide having glucoamylase activity can be derived from a fungus, for example, from the genus *Penicillium* sp. and, in some instances, from the species *Penicillium oxalicum*. In specific embodiments, the polypeptide having starch digesting glucoamylase activity can have raw starch digesting glucoamylase activity.

Polypeptides having starch digesting glucoamylase activity may comprise a catalytic domain and a starch binding domain. The catalytic domain and the starch binding domain may be connected by a connecting loop or linker. For example, the glucoamylase having the amino acid sequence of SEQ ID NO: 5 includes a catalytic domain (SEQ ID NO: 15) as well as a starch binding domain (SEQ ID NO: 16). The glucoamylase having the amino acid sequence of SEQ ID NO: 6 includes a catalytic domain (SEQ ID NO: 17) as well as a starch binding domain (SEQ ID NO: 18). In some embodiments, the heterologous polypeptide having glucoamylase activity can include the catalytic domain of SEQ ID NO: 15 or 17, a functional variant thereof (having catalytic activity) or a functional fragment thereof (having catalytic activity). In some additional embodiments, the heterologous polypeptide having glucoamylase activity can include the starch binding domain of SEQ ID NO: 16 or 18, a functional variant thereof (having starch binding activity) or a functional fragment thereof (having starch binding activity). In some specific embodiments, the heterologous polypeptide having glucoamylase activity can include the catalytic domain of SEQ ID NO: 15 (a variant thereof or a fragment thereof having catalytic activity) and the starch binding domain of SEQ ID NO: 18 (a variant thereof or a fragment thereof having starch binding activity). In some specific embodiments, the heterologous polypeptide having glucoamylase activity can include the catalytic domain of SEQ ID NO: 16 (a variant thereof or a fragment thereof having catalytic activity) and the starch binding domain of SEQ ID NO: 17 (a variant thereof or a fragment thereof having starch binding activity).

In embodiments in which the heterologous polypeptide having glucoamylase activity comprises the catalytic domain of SEQ ID NO: 15 (a variant thereof or a fragment thereof), the first polynucleotide can comprise the nucleic acid sequence of SEQ ID NO: 33 (a variant thereof or a fragment thereof) or a degenerate version encoding SEQ ID NO: 15 (a variant thereof or a fragment thereof). In embodiments in which the heterologous polypeptide having glucoamylase activity comprises the starch binding domain of SEQ ID NO: 16 (a variant thereof or a fragment thereof), the first polynucleotide can comprise the nucleic acid sequence of SEQ ID NO: 35 (a variant thereof or a fragment thereof) or a degenerate version encoding SEQ ID NO: 16 (a variant thereof or a fragment thereof). In embodiments in which the heterologous polypeptide having glucoamylase activity comprises the catalytic domain of SEQ ID NO: 17 (a variant thereof or a fragment thereof), the first polynucleotide can comprise the nucleic acid sequence of SEQ ID NO: 34 (a variant thereof or a fragment thereof) or a degenerate version encoding SEQ ID NO: 17 (a variant thereof or a fragment thereof). In embodiments in which the heterologous polypeptide having glucoamylase activity comprises the starch binding domain of SEQ ID NO: 18 (a variant thereof or a fragment thereof), the first polynucleotide can comprise the nucleic acid sequence of SEQ ID NO: 36 (a variant thereof or a fragment thereof) or a degenerate version encoding SEQ ID NO: 18 (a variant thereof or a fragment thereof).

In some alternative embodiments, the polypeptides having glucoamylase activity can be derived from a fungus, for example, from the genus *Penicillum* sp. and, in some instances, from the species *Penicillum oxalicum*. In some embodiments, the heterologous polypeptide is the glucoamylase from *P. oxalicum* described in Xu et al., 2016. In some specific embodiments, the heterologous polypeptide having starch digesting glucoamylase activity can have the amino acid sequence of SEQ ID NO: 6, be a variant of the amino acid sequence of SEQ ID NO: 6 (having glucoamylase activity) or be a fragment of the amino acid sequence of SEQ ID NO: 6 (having glucoamylase activity). In yet another specific embodiment, the heterologous nucleic acid molecule can comprise the nucleic acid sequence of SEQ ID NO: 4, be a variant of the nucleic acid sequence of SEQ ID NO: 4 (encoding a glucoamylase), be a fragment of the nucleic acid sequence of SEQ ID NO: 4 (encoding a glucoamylase) or a degenerate sequence encoding SEQ ID NO: 5. In another specific embodiment, the heterologous polypeptide having starch digesting glucoamylase activity can have the amino acid sequence of SEQ ID NO: 19, be a variant of the amino acid sequence of SEQ ID NO: 19 (having glucoamylase activity) or be a fragment of the amino acid sequence of SEQ ID NO: 19 (having glucoamylase activity). In yet another specific embodiment, the heterologous nucleic acid molecule can comprise the nucleic acid sequence of SEQ ID NO: 26, be a variant of the nucleic acid sequence of SEQ ID NO: 26 (encoding a glucoamylase), be a fragment of the nucleic acid sequence of SEQ ID NO: 26 (encoding a glucoamylase) or a degenerate sequence encoding SEQ ID NO: 19.

A variant glucoamylase comprises at least one amino acid difference (substitution or addition) when compared to the wild-type amino acid sequence of the glucoamylase polypeptide of SEQ ID NO: 5, 6 or 19 and still exhibits glucoamylase activity. In an embodiment, the variant glucoamylase exhibits at least 50%, 60%, 70%, 80%, 90%, 95%, 96%, 97%, 98% or 99% of the activity of the native or wild-type glucoamylase having the amino acid sequence of SEQ ID NO: 5, 6 or 19. The glucoamylase variants also have at least 70%, 80%, 85%, 86%, 87%, 88%, 89%, 90%, 91%, 92%, 93%, 94%, 95%, 96%, 97%, 98% or 99% identity when compared to the wild-type or native glucoamylase having the amino acid sequence of SEQ ID NO: 5, 6 or 19. The term "percent identity", as known in the art, is a relationship between two or more polypeptide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant glucoamylases described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions are known in the art and are included herein. Non-conservative substitutions, such as replacing a basic amino acid with a hydrophobic one, are also well-known in the art.

A glucoamylase can also be a conservative variant or an allelic variant. As used herein, a conservative variant refers to alterations in the amino acid sequence that do not adversely affect the biological functions of the starch digesting glucoamylase. A substitution, insertion or deletion is said to adversely affect the polypeptide when the altered sequence prevents or disrupts a biological function associated with the starch digesting glucoamylase (e.g., the hydrolysis of starch into glucose). For example, the overall charge, structure or hydrophobic-hydrophilic properties of the polypeptide can be altered without adversely affecting a biological activity. Accordingly, the amino acid sequence can be altered, for example to render the peptide more hydrophobic or hydrophilic, without adversely affecting the biological activities of the starch digesting glucoamylase.

The present disclosure also provide fragments of the glucoamylase and glucoamylase variants described herein. A fragment comprises at least one less amino acid residue when compared to the amino acid sequence of the glucoamylase polypeptide or variant and still possess the enzymatic activity of the full-length glucoamylase. In some embodiment, a fragment of a glucoamylase comprising a signal sequence corresponds to the glucoamylase to which the signal sequence have been cleaved or removed. In an embodiment, the glucoamylase fragment exhibits at least 50%, 60%, 70%, 80%, 90%, 95%, 96%, 97%, 98% or 99% activity when compared to the full-length glucoamylase having the amino acid of SEQ ID NO: 5, 6 or 19 or variants thereof. The glucoamylase fragments can also have at least 70%, 80%, 85%, 86%, 87%, 88%, 89%, 90%, 91%, 92%, 93%, 94%, 95%, 96%, 97%, 98% or 99% identity when compared to the glucoamylase having the amino acid sequence of SEQ ID NO: 5, 6 or 19 or fragments thereof. The fragment can be, for example, a truncation of one or more amino acid residues at the amino-terminus, the carboxy terminus or both termini of the starch digesting glucoamylase polypeptide or variant. Alternatively or in combination, the fragment can be generated from removing one or more internal amino acid residues. In an embodiment, the glucoamylase fragment has at least 100, 150, 200, 250, 300, 350, 400, 450, 500, 550, 600 or more consecutive amino acids of the glucoamylase having the amino acid sequence of SEQ ID NO: 5, 6 or 19 or variants thereof.

In some embodiments, the heterologous nucleic acid molecule includes a (second) heterologous polynucleotide encoding a signal sequence. As it is known in the art, a signal sequence corresponds to a short stretch of amino acid residues (usually no longer than 50 contiguous amino acids and usually located at the amino terminus of the polypeptide) which are capable of guiding the remainder of the polypeptide for secretion. The signal sequence is usually cleaved upon the secretion of the polypeptide and thus is not necessarily involved with the enzymatic activity of the secreted polypeptide (e.g., glucoamylase activity in the present disclosure). In embodiments, the signal sequence encoded by the heterologous nucleic acid molecule (which can be associated with the heterologous polypeptide having glucoamylase activity) is not natively associated with the *P. oxalicum* glucoamylse.

In some embodiments, the first and second polynucleotides are in frame and operatively associated so as to encode a single polypeptide (which is intended to be cleaved so as to release the polypeptide having glucoamylase activity upon the secretion of the single polypeptide). In such embodiments of the heterologous nucleic acid molecule, the second polynucleotide is located upstream (5') with respect to the first polynucleotide. Otherwise stated, in embodiments, the first polynucleotide is located downstream (3') with respect to the second polynucleotide in the heterologous nucleic acid sequence.

The second polynucleotide encodes a signal sequence, a variant of a signal sequence having signal sequence activity or a fragment of a signal sequence having signal sequence activity. A variant signal sequence comprises at least one amino acid difference when compared to the amino acid sequence of the native or wild-type signal sequence and exhibits a biological activity substantially similar to the native (wild-type) signal sequence (e.g., the ability to guide the heterologous polypeptide having glucoamylase activity for secretion). The signal sequence "variants" have at least 50%, 55%, 60%, 65%, 70%, 75%, 80%, 85%, 90%, 95%, 96%, 97%, 98% or 99% of the biological activity when compared to the wild-type signal sequence described herein. The signal sequence "variants" have at least 50%, 55%, 60%, 65%, 70%, 75%, 80%, 85%, 90%, 95%, 96%, 97%, 98% or 99% identity to the wild-type signal sequence described herein. The variant signal sequence described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group. A "variant" of the wild-type signal sequence can be a conservative variant or an allelic variant. As used herein, a conservative variant refers to alterations in the amino acid sequence that do not adversely affect the biological functions of the signal sequence. A substitution, insertion or deletion is said to adversely affect the signal sequence when the altered sequence prevents or disrupts a biological function associated with the signal sequence. For example, the overall charge, structure or hydrophobic-hydrophilic properties of the signal sequence can be altered without adversely affecting a biological activity. Accordingly, the amino acid sequence can be altered, for example to render the signal sequence more hydrophobic or hydrophilic, without adversely affecting the biological activities of the signal sequence.

The signal sequence can be a fragment of the signal sequence or a fragment of a variant signal sequence. A signal sequence fragment comprises at least one less amino acid residue when compared to the amino acid sequence of the full length signal sequence or variant possesses and still possess a biological activity substantially similar to the native full-length signal sequence or variant. The signal sequence "fragments" have at least 50%, 55%, 60%, 65%, 70%, 75%, 80%, 85%, 90%, 95%, 96%, 97%, 98% or 99% of the biological activity when compared to the full-length signal sequence or variants described herein. Signal sequence "fragments" have at least at least 2, 3, 4, 5, 6, 7, 8, 9, 10 or more consecutive amino acids of the full-length signal sequence or variants described herein. The signal sequence "fragments" can have at least 50%, 55%, 60%, 65%, 70%, 75%, 80%, 85%, 90%, 95%, 96%, 97%, 98% or 99% identity to the full-length signal sequence or variants described herein.

The signal sequence can be the native signal sequence associated with the *P. oxalicum* glucoamylase. As such, the signal sequence can have the amino acid sequence of SEQ ID NO: 28, be a variant the amino acid sequence of SEQ ID NO: 28 having signal sequence activity or be a fragment of the amino acid sequence of SEQ ID NO: 28 having signal sequence activity. The second polynucleotide encoding the signal sequence having the amino acid sequence of SEQ ID NO: 28 (as well as variants and fragments thereof) can be operatively associated with the first polynucleotide encoding the polypeptide having glucoamylase activity of SEQ ID NO: 6. As such, the heterologous nucleic acid molecule can encode the polypeptide having the amino acid sequence of SEQ ID NO: 5 (as well as variants and fragments thereof). In such embodiments, upon secretion, the signal sequence having the amino acid sequence of SEQ ID NO: 28 (as well as variants and fragments thereof) is physically dissociated from the polypeptide having glucoamylase activity of SEQ ID NO: 6, resulting in the secretion of a polypeptide having glucoamylase activity of SEQ ID NO: 6.

The signal sequence can be the native signal sequence associated with the alpha(α) mating factor (αMF). In some embodiments, the αMF is from a *Saccharomyces* sp., such as, for example, *Saccharomyces cerevisiae*. It is known in the art that the αMF has two levels of cleavage when used as a leader: a short signal peptide gets cleaved first in the endoplasmic reticulum (e.g., SEQ ID NO: 26), and then a further region gets cleaved later en route to the Golgi (e.g., SEQ ID NO: 27). In some embodiments, the signal sequence can have the amino acid sequence of SEQ ID NO: 25, be a variant the amino acid sequence of SEQ ID NO: 25 having signal sequence activity or be a fragment of the amino acid sequence of SEQ ID NO: 25 having signal sequence activity. The second polynucleotide encoding the signal sequence having the amino acid sequence of SEQ ID NO: 25 (as well as variants and fragments thereof) can be operatively associated with the first polynucleotide encoding the polypeptide having glucoamylase activity of SEQ ID NO: 31. As such, the heterologous nucleic acid molecule can encode the polypeptide having the amino acid sequence of SEQ ID NO: 31 (as well as variants and fragments thereof). In such embodiments, upon secretion, the signal sequence having the amino acid sequence of SEQ ID NO: 25 (as well as variants and fragments thereof) is physically dissociated from the polypeptide having glucoamylase activity of SEQ ID NO: 31, resulting in the secretion of a polypeptide having glucoamylase activity of SEQ ID NO: 6. In some additional embodiments, the signal sequence can have the amino acid sequence of SEQ ID NO: 27, be a variant the amino acid sequence of SEQ ID NO: 27 having signal sequence activity or be a fragment of the amino acid sequence of SEQ ID NO: 27 having signal sequence activity. The second polynucleotide encoding the signal sequence having the amino acid sequence of SEQ ID NO: 27 (as well as variants and fragments thereof) can be operatively associated with the first polynucleotide encoding the polypeptide having glucoamylase activity of SEQ ID NO: 6. As such, the heterologous nucleic acid molecule can encode the polypeptide having the amino acid sequence of SEQ ID NO: 43 (as well as variants and fragments thereof). In such embodiments, upon secretion, the signal sequence having the amino acid sequence of SEQ ID NO: 27 (as well as variants and fragments thereof) is physically dissociated from the polypeptide having glucoamylase activity of SEQ ID NO: 43, resulting in the secretion of a polypeptide having glucoamylase activity of SEQ ID NO: 6.

The signal sequence can be derived from the native signal sequence associated with the alpha(α) mating factor (αMF). In some embodiments, the αMF is from a *Saccharomyces* sp., such as, for example, *Saccharomyces cerevisiae*. In some embodiments, the signal sequence can include one or more amino acid substitution with respect to the wild-type αMF signal sequence (having the amino acid sequence of SEQ ID NO: 25 or 27). In some specific embodiments, the signal sequence can include one or both L42S and D83E (when compared to the wild-type αMF signal sequence of SEQ ID NO: 25). In some additional embodiments, the signal sequence can have the amino acid sequence of SEQ ID NO: 47, be a variant the amino acid sequence of SEQ ID NO: 47 having signal sequence activity or be a fragment of the amino acid sequence of SEQ ID NO: 47 having signal sequence activity. The second polynucleotide encoding the signal sequence having the amino acid sequence of SEQ ID NO: 47 (as well as variants and fragments thereof) can be operatively associated with the first polynucleotide encoding the polypeptide having glucoamylase activity of SEQ ID NO: 6. As such, the heterologous nucleic acid molecule can encode the polypeptide having the amino acid sequence of SEQ ID NO: 45 (as well as variants and fragments thereof). In such embodiments, upon secretion, the signal sequence having the amino acid sequence of SEQ ID NO: 47 (as well as variants and fragments thereof) is physically dissociated from the polypeptide having glucoamylase activity of SEQ ID NO: 6, resulting in the secretion of a polypeptide having glucoamylase activity of SEQ ID NO: 6. In some additional embodiments, the signal sequence can have the amino acid sequence of SEQ ID NO: 24, be a variant the amino acid sequence of SEQ ID NO: 24 having signal sequence activity or be a fragment of the amino acid sequence of SEQ ID NO: 24 having signal sequence activity. The second polynucleotide encoding the signal sequence having the amino acid sequence of SEQ ID NO: 24 (as well as variants and fragments thereof) can be operatively associated with the first polynucleotide encoding the polypeptide having glucoamylase activity of SEQ ID NO: 6. As such, the heterologous nucleic acid molecule can encode the polypeptide having the amino acid sequence of SEQ ID NO: 49 (as well as variants and fragments thereof). In such embodiments, upon secretion, the signal sequence having the amino acid sequence of SEQ ID NO: 24 (as well as variants and fragments thereof) is physically dissociated from the polypeptide having glucoamylase activity of SEQ ID NO: 6, resulting in the secretion of a polypeptide having glucoamylase activity of SEQ ID NO: 6.

The signal sequence can be the native signal sequence associated with the OST1 polypeptide. In some embodiments, the OST1 polypeptide is from a *Saccharomyces* sp., such as, for example, *Saccharomyces cerevisiae*. In some embodiments, the signal sequence can have the amino acid sequence of SEQ ID NO: 23, be a variant the amino acid sequence of SEQ ID NO: 23 having signal sequence activity or be a fragment of the amino acid sequence of SEQ ID NO: 23 having signal sequence activity. The second polynucleotide encoding the signal sequence having the amino acid sequence of SEQ ID NO: 23 (as well as variants and fragments thereof) can be operatively associated with the first polynucleotide encoding the polypeptide having glucoamylase activity of SEQ ID NO: 6. As such, the heterologous nucleic acid molecule can encoding the polypeptide having the amino acid sequence of SEQ ID NO: 32 (as well as variants and fragments thereof). In such embodiments, upon secretion, the signal sequence having the amino acid sequence of SEQ ID NO: 23 (as well as variants and fragments thereof) is physically dissociated from the polypeptide having glucoamylase activity of SEQ ID NO: 6, resulting in the secretion of a polypeptide having glucoamylase activity of SEQ ID NO: 6.

In some additional embodiments, the signal sequence can be a hybrid signal sequence associated with the αMF and the OST1 polypeptide, such as the one described in Barrero et al., 2018 and having the amino acid sequence of SEQ ID NO: 21. In some embodiments, the signal sequence can have the amino acid sequence of SEQ ID NO: 21, be a variant the amino acid sequence of SEQ ID NO: 21 having signal sequence activity or be a fragment of the amino acid sequence of SEQ ID NO: 21 having signal sequence activity. The second polynucleotide encoding the signal sequence having the amino acid sequence of SEQ ID NO: 21 (as well as variants and fragments thereof) can be operatively associated with the first polynucleotide encoding the polypeptide having glucoamylase activity of SEQ ID NO: 6. As such, the heterologous nucleic acid molecule can encoding the polypeptide having the amino acid sequence of SEQ ID NO: 29 (as well as variants and fragments thereof). In such embodiments, upon secretion, the signal sequence having the amino acid sequence of SEQ ID NO: 21 (as well as variants and fragments thereof) is physically dissociated from the polypeptide having glucoamylase activity of SEQ ID NO: 6, resulting in the secretion of a polypeptide having glucoamylase activity of SEQ ID NO: 6.

Because, in some embodiments, the heterologous nucleic acid molecule of the present disclosure includes a signal sequence, the heterologous polypeptides having glucoamylase activity described herein are secreted polypeptides. In some embodiments, secreted heterologous polypeptides having glucoamylase activity are released in the culture/fermentation medium and do not remain physically attached to the recombinant yeast host cell. In alternative embodiments, the heterologous glucoamylases of the present disclosure can be secreted, but they remain physically associated with the recombinant yeast host cell. In an embodiment, at least one portion (usually at least one terminus) of the heterologous glucoamylase is bound, covalently, non-covalently and/or electrostatically for example, to the cell wall (and in some embodiments to the cytoplasmic membrane). For example, the heterologous glucoamylase can be modified to bear one or more transmembrane domains, to have one or more lipid modifications (myristoylation, palmitoylation, farnesylation and/or prenylation), to interact with one or more membrane-associated polypeptide and/or to interactions with the cellular lipid rafts. While the heterologous glucoamylases may not be directly bound to the cell membrane or cell wall (e.g., such as when binding occurs via a tethering moiety), the polypeptide is nonetheless considered a "cell-associated" heterologous polypeptide according to the present disclosure.

In some embodiments, the heterologous glucoamylase can be expressed to be located at and associated to the cell wall of the recombinant yeast host cell. In some embodiments, the heterologous glucoamylase is expressed to be located at and associated to the external surface of the cell wall of the host cell. Recombinant yeast host cells all have a cell wall (which includes a cytoplasmic membrane) defining the intracellular (e.g., internally-facing the nucleus) and extracellular (e.g., externally-facing) environments. The heterologous glucoamylase can be located at (and in some embodiments, physically associated to) the external face of the recombinant yeast host's cell wall and, in further embodiments, to the external face of the recombinant yeast host's cytoplasmic membrane. In the context of the present disclosure, the expression "associated to the external face of the cell wall/cytoplasmic membrane of the recombinant yeast host cell" refers to the ability of the heterologous glucoamylase to physically integrate (in a covalent or non-covalent fashion), at least in part, in the cell wall (and in some embodiments in the cytoplasmic membrane) of the recombinant yeast host cell. The physical integration can be attributed to the presence of, for example, a transmembrane domain on the heterologous polypeptide, a domain capable of interacting with a cytoplasmic membrane polypeptide on the heterologous polypeptide, a post-translational modification made to the heterologous polypeptide (e.g., lipidation), etc.

In some circumstances, it may be warranted to increase or provide cell association to some heterologous glucoamylases because they exhibit insufficient intrinsic cell association or simply lack intrinsic cell association. In such embodiment, it is possible to provide the heterologous glucoamylase as a chimeric construct by combining it with a tethering amino acid moiety which will provide or increase attachment to the cell wall of the recombinant yeast host cell. In such embodiment, the heterologous polypeptide will be considered "tethered". It is preferred that the amino acid tethering moiety of the polypeptide be neutral with respect to the biological activity of the heterologous glucoamylase, e.g., does not interfere with the biological activity (such as, for example, the enzymatic activity) of the heterologous glucoamylase. In some embodiments, the association of the amino acid tethering moiety with the heterologous glucoamylase can increase the biological activity of the heterologous polypeptide (when compared to the non-tethered, "free" form).

In an embodiment, a tethering moiety can be used to be expressed with the heterologous glucoamylase to locate the heterologous polypeptide to the wall of the recombinant yeast host cell. Various tethering amino acid moieties are known art and can be used in the context of the present disclosure. The tethering moiety can be a transmembrane domain found on another polypeptide and allow the tethered polypeptide to have a transmembrane domain. In such embodiment, the tethering moiety can be derived from the FLO1 polypeptide. In still another example, the amino acid tethering moiety can be modified post-translation to include a glycosylphosphatidylinositol (GPI) anchor and allow the tethered polypeptide to have a GPI anchor. GPI anchors are glycolipids attached to the terminus of a polypeptide (and in some embodiments, to the carboxyl terminus of a polypeptide) which allows the anchoring of the polypeptide to the cytoplasmic membrane of the cell membrane. Tethering amino acid moieties capable of providing a GPI anchor include, but are not limited to those associated with/derived from a SED1 polypeptide, a TIR1 polypeptide, a CWP2 polypeptide, a CCW12 polypeptide, a SPI1 polypeptide, a PST1 polypeptide or a combination of a AGA1 and a AGA2 polypeptide. In an embodiment, the tethering moiety provides a GPI anchor and, in still a further embodiment, the tethering moiety is derived from the SPI1 polypeptide or the CCW12 polypeptide.

The tethering amino acid moiety can be a variant of a known/native tethering amino acid moiety. The tethering amino acid moiety can be a fragment of a known/native tethering amino acid moiety or fragment of a variant of a known/native tethering amino acid moiety.

In embodiments in which an amino acid tethering moiety and/or signal sequence may be desirable, the heterologous polypeptide can be provided as a thetered polypeptide expressed by the recombinant yeast host cell and having one of the following formulae:

(NH$_2$)SS-HP-L-TT(COOH)  (I) or

(NH$_2$)SS-TT-L-HP(COOH)  (II)

In both of these formulae, the residue "HP" refers to a heterologous starch digesting glucoamylase moiety, the residue "SS" refers to a signal sequence, the residue "L" refers to the presence of an optional linker, and the residue "TT" refers to an optional amino acid tethering moiety. In the tethered polypeptides of formula (I), the amino (NH$_2$ or N) terminus of the amino acid tether is located (directly or indirectly) at the carboxyl (COOH or C) terminus of the heterologous glucoamylase moiety. In the tethered polypeptides of formula (I), the amino (NH$_2$ or N) terminus of the heterologous glucoamylase moiety is located (directly or indirectly) at the carboxyl (COOH or C) terminus of the signal sequence. In the tethered polypeptides of formula (II), the carboxy (COOH or C) terminus of the amino acid tether is located (directly or indirectly) at the amino (NH$_2$ or N) terminus of the heterologous glucoamylase moiety. In the tethered polypeptides of formula (II), the carboxy (COOH or C) terminus of signal sequence is located (directly or indirectly) at the amino (NH$_2$ or N) terminus of the amino acid tether. Embodiments of tethered heterologous polypeptides have been disclosed in WO20181167670 and are included herein in their entirety.

The heterologous nucleic acid molecule can include a third polynucleotide including a promoter capable of controlling the expression of the first and second polynucleotide. In such embodiment, the promoter and the polynucleotides coding for the signal sequence (second polynucleotide) and the heterologous polypeptide (first polynucleotide) are operatively linked to one another. In the context of the present disclosure, the expressions "operatively linked" or "operatively associated" refers to fact that the promoter is physically associated to the first and second polynucleotide in a manner that allows, under certain conditions, for expression of the heterologous polypeptide from the heterologous nucleic acid molecule. In an embodiment, the promoter can be located upstream (5') of the nucleic acid sequence coding for the heterologous polypeptide. In still another embodiment, the promoter can be located downstream (3') of the nucleic acid sequence coding for the heterologous polypeptide. In the context of the present disclosure, one or more than one promoter can be included in the nucleic acid molecule. When more than one promoter is included in the nucleic acid molecule, each of the promoters is operatively linked to the nucleic acid sequence coding for the polypeptide. The promoters can be located, in view of the nucleic acid molecule coding for the polypeptide, upstream, downstream as well as both upstream and downstream.

"Promoter" refers to a DNA fragment capable of controlling the expression of a coding sequence or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as polypeptide binding domains (consensus sequences) responsible for the binding of the polymerase.

The promoter can be heterologous to the nucleic acid molecule encoding the heterologous polypeptide. The promoter can be heterologous or derived from a strain being from the same genus or species as the recombinant host cell. In an embodiment, the promoter is derived from the same genus or species of the yeast host cell and the polypeptide is derived from different genera that the host cell. One or more promoters can be used to allow the expression of the polypeptides in the recombinant yeast host cell.

In some embodiments, the recombinant yeast host cell is a facultative anaerobe, such as *Saccharomyces cerevisiae*. For facultative anaerobes, cells tend to propagate or ferment depending on the availability of oxygen. In a fermentation process, yeast cells are generally allowed to propagate before fermentation is conducted. In some embodiments, the promoter can initiate transcription during a propagation phase such that the heterologous polypeptides (variants or fragments) are expressed during the propagation phase. As used in the context of the present disclosure, the expression "propagation phase" refers to an expansion phase of a commercial process in which the yeasts are propagated under aerobic conditions. In some instances, the propagated biomass can be used in a following fermenting step (e.g. under anaerobic conditions) to maximize the production of one or more desired metabolites or fermentation products. This embodiment will allow the accumulation of the polypeptide associated with the recombinant yeast host cell prior to any subsequent use, for example in liquefaction or fermentation. In some embodiments, the promoter substantially limits the expression of the polypeptide during the propagation phase.

The expression of the polypeptides during the propagation phase may provide sufficient expression such that the polypeptide or the recombinant yeast cells may be added during the liquefaction of starch, thereby providing yeast cells with sufficient nutrients to undergo metabolic processing. The promoters can be native or heterologous to the heterologous gene encoding the heterologous polypeptide. The promoters that can be included in the heterologous nucleic acid molecule can be constitutive or inducible promoters. Constitutive promoters include, but are not limited to, tef2p (e.g., the promoter of the tef2 gene, a variant thereof or a fragment thereof), cwp2p (e.g., the promoter of the cwp2 gene, a variant thereof or a fragment thereof), ssa1p (e.g., the promoter of the ssa1 gene, a variant thereof), eno1p (e.g., the promoter of the eno1 gene, variant thereof or a fragment thereof), hxk1 (e.g., the promoter of the hxk1 gene, a variant thereof or a fragment thereof) and/or pgk1p (e.g., the promoter of the pgk1 gene, a variant thereof or a fragment thereof). Inducible promoters include, but are not limited to glucose-regulated promoters (e.g., the promoter of the hxt7 gene (referred to as hxt7p), a functional variant or a functional fragment thereof; the promoter of the ctt1 gene (referred to as ctt1p), a functional variant or a functional fragment thereof; the promoter of the glo1 gene (referred to as glo1p), a functional variant or a functional fragment thereof; the promoter of the ygp1 gene (referred to as ygp1p), a functional variant or a functional fragment thereof; the promoter of the gsy2 gene (referred to as gsy2p), a functional variant or a functional fragment thereof), molasses-regulated promoters (e.g., the promoter of the mol1 gene (referred to as mol1 p), a functional variant or a functional fragment thereof), heat shock-regulated promoters (e.g., the promoter of the glo1 gene (referred to as glo1p), a functional variant or a functional fragment thereof; the promoter of the sti1 gene (referred to as sti1p), a functional variant or a functional fragment thereof; the promoter of the ygp1 gene (referred to as ygp1p), a functional variant or a functional fragment thereof; the promoter of the gsy2 gene (referred to as gsy2p), a functional variant or a functional fragment thereof), oxidative stress response promoters (e.g., the promoter of the cup1 gene (referred to as cup1p), a functional variant or a functional fragment thereof; the promoter of the ctt1 gene (referred to as ctt1p), a functional variant or a functional fragment thereof; the promoter of the trx2 gene (referred to as trx2p), a functional variant or a functional fragment thereof; the promoter of the gpd1 gene (referred to as gpd1p), a functional variant or a functional fragment thereof; the promoter of the hsp12 gene (referred to as hsp12p), a functional variant or a functional fragment thereof), osmotic stress response promoters (e.g., the promoter of the ctt1 gene (referred to as ctt1p), a functional variant or a functional fragment thereof; the promoter of the glo1 gene (referred to as glo1p), a functional variant or a functional fragment thereof; the promoter of the gpd1 gene (referred to as gpd1p), a functional variant or a functional fragment thereof; the promoter of the ygp1 gene (referred to as ygp1p), a functional variant or a functional fragment thereof), nitrogen-regulated promoters (e.g., the promoter of the ygp1 gene (referred to as ygp1p), a functional variant or a functional fragment thereof) and the promoter of the adh1 gene (referred to as adh1p), a functional variant or a functional fragment thereof) and/or a molasses-regulated promoter (e.g., the promoter of the tir1 gene (referred to as tir1p), a functional variant or a functional fragment thereof).

Promoters that can be included in the heterologous nucleic acid molecule of the present disclosure include, without limitation, one or more of the promoter of the tdh1 gene (referred to as tdh1p, a functional variant or a functional fragment thereof), of the hor7 gene (referred to as hor7p, a functional variant or a functional fragment thereof), of the hsp150 gene (referred to as hsp150p, a functional variant or a functional fragment thereof), of the hxt7 gene (referred to as hxt7p, a functional variant or a functional fragment thereof), of the gpm1 gene (referred to as gpm1p, a functional variant or a functional fragment thereof), of the pgk1 gene (referred to as pgk1p, a functional variant or a functional fragment thereof), of the stl1 gene (referred to as stl1p, a functional variant or a functional fragment thereof), of the qcr8 gene (referred to as qcr8p, a functional variant or a functional fragment thereof) and/or of the tef2 gene (referred to as tef2p, a functional variant or a functional fragment thereof). In an embodiment, the promoter is or comprises the tef2p. In still another embodiment, the promoter comprises or consists essentially of the adh1p and the qcr8p. In a further embodiment, the promoter is the thd1p. In another embodiment, the promoter is the adh1p.

In another embodiment, the third polynucleotide can comprise a constitutive promoter.

In another embodiment, the third polynucleotide can comprise a promoter capable of initiating transcription during fermentation such that the heterologous polypeptides (variants or fragments) are expressed during the fermentation. As used in the context of the present disclosure, the expression "fermentation" refers to a phase of a commercial process in which the yeasts, after having been propagated, are used to convert a biomass into a fermentation product. During fermentation, partial anaerobic or anaerobic conditions are often present. This embodiment will allow the accumulation of the heterologous polypeptide during liquefaction or fermentation. In some embodiments, the promoter substantially limits the expression of the polypeptide during fermentation. The first heterologous promoter (or combination thereof) can include without limitation anaerobic-regulated promoters (also referred to anaerobic specific promoters), heat shock-regulated promoters, oxidative stress response promoters and osmotic stress response promoters. As used in the context of the present disclosure, an anaerobic-regulated promoter refers to a promoter capable of favoring the expression of its associated open-reading frame (e.g., the nucleic acid molecule encoding the first heterologous polypeptide) in the presence of anaerobia (partial or complete). Anaerobic-regulated promoters include, but are not limited to, the promoter of the YER011W or tir1 gene (referred to as tir1p), of the YFL020C or pau5 gene (referred to as pau5p) and of the YJR150C or dan1 gene (referred to as dan1p).

In the context of the present disclosure, the expression "functional fragment of a promoter" when used in combination to a promoter refers to a shorter nucleic acid sequence than the native promoter which retain the ability to control the expression of the nucleic acid sequence encoding the polypeptides during the propagation phase of the recombinant yeast host cells. Usually, functional fragments are either 5' and/or 3' truncation of one or more nucleic acid residue from the native promoter nucleic acid sequence.

In some embodiments, the heterologous nucleic acid molecules include one or a combination of terminator sequence(s) to end the translation of the heterologous polypeptide. The terminator can be native or heterologous to the nucleic acid sequence encoding the heterologous polypeptide or its corresponding chimera. In some embodiments, one or more terminators can be used. In some embodiments, the terminator comprises the terminator derived from is from the dit1 gene (dit1t, a functional variant or a functional fragment thereof), from the idp1 gene (idp1t, a functional variant or a functional fragment thereof), from the gpm1 gene (gpm1t, a functional variant or a functional fragment thereof), from the pma1 gene (pam1t, a functional variant or a functional fragment thereof), from the tdh3 gene (tdh3t, a functional variant or a functional fragment thereof), from the hxt2 gene (a functional variant or a functional fragment thereof), from the adh3 gene (adh3t, a functional variant or a functional fragment thereof), and/or from the ira2 gene (ira2t, a functional variant or a functional fragment thereof). In an embodiment, the terminator comprises or is derived from the dit1 gene (dit1t, a functional variant or a functional fragment thereof). In an embodiment, the terminator is from the adh3 gene (adh3t, a functional variant or a functional fragment thereof). In the context of the present disclosure, the expression "functional variant of a terminator" refers to a nucleic acid sequence that has been substituted in at least one nucleic acid position when compared to the native terminator which retain the ability to end the expression of the nucleic acid sequence coding for the heterologous polypeptide or its corresponding chimera. In the context of the present disclosure, the expression "functional fragment of a terminator" refers to a shorter nucleic acid sequence than the native terminator which retain the ability to end the expression of the nucleic acid sequence coding for the heterologous polypeptide or its corresponding chimera.

Process for Saccharification and Fermentation of a Biomass

The recombinant yeast host cells described herein can be used in saccharification for improving the hydrolysis of a biomass and, in some embodiments, the production of a fermentation product from the biomass. In some embodiments, the recombinant yeast host cells of the present disclosure maintain their robustness during saccharification and fermentation in the presence of a stressor such as, for example, lactic acid, formic acid and/or a bacterial contamination (that can be associated, in some embodiments, the an increase in lactic acid during fermentation), a decrease in pH, a reduction in aeration, elevated temperatures or a combination of these conditions. The fermented product can be an alcohol, such as, for example, ethanol, isopropanol, n-propanol, 1-butanol, methanol, 1,3-propanediol and/or 1,2-propanediol and/or a ketone, such as, for example, acetone. In an embodiment, the fermented product is ethanol.

The biomass that can be hydrolyzed (and optionally fermented) with the recombinant yeast host cells as described herein includes any type of biomass known in the art and described herein. For example, the biomass can include, but is not limited to, starch, sugar and lignocellulosic materials. Starch materials can include, but are not limited to, mashes such as corn, wheat, rye, barley, rice, or milo. Starch can be provided in a raw form or in a heat-treated form. Sugar materials can include, but are not limited to, sugar beets, artichoke tubers, sweet sorghum, molasses or cane. The terms "lignocellulosic material", "lignocellulosic substrate" and "cellulosic biomass" mean any type of substrate comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, waste-water-treatment sludge, municipal solid waste, corn fiber from wet and dry mill corn ethanol plants and sugar-processing residues. The terms "hemicellulosics", "hemicellulosic portions" and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan and galactoglucomannan), pectins (e.g., homogalacturonans, rhamnogalacturonan I and II, and xylogalacturonan) and proteoglycans (e.g., arabinogalactan-polypeptide, extensin, and pro line-rich polypeptides).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, molasses, sugarcane, leaves, agricultural and forestry residues, grasses such as switchgrass, ruminant digestion products, municipal wastes, paper mill effluent, newspaper, cardboard or combinations thereof.

Paper sludge is also a viable feedstock for lactate or acetate production. Paper sludge is solid residue arising from pulping and paper-making, and is typically removed from process wastewater in a primary clarifier. The cost of disposing of wet sludge is a significant incentive to convert the material for other uses, such as conversion to ethanol.

Processes provided by the present invention are widely applicable. Moreover, the hydrolyzed biomass may be used to produce ethanol or higher value added chemicals, such as organic acids, aromatics, esters, acetone and polymer intermediates.

The process of the present disclosure comprise contacting the recombinant host cells described herein with a biomass so as to allow the hydrolysis of at least a part of the biomass and the conversion of the biomass (at least in part) into a fermentation product (e.g., an alcohol such as ethanol). In some embodiments, the biomass to be hydrolyzed/fermented is a lignocellulosic biomass and, in some embodiments, it comprises starch (in a gelatinized or raw form). In an embodiment, the biomass to be hydrolyzed/fermented is raw starch. In other embodiments, the biomass to be hydrolyzed/fermented is derived from corn, potato, cassava, rice, or buckwheat. In an embodiment, the biomass is derived from corn, such as in the form of corn mash or in a raw form. The process can include, in some embodiments, heating the lignocellulosic biomass prior to fermentation to provide starch in a gelatinized form.

In the process described herein, it is possible to add an exogenous source (e.g., to dose) of an enzyme to facilitate saccharification or improve fermentation yield. As such, the process can comprise including one or more dose(s) of one or more enzyme(s) during the saccharification and/or the fermentation step. The exogenous enzyme that can be used during the saccharification/fermentation process can include, without limitation, an alpha-amylase, a glucoamylase, a protease, a phytase, a pullulanase, a cellulase, a hemi-cellulase such as a xylanase, a trehalase, or any combination thereof. The exogenous enzyme can be provided, in some embodiments, in a purified form and/or provided as part of a cocktail.

The process of the present disclosure can include a step of adding a dose (or multiple doses) of an exogenous enzyme (which may be purified) to increase the fermentation yield or allow the yeast to complete the fermentation. In such embodiment, the requirement to add one or more dose(s) can be determined prior to or during fermentation.

The fermentation process can be performed at temperatures of at least about 20° C., about 21° C., about 22° C., about 23° C., about 24° C., about 25° C., about 26° C., about 27° C., about 28° C., about 29° C., about 30° C., about 31° C., about 32° C., about 33°, about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments, the production of ethanol from cellulose can be performed, for example, at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C. In some embodiments, the recombinant microbial host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the liquefaction of starch occurs in the presence of recombinant host cells described herein. In some embodiments, the liquefaction of starch is maintained at a temperature of between about 70° C.-105° C. to allow for proper gelatinization and hydrolysis of the crystalline starch. In an embodiment, the liquefaction occurs at a temperature of at least about 70° C., 75° C., 80° C., 85° C., 90° C., 95° C., 100° C. or 105° C. Alternatively or in combination, the liquefaction occurs at a temperate of no more than about 105° C., 100° C., 95° C., 90° C., 85° C., 80° C., 75° C. or 70° C. In yet another embodiment, the liquefaction occurs at a temperature between about 80° C. and 85° C. (which can include a thermal treatment spike at 105° C.).

In some embodiments, the process can be used to produce ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, at least about 500 mg per hour per liter, at least about 600 mg per hour per liter, at least about 700 mg per hour per liter, at least about 800 mg per hour per liter, at least about 900 mg per hour per liter, at least about 1 g per hour per liter, at least about 1.5 g per hour per liter, at least about 2 g per hour per liter, at least about 2.5 g per hour per liter, at least about 3 g per hour per liter, at least about 3.5 g per hour per liter, at least about 4 g per hour per liter, at least about 4.5 g per hour per liter, at least about 5 g per hour per liter, at least about 5.5 g per hour per liter, at least about 6 g per hour per liter, at least about 6.5 g per hour per liter, at least about 7 g per hour per liter, at least about 7.5 g per hour per liter, at least about 8 g per hour per liter, at least about 8.5 g per hour per liter, at least about 9 g per hour per liter, at least about 9.5 g per hour per liter, at least about 10 g per hour per liter, at least about 10.5 g per hour per liter, at least about 11 g per hour per liter, at least about 11.5 g per hour per liter, at least about 12 g per hour per liter, at least about 12.5 g per hour per liter, at least about 13 g per hour per liter, at least about 13.5 g per hour per liter, at least about 14 g per hour per liter, at least about 14.5 g per hour per liter or at least about 15 g per hour per liter.

Ethanol production can be measured using any method known in the art. For example, the quantity of ethanol in fermentation samples can be assessed using HPLC analysis. Many ethanol assay kits are commercially available that use, for example, alcohol oxidase enzyme based assays.

In some embodiments, the process can be used in the presence of a stressor such as low pH. For example, the stressor is s pH of 7.0 or lower, 6.5 or lower, 6.0 or lower, 5.5 or lower, 5.0 or lower, 4.8 or lower, 4.6 or lower, 4.4 or lower, 4.2 or lower, 4.0 or lower, 3.8 or lower, 3.6 or lower, 3.4 or lower, 3.2 or lower, or 3.0 or lower.

As shown in the Examples, recombinant yeast host cells expressing the heterologous glucoamylase exhibits enhanced robustness compared to other known glucoamylases. In specific embodiments of a recombinant yeast host cell expressing a heterologous glucoamylase, fermentation with the recombinant yeast cell yielded higher ethanol titers than recombinant yeast host cells expressing other heterologous glucoamylases. In some embodiments, the recombinant yeast host cell expressing heterologous glucoamylase yielded greater than 10 mg/L increase, greater than 25 mg/L increase, greater than 50 mg/L increase, greater than 100 mg/L increase, greater than 200 mg/L increase, greater than 300 mg/L increase, greater than 400 mg/L increase, greater than 500 mg/L increase, greater than 600 mg/L increase, greater than 700 mg/L increase, greater than 800 mg/L increase, greater than 900 mg/L increase, or greater than 1 g/L increase) in ethanol production at low pH values and in corn fermentation when compared to a recombinant yeast host cells expressing other heterologous glucoamylases.

Yeast Products and Compositions

The recombinant yeast host cells of the present disclosure can be used in the preparation of a yeast composition (e.g., a composition comprising the recombinant yeast host cell) comprising the heterologous polypeptide having glucoamylase activity. The yeast compositions and products can be provided in a liquid, semi-liquid or dry form.

A yeast composition refers to a composition comprising the recombinant yeast host cell of the present disclosure (which may be, in some embodiments, a viable recombinant yeast host cell) as well as the heterologous polypeptide having glucoamylase activity. The process for providing a yeast composition comprises providing a propagated the recombinant yeast host cell and removing, at least one component of the mixture obtained after propagation to provide the yeast composition. This component can be, without limitation, water, amino acids, peptides and proteins, nucleic acid residues and nucleic acid molecules, cellular debris, fermentation products, etc. In an embodiment, the process comprises substantially isolating the propagated recombinant yeast host cells from the components of the propagation medium. As used in the context of the present disclosure, the expression "substantially isolating" refers to the removal of the majority of the components of the propagation medium from the propagated recombinant yeast host cells. In some embodiments, "substantially isolating" refers to concentrating the propagated recombinant yeast host cell to at least 5, 10, 15, 20, 25, 30, 35, 45% or more when compared to the concentration of the recombinant yeast host cell prior to the isolation. In order to provide the yeast composition, the propagated recombinant yeast host cells can be centrifuged (and the resulting cellular pellet comprising the propagated recombinant yeast host cells can optionally be washed), filtered and/or dried (optionally using a vacuum-drying technique). The isolated recombinant yeast host cells can then be formulated in a yeast composition. The yeast composition can be provided in an active or a semi-active form. The yeast composition can be provided in a liquid, semi-solid or dry form. In an embodiment, the yeast composition can be provided in the form of a cream yeast. In some embodiments, the process also include propagating the recombinant yeast host cell prior to the removal step. The yeast composition can be optionally stored prior to the fermentation phase. In such embodiment, the yeast composition can include, for example, one or more stabilizers or preservatives and, in some embodiment, an unfermentable carbon source (such as trehalose for example).

In some embodiments, the recombinant yeast host cell or the yeast composition obtained therefrom can be provided in a composition in combination with starch. Such composition can include additional exogenous enzyme(s) which may be used during the saccharification and/or fermentation steps.

The recombinant yeast host cells expressing the heterologous polypeptide having glucoamylase activity can be provided in a yeast product. In some embodiments, the yeast product is a yeast extract produced from recombinant yeast host cells expressing the polypeptide. The yeast extract may additionally include nutrients available to facilitate the growth of yeast cells. In some embodiments, the yeast product can be provided in a composition in combination with starch.

Example I—Screen of Heterologous Raw-Starch Digesting Glucoamylase in Recombinant Yeast Cells

TABLE 1

Genotypes of the strains used in Examples I and II. All the recombinant strains were derived from wild type *Saccharomyces cerevisiae* strain M2390 and expressed the recombinant enzyme under transcriptional control of the constitutive tef2p promoter and adh3t terminator.

| Strain name | Expressed enzyme | Enzyme description |
|---|---|---|
| M2390 | None - wild-type | *Saccharomyces cerevisiae* strain |
| M3744 | Glucoamylase AE9 (SEQ ID NO: 1) | *Saccharomycesis fibuligera* wild type glucoamylase (GA) |
| M8498 | Glucoamylase MP743 (SEQ ID NO: 2) | A40N mutation of glucoamylase AE9 |
| M14804 | Glucoamylase MP987 (SEQ ID NO: 3) | A40N, S42A, S72A triple mutation of glucoamylase AE9 |
| M17430 | Glucoamylase MP1165 (SEQ ID NO: 6) | *Penicillium oxalicum* glucoamylase |
| M4301 | Amylopullulanase AE98 (SEQ ID NO: 13) | *Thermococcus onnurineus* amylopullulanase |
| M13584 | Isopullulanase SE35 (SEQ ID NO: 14) | *Aspergillus niger* isopullulanase |

Determination of starch hydrolysis activity. Supernatant samples from 70 hours 600 µL yeast cultures were incubated with 1% (w/v) corn starch (Sigma Aldrich, cat. #S4126-2KG, batch 058K0082) in 50 mM sodium acetate, pH=5.0 for either 90 min (gel) or 20 hours (raw), at 35° C. The degree of hydrolysis was assayed spectrophotometrically at 540 nm using 3,5-dinitrosalicylic acid as a substrate.

Determination of glycogen hydrolysis activity. Supernatant samples from 53 hours 600 µL yeast cultures were incubated with 1% (w/v) glycogen in 50 mM sodium acetate, pH=5.0 for either 60 at 35° C. The degree of hydrolysis was assayed spectrophotometrically at 540 nm using 3,5-dinitrosalicylic acid as a substrate.

Determination of pullulan hydrolysis activity. Supernatant samples from 53 hours 600 µL yeast cultures were incubated with 1% (w/v) pullulan in 50 mM sodium acetate, pH=5.0 for either 60 at 35° C. The degree of hydrolysis was assayed spectrophotometrically at 540 nm using 3,5-dinitrosalicylic acid as a substrate.

Figure 3:
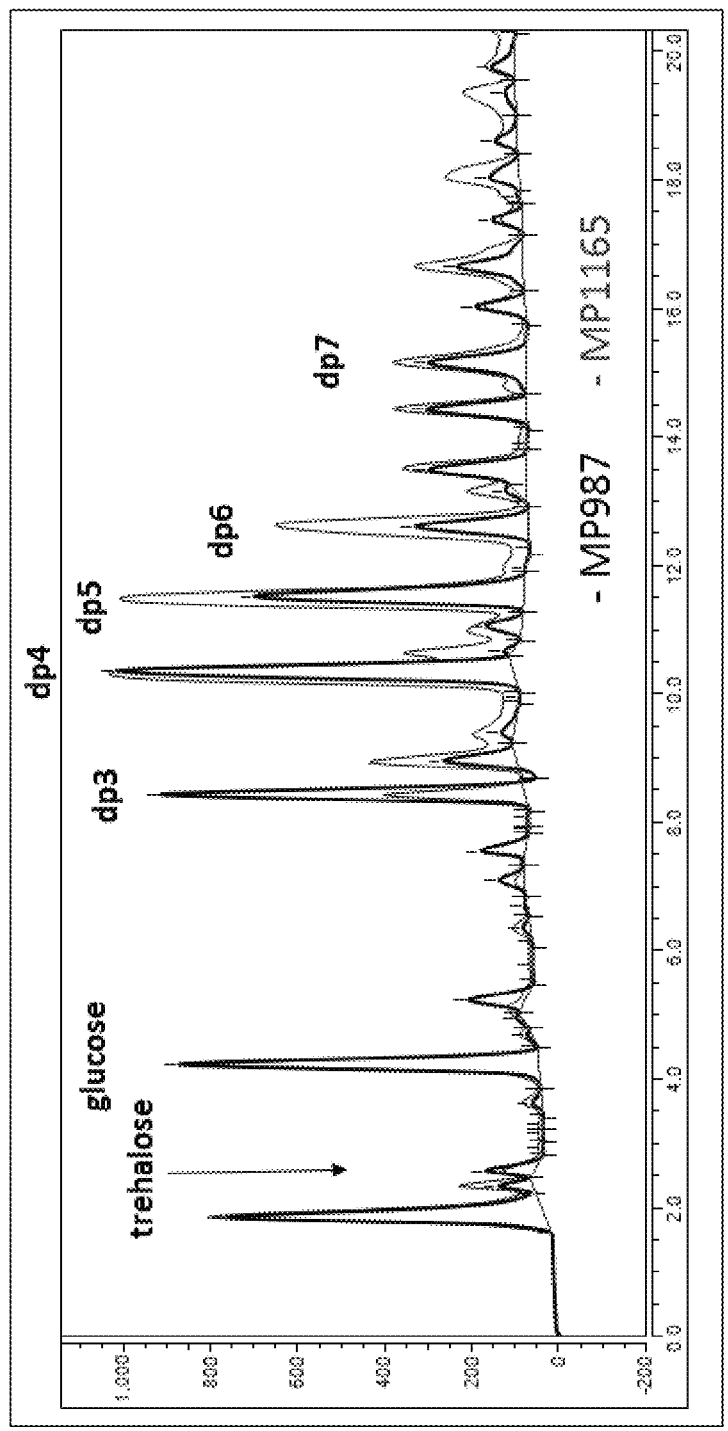
FIG. 3 illustrates the oligosaccharide profiling of corn mash incubated with glucoamylase MP987 (thick line, SEQ ID NO: 3) or MP1165 (thin line, SEQ ID NO: 6).

Oligosaccharide profiling. Filter-clarified supernatant fractions from strains M14804 and M17430 were incubated for 24 hours with corn mash in the absence of yeast (hygromycin was added to the mash to ensure no viable yeast cell were present). The carbohydrate oligomer profiles produced by the two enzymes are depicted in the chromatogram shown in FIG. 3 which was generated by High Pressure Liquid Chromatography (HPLC).

The corn starch hydrolysis efficiency and fermentation potential of the recombinantly produced and secreted MP1165 (carrier strain M17430) were compared to other glucoamylases such as MP987 (carrier strain M14804), an optimized triple mutant variant of the *Saccharomycopsis fibuligera* raw starch-digesting glucoamylse. As shown in FIG. 1, MP1165's secreted activity (carrier strain M17430) against corn starch in lab-scale tests indicated a modest advantage over MP987 (carrier strain M14804) in terms of gel starch hydrolysis (an 8.3% increase), but a substantial advantage in terms of raw starch hydrolysis levels (57.4% increase in measured activity).

The raw starch-digesting fungal glucoamylase from *Penicillium oxalicum* was identified and biochemically characterized by Xu et al. (2016). It was reported that the purified enzyme has high enzymatic activity against a number of raw starches (including corn, potato, cassava, rice, and buckwheat) and over a broad range of temperature and pH values (30-80° C. and pH=2.0-10.5, respectively).

Figure 2:
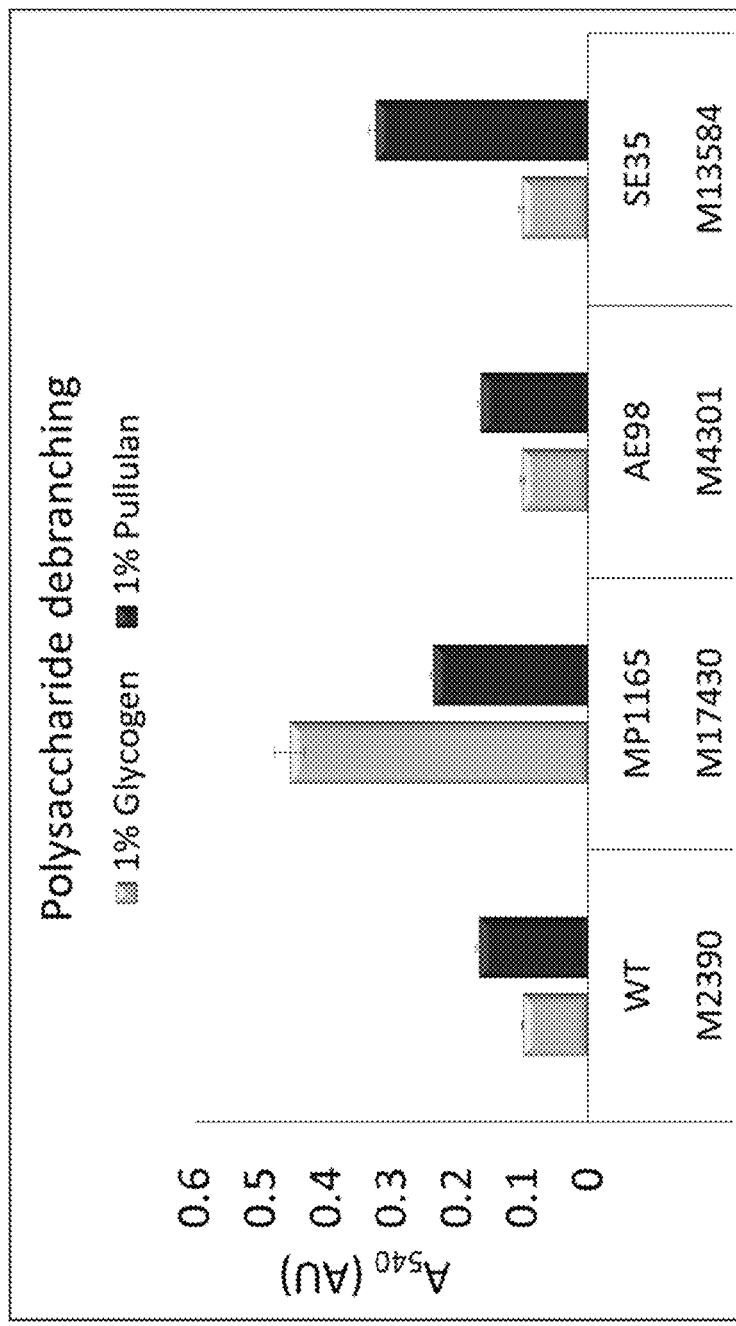
FIG. 2 illustrates polysaccharide debranching activity of various yeast strains in glycogen (left bars) and pullulan (right bars). Data is shown as absorbance at 540 nm in function of yeast strain or substrate used. Results are shown for strains M2390, M17430, M4301, and M13584. Data represent average absorbance readings of eight replicates at 540 nm of 3,5-dinitrosalicylic acid (DNS). Error bars denote standard deviation of the mean.

Furthermore as shown in FIG. 2, MP1165 (carrier strain M17430) was also shown as efficient at debranching polysaccharides such as glycogen and pullulan, at comparable or better rates than pullulanase controls which are endo-acting debranching enzymes: amylopullulanase AE98 (carrier strain M4301) and isopullulanase SE35 (carrier strain M13584). This was also supported by oligosaccharide profile differences imparted by the two secreted enzyme fractions on corn mash (see FIG. 3), with MP1165 (carrier strain M17430) releasing more oligomeric species than MP987 (carrier strain M14804) over a 24 hour time period. Only the glucoamylase-containing secreted fractions from yeast cultures were used in this assay to test their hydrolysis against corn mash.

Example II—Hydrolysis Activity and pH Sensitivity

Recombinant yeast strains expressing the *Saccharomycopsis fibuligera* glucoamylase was previously reported to maintain robustness at high temperatures (see WO2017037614, the entire content of which is incorporated herein by reference). However, during simultaneous saccharification and fermentation, low pH also presents an additional stressor to the recombinant yeast strains. Consequently, it was tested if recombinant yeast strains expressing various glucoamylases maintained their robustness during a fermentation with one or more stressors.

Corn (sterling) mash fermentation. Fermentation conditions were conducted in the presence of 33.5% total solids, 300 ppm urea, at a temperature of 33° C. (1-20 hours) and of 31° C. (20-53 hours). A purified and commercially available glucoamylase dose of 50% was used for all strains except M2390 which used a 100% glucoamylase dose. Pressure data were acquired using a pressure transducer interfacing with a computer; off-gassing from each fermentation vessel was monitored by a separate pressure channel.

Figure 4:
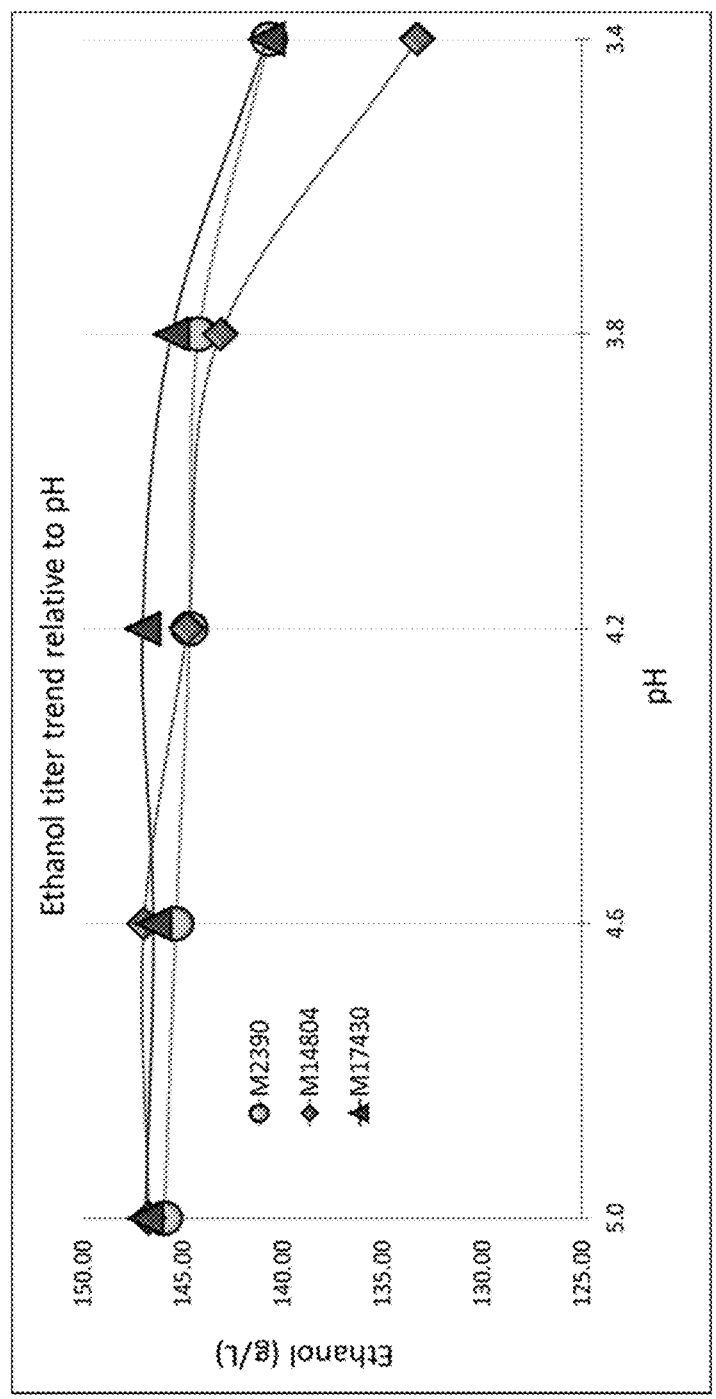
FIG. 4 illustrates corn mash fermentation endpoint data trends. Bullets represent endpoint ethanol titers for M14804 (expressing the MP987 glucoamylase) (♦ lozenges), M17430 (expressing the MP1165 glucoamylase) (▲ triangles), and M2390 the wildtype parental strain (● circles). Results are shown as the ethanol content (g/l) at five different substrate pH values: 5.0, 4.6, 4.2, 3.8, and 3.4 in function of the different strains used. Data represent averages of two replicates. Error bars denote the standard deviation of the mean.
Figure 5:
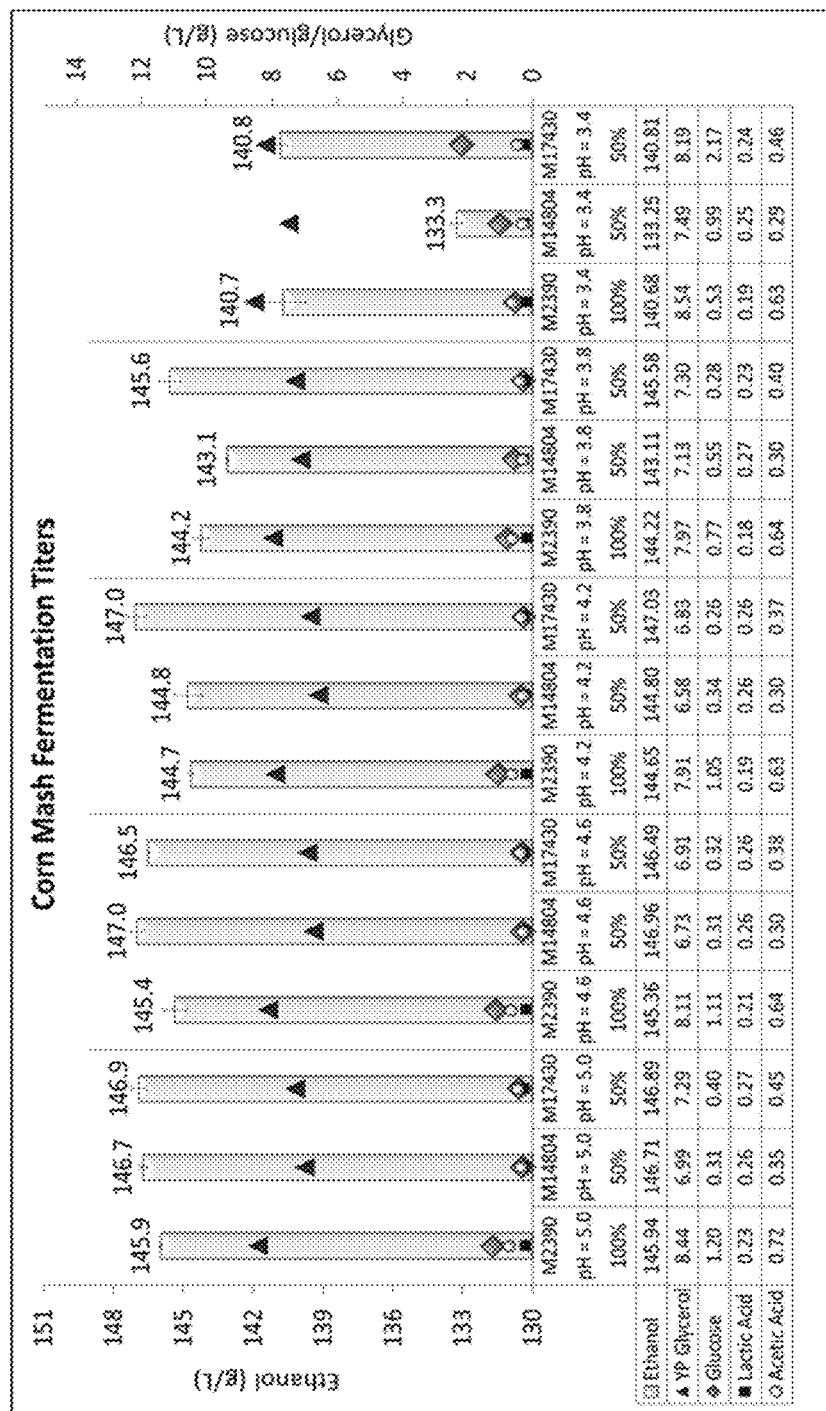
FIG. 5 illustrates corn mash fermentation endpoint titers of the fermentation presented in FIG. 4. Results are shown for M2390 (control, wild-type), M14804 (expressing the MP987 glucoamylase) and M17430 (expressing the MP1165 glucoamylase) after 53 hours of fermentation. Results are shown as ethanol (bars, left axis, in g/L), glycerol (▲ triangles, right axis, g/L), glucose (♦ lozenges, right axis, g/L), lactic acid (■ squares, right axis, g/L) and acetic acid (● circles, right axis, g/L).

The M17430 strain expressing MP1165 displayed enhanced robustness compared to other strains over an expanded pH range. This was determined in a lab-scale corn mash fermentation in which the pH of the substrate was adjusted to five distinct values within the plausible pH range which could be experienced during plant fermentations. These values are 5.0, 4.6, 4.2, 3.8, and 3.4. FIG. 4 illustrates the endpoint (53 hour) ethanol titers assessed by HPLC for MP1165 (carrier strain M17430) compared to MP987 (carrier strain M14804) and the wildtype parental background (M2390). Generally speaking, MP1165 outperformed MP987 with regard to final ethanol titers produced, particularly at lower pH values, suggesting that recombinant yeasts expressing MP987 exhibited a more pronounced pH sensitivity. Moreover, at lower pH values, the recombinant yeast expressing MP1165 achieved greater than 100% enzyme displacement when compared to M2390, which was dosed at 100% exogenous enzyme (while M14804 and M17430 were dosed with 50% exogenous enzyme). Additionally, FIG. 5 displays titers for all principal HPLC analytes, including yeast-produced glycerol and leftover glucose.

Figure 6:
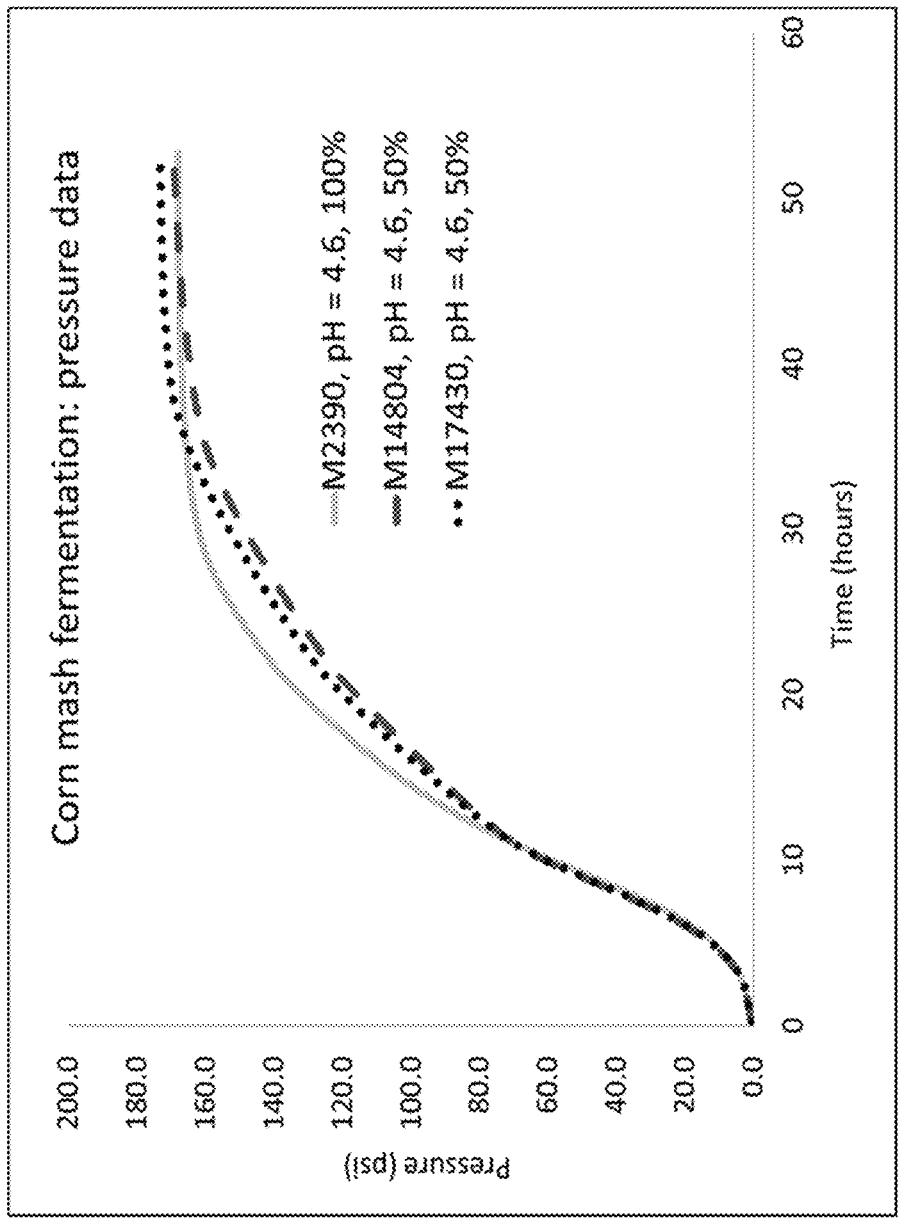
FIG. 6 illustrates pressure data recorded during the corn mash fermentation for outflowing gaseous products of the fermentation presented in FIG. 4. Pressure data are shown only at pH=4.6, for simplicity of depiction and is representative of fermentations conducted at other pH. Results are shown as pressure (measured in psi) in function of strain tested: M2390 (light grey line), M14804 (dark grey line) and M17430 (dotted line).
Figure 7:
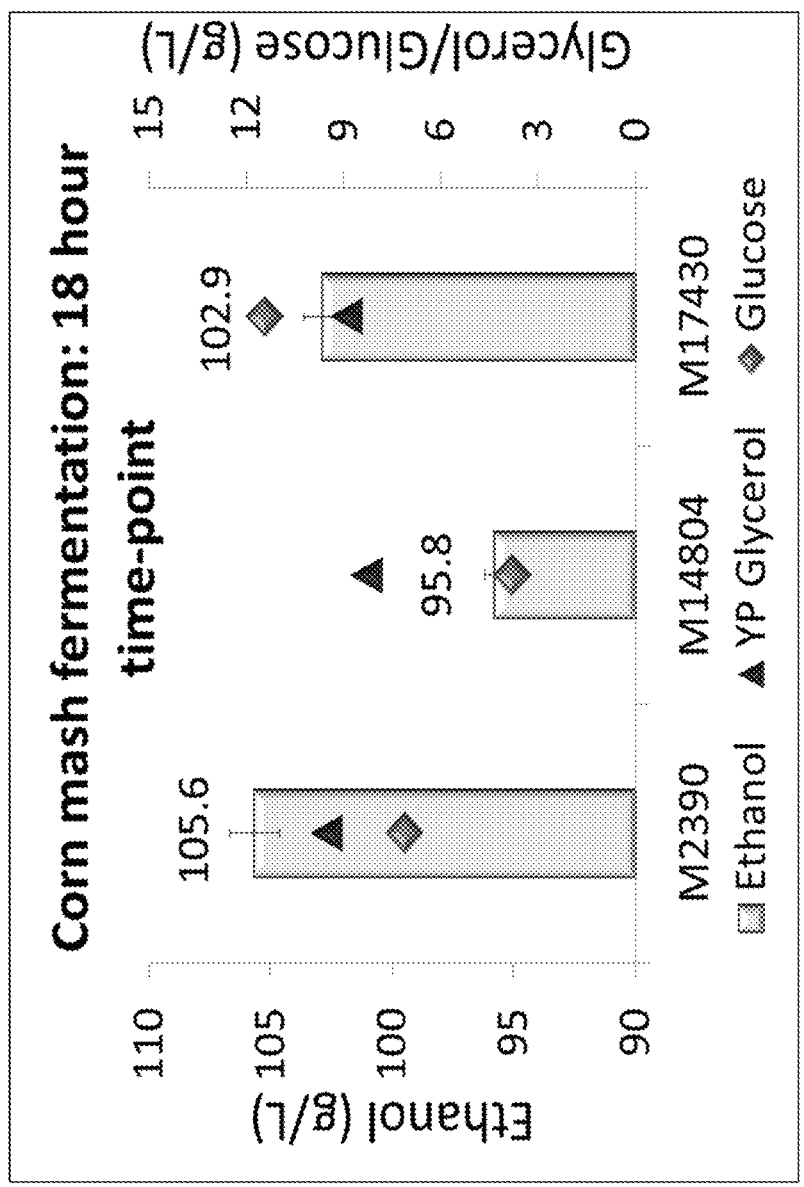
FIG. 7 illustrates corn mash fermentation midpoint sampling data. Bars represent midpoint ethanol titers sampled 18 hours into the fermentation (plotted on the left y axis, in g/L). Lozenges (♦) denote 18 hour glucose titers and triangles (▲) represent yeast-produced (YP) glycerol titers (right y axis, all in g/L). Results are shown for strains M2390, M14804 and M17430. Error bars denote the standard deviation of the mean.

In addition to endpoint HPLC analysis, the pressure of outflowing gaseous products during fermentation was monitored over time. Given that 1) every mole of glucose metabolized during ethanolic fermentation results in the net production of two moles of carbon dioxide and that 2) van der Waals real gas law dictates that the recorded pressure is directly proportional to the number of moles of gas produced, hence, the recorded pressure reports directly on the fermentative kinetics. FIG. 6 shows a representative pressure data graph from the corn mash fermentation at pH=4.6 using the same three yeast strains. The relative trends and shapes of the pressure curves were consistent for each strain at each assessed pH. Consistently, at all pH values tested, MP1165 (carrier strain M17430) fermentative pressure during this stage was higher during the consolidated bioprocessing stage than that recorded for MP987 (carrier strain M14804). This suggests 1) that M17430 appeared to impart more efficient fermentative kinetics and 2) that this phenomenon appeared to be a function of the secreted glucoamylase, MP1165. The difference in fermentative kinetics was further supported by HPLC sampling at eighteen hours into the fermentation (see FIG. 7), as illustrated by the higher ethanol titers and higher glucose titers measured for this strain during the initial stage of fermentation.

Example III—Signal Sequence Optimization

TABLE 2

Genotypes of the strains used in Example III. All the recombinant strains were derived from M2390. For recombinant strains, a single copy per chromosome was added when only a single promoter is listed and two copies per chromosome were added when two promoters are listed.

| Strain name | Promoter | Signal sequence | Expressed enzyme | Enzyme description |
|---|---|---|---|---|
| M2390 | None - wild-type *Saccharomyces cerevisiae* strain | | | |
| M17430 | tef2p | Native (SEQ ID NO: 5) | MP1165 (SEQ ID NO: 6) | *Penicillium oxalicum* glucoamylase |
| M18060 | tef2p | a mating factor (SEQ ID NO: 31) | MP1165 (SEQ ID NO: 6) | *Penicillium oxalicum* glucoamylase |
| M20175 | tef2p | Hybrid a mating factor/OST1 (SEQ ID NO: 29) | MP1165 (SEQ ID NO: 6) | *Penicillium oxalicum* glucoamylase |
| M20176 | tef2p | Hybrid a mating factor/OST1 (SEQ ID NO: 29) | MP1165 (SEQ ID NO: 6) | *Penicillium oxalicum* glucoamylase |
| M23424 | adh1p qcr8p | Hybrid a mating factor/OST1 (SEQ ID NO: 29) | MP1201 (SEQ ID NO: 19) | *Penicillium oxalicum* glucoamylase |
| M23426 | qcr8p adh 1p | Hybrid a mating factor/OST1 (SEQ ID NO: 29) | MP1201 (SEQ ID NO: 19) | *Penicillium oxalicum* glucoamylase |

First set of corn fermentations. Permissive fermentations were conducted under the following conditions: 32.5% total solids, 300 ppm urea, 33° C. (1-20 hours), 31° C. (20-52 hours), exogenous glucoamylase (GA) enzyme inclusion is listed under each bar of FIG. 8. The lactic acid challenge fermentations were conducted under the following conditions: 32.5% total solids, 0 ppm urea, 34° C. (1-52 hours), 0.38% w/v lactic acid added 20 hours into the fermentation. In the context of fermentation, secretory stress can result in a decrease in fermentative performance when environmental stressors compound the cellular stress.

Figure 8:
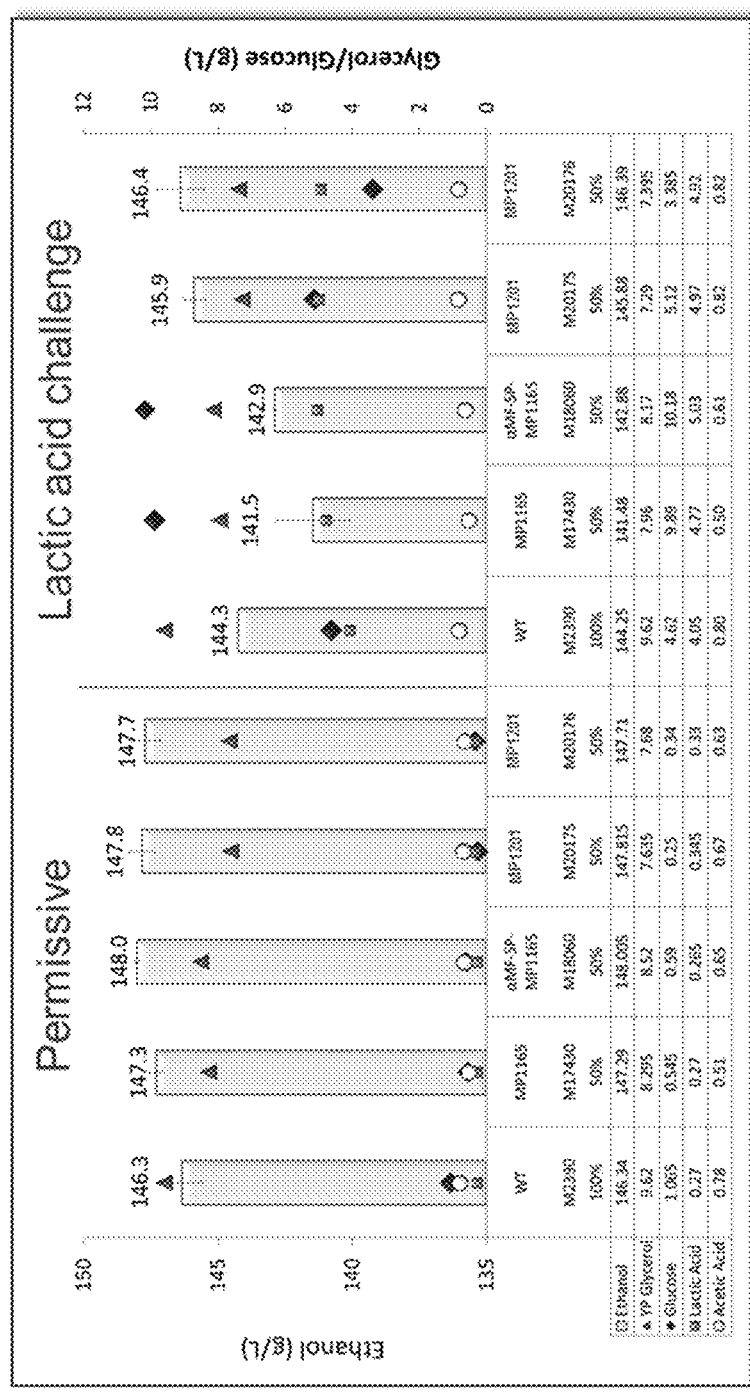
FIG. 8 illustrates corn mash fermentation drop titers in a permissive and a lactic acid challenge fermentation. Bars represent ethanol titers (plotted on the left y axis, in g/L). Lozenges (♦) denote glucose titers, triangles (▲) represent yeast-produced (YP) glycerol titers, squares (□) represent lactic acid titers and rounds (○) represent acetic acid titers (right y axis, all in g/L). Results are shown for strain M2390, M17430, M18060, M20175 and M20176. Error bars denote the standard deviation of the mean.

FIG. 8 illustrates this through the drop in ethanol production under lactic acid stress for strains M17430 and M18060, relative to permissive conditions. These strains expressed the MP1165 *P. oxalicum* glucoamylase either with its native signal peptide or with the α mating factor (αMF SP), respectively. However, when expressed with the hybrid OST1-αMF secretory signal (strains M20175 and M20176), the fermentative performance was rescued, with ethanol titers remaining close to permissive levels even under the lactic acid challenge (FIG. 8).

Figure 9:
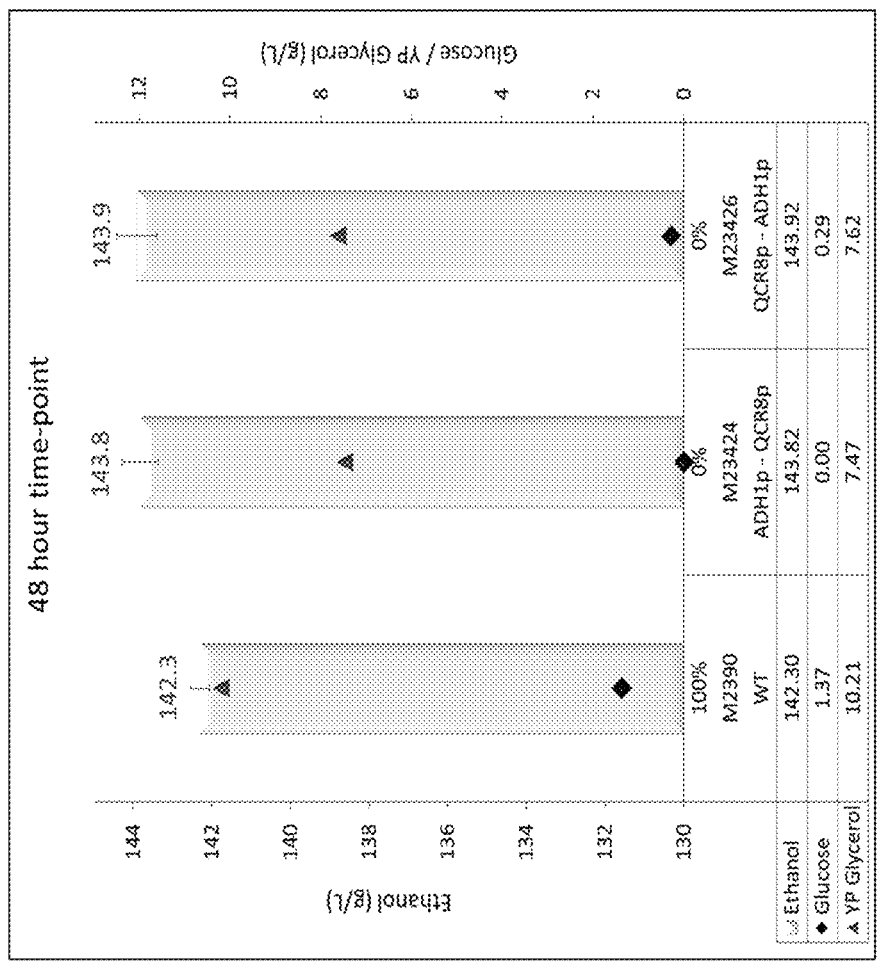
FIG. 9 illustrates corn mash fermentation drop titers in a permissive fermentation at the 48 hour time-point. Bars represent ethanol titers (plotted on the left y axis, in g/L). Lozenges (♦) denote glucose titers, triangles (▲) represent yeast-produced (YP) glycerol titers (right y axis, all in g/L). Results are shown for strain M2390, M23424 and M23426. Error bars denote the standard deviation of the mean.

Second set of corn fermentations. Permissive fermentations were conducted in lab scale fermentation under the following conditions: 32.4% total solids, 300 ppm urea, 33° C. (1-48 hours), exogenous GA enzyme inclusion is listed under each bar of FIG. 9.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Barrero J J, Casler J C, Valero F, Ferrer P, Glick B S. An improved secretion signal enhances the secretion of model proteins from *Pichia pastoris*. Microb Cell Fact. 2018 Oct. 12; 17(1):161.

Q.-S. Xu, Y.-S. Yan, J.-X. Feng, Efficient hydrolysis of raw starch and ethanol fermentation: a novel raw starch-digesting glucoamylase from *Penicillium oxalicum*, Biotechnol. Biofuels. 9 (2016) 216. doi:10.1186/S13068-016-0636-5.

What is claimed is:

1. A recombinant yeast host cell for saccharification and fermentation of a biomass, the recombinant yeast host cell having a heterologous nucleic acid molecule encoding a heterologous polypeptide having glucoamylase activity, wherein the heterologous nucleic acid molecule comprises a first polynucleotide encoding the heterologous polypeptide having glucoamylase activity, wherein the polypeptide having glucoamylase activity has an amino acid sequence that is at least 95% identical to SEQ ID NO: 6; wherein the recombinant yeast host cell is from the genus *Saccharomyces* and capable of utilizing raw starch as a substrate.

2. The recombinant yeast host cell of claim 1, further comprising a second polynucleotide encoding a signal sequence, wherein the second polynucleotide is operatively associated with the first polynucleotide.

3. The recombinant yeast host cell of claim 2, wherein the signal sequence:

has an amino acid sequence that is at least 90% identical to SEQ ID NO: 21 having signal sequence activity;

has an amino acid sequence that is at least 90% identical to SEQ ID NO: 28 having signal sequence activity;
has an amino acid sequence that is at least 90% identical to SEQ ID NO: 25 having signal sequence activity;
has an amino acid sequence that is at least 90% identical to SEQ ID NO: 27 having signal sequence activity;
has an amino acid sequence that is at least 90% identical to SEQ ID NO: 47 having signal sequence activity; or
has an amino acid sequence that is at least 90% identical to SEQ ID NO: 24 having signal sequence activity.

4. The recombinant yeast host cell of claim 3, wherein the heterologous polypeptide:
has an amino acid sequence according to SEQ ID NO: 29 having glucoamylase activity;
has an amino acid sequence according to SEQ ID NO: 5 having glucoamylase activity;
has an amino acid sequence according to SEQ ID NO: 31 having glucoamylase activity;
has an amino acid sequence according to SEQ ID NO: 43 having glucoamylase activity;
has an amino acid sequence according to SEQ ID NO: 45 having glucoamylase activity; or
has an amino acid sequence according to SEQ ID NO: 49 having glucoamylase activity.

5. The recombinant yeast host cell of claim 2, wherein the heterologous nucleic acid molecule further comprises a third polynucleotide comprising a heterologous promoter operatively associated with the first polynucleotide and the second polynucleotide allowing the expression of the heterologous polypeptide having glucoamylase activity.

6. The recombinant yeast host cell of claim 5, wherein the third polynucleotide comprises a tef2p, a adh1p and/or a qcr8p.

7. The recombinant yeast host cell of claim 1, wherein the heterologous polypeptide having glucoamylase activity is a secreted polypeptide, a membrane-associated polypeptide, and/or a tethered polypeptide.

8. The recombinant yeast host cell of claim 1 which is from species *Saccharomyces cerevisiae*.

9. A composition comprising the recombinant yeast host cell of claim 1 and raw starch.

10. A process for saccharification and fermentation of a biomass into a fermentation product, the process comprises contacting the biomass with the recombinant yeast host cell of claim 1, under a condition that allows conversion of at least a part of the biomass into the fermentation product.

11. The process of claim 10, wherein the biomass is derived from or comprises corn, potato, cassava, rice, wheat, lignocellulosic material or buckwheat.

12. The process of claim 10, wherein the biomass is derived from or comprises corn.

13. The process of claim 12, wherein the biomass comprises or is corn mash.

14. The process of claim 12, wherein the biomass comprises or is raw starch.

15. The process of claim 10, wherein the fermentation product is ethanol.

16. The process of claim 10, wherein the fermentation is conducted in the presence of a stressor comprising low pH and/or an elevated temperature.

* * * * *

SEQUENCE LISTING

<160> NUMBER OF SEQ ID NOS: 56

<210> SEQ ID NO 1
<211> LENGTH: 515
<212> TYPE: PRT
<213> ORGANISM: Saccharomycopsis fibuligera

<400> SEQUENCE: 1

Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln

```
                20                  25                  30
Ala Tyr Ser Gly Tyr Thr Val Ala Arg Ser Asn Phe Thr Gln Trp Ile
                35                  40                  45
His Glu Gln Pro Ala Val Ser Trp Tyr Tyr Leu Leu Gln Asn Ile Asp
 50                  55                  60
Tyr Pro Glu Gly Gln Phe Lys Ser Ala Lys Pro Gly Val Val Val Ala
 65                  70                  75                  80
Ser Pro Ser Thr Ser Glu Pro Asp Tyr Phe Tyr Gln Trp Thr Arg Asp
                85                  90                  95
Thr Ala Ile Thr Phe Leu Ser Leu Ile Ala Glu Val Glu Asp His Ser
                100                 105                 110
Phe Ser Asn Thr Thr Leu Ala Lys Val Val Glu Tyr Tyr Ile Ser Asn
                115                 120                 125
Thr Tyr Thr Leu Gln Arg Val Ser Asn Pro Ser Gly Asn Phe Asp Ser
                130                 135                 140
Pro Asn His Asp Gly Leu Gly Glu Pro Lys Phe Asn Val Asp Asp Thr
145                 150                 155                 160
Ala Tyr Thr Ala Ser Trp Gly Arg Pro Gln Asn Asp Gly Pro Ala Leu
                165                 170                 175
Arg Ala Tyr Ala Ile Ser Arg Tyr Leu Asn Ala Val Ala Lys His Asn
                180                 185                 190
Asn Gly Lys Leu Leu Leu Ala Gly Gln Asn Gly Ile Pro Tyr Ser Ser
                195                 200                 205
Ala Ser Asp Ile Tyr Trp Lys Ile Ile Lys Pro Asp Leu Gln His Val
                210                 215                 220
Ser Thr His Trp Ser Thr Ser Gly Phe Asp Leu Trp Glu Glu Asn Gln
225                 230                 235                 240
Gly Thr His Phe Phe Thr Ala Leu Val Gln Leu Lys Ala Leu Ser Tyr
                245                 250                 255
Gly Ile Pro Leu Ser Lys Thr Tyr Asn Asp Pro Gly Phe Thr Ser Trp
                260                 265                 270
Leu Glu Lys Gln Lys Asp Ala Leu Asn Ser Tyr Ile Asn Ser Ser Gly
                275                 280                 285
Phe Val Asn Ser Gly Lys Lys His Ile Val Glu Ser Pro Gln Leu Ser
                290                 295                 300
Ser Arg Gly Gly Leu Asp Ser Ala Thr Tyr Ile Ala Ala Leu Ile Thr
305                 310                 315                 320
His Asp Ile Gly Asp Asp Asp Thr Tyr Thr Pro Phe Asn Val Asp Asn
                325                 330                 335
Ser Tyr Val Leu Asn Ser Leu Tyr Tyr Leu Leu Val Asp Asn Lys Asn
                340                 345                 350
Arg Tyr Lys Ile Asn Gly Asn Tyr Lys Ala Gly Ala Ala Val Gly Arg
                355                 360                 365
Tyr Pro Glu Asp Val Tyr Asn Gly Val Gly Thr Ser Glu Gly Asn Pro
                370                 375                 380
Trp Gln Leu Ala Thr Ala Tyr Ala Gly Gln Thr Phe Tyr Thr Leu Ala
385                 390                 395                 400
Tyr Asn Ser Leu Lys Asn Lys Lys Asn Leu Val Ile Glu Lys Leu Asn
                405                 410                 415
Tyr Asp Leu Tyr Asn Ser Phe Ile Ala Asp Leu Ser Lys Ile Asp Ser
                420                 425                 430
Ser Tyr Ala Ser Lys Asp Ser Leu Thr Leu Thr Tyr Gly Ser Asp Asn
                435                 440                 445
```

Tyr Lys Asn Val Ile Lys Ser Leu Leu Gln Phe Gly Asp Ser Phe Leu
450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515

<210> SEQ ID NO 2
<211> LENGTH: 515
<212> TYPE: PRT
<213> ORGANISM: Artificial Sequence
<220> FEATURE:
<223> OTHER INFORMATION: A40N mutation of SEQ ID NO: 1

<400> SEQUENCE: 2

Met Ile Arg Leu Thr Val Phe Ser Thr Ala Val Ile Ala Ala Val Ala
1               5                   10                  15

Ser Cys Val Pro Val Glu Leu Asp Lys Arg Asn Thr Gly His Phe Gln
                20                  25                  30

Ala Tyr Ser Asn Tyr Thr Val Ala Arg Ser Asn Phe Thr Gln Trp Ile
            35                  40                  45

His Glu Gln Pro Ala Val Ser Trp Tyr Tyr Leu Leu Gln Asn Ile Asp
        50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Leu Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
        210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                245                 250                 255

Gly Ile Pro Leu Ser Lys Thr Tyr Asn Asp Pro Gly Phe Thr Ser Trp
            260                 265                 270

Leu Glu Lys Gln Glu Asp Ala Leu Asn Ser Tyr Ile Asn Ser Ser Gly
        275                 280                 285

```
Phe Val Asn Ser Gly Lys Lys His Ile Val Glu Ser Pro Gln Leu Ser
            290                 295                 300

Ser Arg Gly Gly Leu Asp Ser Ala Thr Tyr Ile Ala Ala Leu Ile Thr
305                 310                 315                 320

His Asp Ile Gly Asp Asp Thr Tyr Thr Pro Phe Asn Val Asp Asn
                325                 330                 335

Ser Tyr Val Leu Asn Ser Leu Tyr Tyr Leu Val Asp Asn Lys Asn
            340                 345                 350

Arg Tyr Lys Ile Asn Gly Asn Tyr Lys Ala Gly Ala Val Gly Arg
            355                 360                 365

Tyr Pro Glu Asp Val Tyr Asn Gly Val Gly Thr Ser Glu Gly Asn Pro
            370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Asn Leu Val Ile Glu Lys Leu Asn
                405                 410                 415

Tyr Asp Leu Tyr Asn Ser Phe Ile Ala Asp Leu Ser Lys Ile Asp Ser
                420                 425                 430

Ser Tyr Ala Ser Lys Asp Ser Leu Thr Leu Thr Tyr Gly Ser Asp Asn
            435                 440                 445

Tyr Lys Asn Val Ile Lys Ser Leu Leu Gln Phe Gly Asp Ser Phe Leu
            450                 455                 460

Lys Val Leu Leu Asp His Ile Asp Asp Asn Gly Gln Leu Thr Glu Glu
465                 470                 475                 480

Ile Asn Arg Tyr Thr Gly Ile Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515

<210> SEQ ID NO 3
<211> LENGTH: 515
<212> TYPE: PRT
<213> ORGANISM: Artificial Sequence
<220> FEATURE:
<223> OTHER INFORMATION: A40N, S42A, S72A triple mutation of SEQ ID NO:
      1

<400> SEQUENCE: 3

Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
                20                  25                  30

Ala Tyr Ser Gly Tyr Thr Val Asn Arg Ala Asn Phe Thr Gln Trp Ile
            35                  40                  45

His Glu Gln Pro Ala Val Ser Trp Tyr Tyr Leu Leu Gln Asn Ile Asp
        50                  55                  60

Tyr Pro Glu Gly Gln Phe Lys Ala Ala Lys Pro Gly Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
                100                 105                 110

Phe Ser Asn Thr Thr Leu Ala Lys Val Val Glu Tyr Tyr Ile Ser Asn
```

```
            115                 120                 125
Thr Tyr Thr Leu Gln Arg Val Ser Asn Pro Ser Gly Asn Phe Asp Ser
130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                245                 250                 255

Gly Ile Pro Leu Ser Lys Thr Tyr Asn Asp Pro Gly Phe Thr Ser Trp
            260                 265                 270

Leu Glu Lys Gln Lys Asp Ala Leu Asn Ser Tyr Ile Asn Ser Ser Gly
        275                 280                 285

Phe Val Asn Ser Gly Lys Lys His Ile Val Glu Ser Pro Gln Leu Ser
290                 295                 300

Ser Arg Gly Gly Leu Asp Ser Ala Thr Tyr Ile Ala Ala Leu Ile Thr
305                 310                 315                 320

His Asp Ile Gly Asp Asp Asp Thr Tyr Thr Pro Phe Asn Val Asp Asn
                325                 330                 335

Ser Tyr Val Leu Asn Ser Leu Tyr Tyr Leu Leu Val Asp Asn Lys Asn
            340                 345                 350

Arg Tyr Lys Ile Asn Gly Asn Tyr Lys Ala Gly Ala Val Gly Arg
        355                 360                 365

Tyr Pro Glu Asp Val Tyr Asn Gly Val Gly Thr Ser Glu Gly Asn Pro
370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Asn Leu Val Ile Glu Lys Leu Asn
                405                 410                 415

Tyr Asp Leu Tyr Asn Ser Phe Ile Ala Asp Leu Ser Lys Ile Asp Ser
            420                 425                 430

Ser Tyr Ala Ser Lys Asp Ser Leu Thr Leu Thr Tyr Gly Ser Asp Asn
        435                 440                 445

Tyr Lys Asn Val Ile Lys Ser Leu Leu Gln Phe Gly Asp Ser Phe Leu
450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515

<210> SEQ ID NO 4
```

```
<211> LENGTH: 1908
<212> TYPE: DNA
<213> ORGANISM: Penicillium oxalicum
<220> FEATURE:
<221> NAME/KEY: CDS
<222> LOCATION: (1)..(1908)

<400> SEQUENCE: 4 atg tcc agg ttg ttg tat gct ttg ggt gct ttg gct gtt ggt caa tct        48
Met Ser Arg Leu Leu Tyr Ala Leu Gly Ala Leu Ala Val Gly Gln Ser
1               5                   10                  15 gct tta gct gct cca caa ttg tct cca aga gct act tct ttg gat tct        96
Ala Leu Ala Ala Pro Gln Leu Ser Pro Arg Ala Thr Ser Leu Asp Ser
                20                  25                  30 tgg ttg tca tct gaa acc acc ttt tct ttg aac ggt atc ttg gct aat       144
Trp Leu Ser Ser Glu Thr Thr Phe Ser Leu Asn Gly Ile Leu Ala Asn
            35                  40                  45 atc ggt tct tct ggt gct tac tct aaa tct gct gct tca ggt gct gtt       192
Ile Gly Ser Ser Gly Ala Tyr Ser Lys Ser Ala Ala Ser Gly Ala Val
        50                  55                  60 att gct tct cca tct act tct aat cca gac tac tat tac act tgg act       240
Ile Ala Ser Pro Ser Thr Ser Asn Pro Asp Tyr Tyr Tyr Thr Trp Thr
65                  70                  75                  80 aga gat gct gct ttg act ttg aaa gct ttg gtt gac att ttc cgt aat       288
Arg Asp Ala Ala Leu Thr Leu Lys Ala Leu Val Asp Ile Phe Arg Asn
                85                  90                  95 ggt aac ttg ggc ttg caa acc gtt att gaa caa tac gtt aat gcc caa       336
Gly Asn Leu Gly Leu Gln Thr Val Ile Glu Gln Tyr Val Asn Ala Gln
                100                 105                 110 gct aag ttg caa act gtt tca aat cca tct ggt ggt ttg tct gat ggt       384
Ala Lys Leu Gln Thr Val Ser Asn Pro Ser Gly Gly Leu Ser Asp Gly
            115                 120                 125 gct ggt ttg ggt gaa cct aag ttt aat gtt gat ttg tct gct ttc act       432
Ala Gly Leu Gly Glu Pro Lys Phe Asn Val Asp Leu Ser Ala Phe Thr
        130                 135                 140 ggt gct tgg ggt aga cca caa aga gat ggt cca gct ttg aga gct att       480
Gly Ala Trp Gly Arg Pro Gln Arg Asp Gly Pro Ala Leu Arg Ala Ile
145                 150                 155                 160 gct ttg att gat ttt ggc aac tgg ttg atc gat aac ggc tac aaa tct       528
Ala Leu Ile Asp Phe Gly Asn Trp Leu Ile Asp Asn Gly Tyr Lys Ser
                165                 170                 175 tac gct gtt aac aat gtt tgg ccc atc gtt aga aat gat ttg gct tat       576
Tyr Ala Val Asn Asn Val Trp Pro Ile Val Arg Asn Asp Leu Ala Tyr
                180                 185                 190 gtt gct cag tac tgg tcc caa tct ggt ttt gat ttg tgg gaa gaa gtc       624
Val Ala Gln Tyr Trp Ser Gln Ser Gly Phe Asp Leu Trp Glu Glu Val
            195                 200                 205 aac tcc atg tct ttt ttc acc gtt gcc aat caa cac aga tca ttg gtt       672
Asn Ser Met Ser Phe Phe Thr Val Ala Asn Gln His Arg Ser Leu Val
        210                 215                 220 gaa ggt tct gct ttt gct tct aga gtt ggt gct tct tgt tct ggt tgt       720
Glu Gly Ser Ala Phe Ala Ser Arg Val Gly Ala Ser Cys Ser Gly Cys
225                 230                 235                 240 gat tct caa gct cca caa att ttg tgc tac atg caa tct ttt tgg acc       768
Asp Ser Gln Ala Pro Gln Ile Leu Cys Tyr Met Gln Ser Phe Trp Thr
                245                 250                 255 ggc tct tac att aac gct aat act ggt ggt ggt aga tct ggt aaa gat       816
Gly Ser Tyr Ile Asn Ala Asn Thr Gly Gly Gly Arg Ser Gly Lys Asp
                260                 265                 270 tcc aac act att ttg gcc tcc att cat act ttt gat cca gct gct tca       864
Ser Asn Thr Ile Leu Ala Ser Ile His Thr Phe Asp Pro Ala Ala Ser
```

```
            275                 280                 285
tgt gat gat gtt act ttt caa cca tgt tcc tct aga gct ttg gct aac    912
Cys Asp Asp Val Thr Phe Gln Pro Cys Ser Ser Arg Ala Leu Ala Asn
    290                 295                 300 cat aag gtt tac acc gat tct ttc aga tcc gtt tac gct ttg aat tcc    960
His Lys Val Tyr Thr Asp Ser Phe Arg Ser Val Tyr Ala Leu Asn Ser
305                 310                 315                 320 ggt att gct caa ggt aaa gct gtt tct gtt ggt aga tat cca gag gat   1008
Gly Ile Ala Gln Gly Lys Ala Val Ser Val Gly Arg Tyr Pro Glu Asp
            325                 330                 335 tct tac tat ggt ggt aat cca tgg ttc ttg tct aat ttg gct gct gct   1056
Ser Tyr Tyr Gly Gly Asn Pro Trp Phe Leu Ser Asn Leu Ala Ala Ala
                340                 345                 350 gaa caa tta tac gat gca atc tac caa tgg aac aag atc ggt tcc att   1104
Glu Gln Leu Tyr Asp Ala Ile Tyr Gln Trp Asn Lys Ile Gly Ser Ile
                    355                 360                 365 act att acc tct acc tct ttg gct ttc ttc aag gat gtt tat cca tca   1152
Thr Ile Thr Ser Thr Ser Leu Ala Phe Phe Lys Asp Val Tyr Pro Ser
370                 375                 380 gct gct act ggt act tat gct tct ggt tct act act ttc aac gcc att   1200
Ala Ala Thr Gly Thr Tyr Ala Ser Gly Ser Thr Thr Phe Asn Ala Ile
385                 390                 395                 400 att tct gct gtt aag act tac gct gat ggc tac gtt tct atc gtt caa   1248
Ile Ser Ala Val Lys Thr Tyr Ala Asp Gly Tyr Val Ser Ile Val Gln
                405                 410                 415 tct cat tct tac gcc aac ggt tct ttg tcc gaa caa ttt gat aga act   1296
Ser His Ser Tyr Ala Asn Gly Ser Leu Ser Glu Gln Phe Asp Arg Thr
            420                 425                 430 acc ggc ttg tct att tcc gct aga gat ttg act tgg tct tat gca gct   1344
Thr Gly Leu Ser Ile Ser Ala Arg Asp Leu Thr Trp Ser Tyr Ala Ala
                435                 440                 445 ttg ttg act gcc aat gat aga aga aat ggt gtt gtt cct cct tct tgg   1392
Leu Leu Thr Ala Asn Asp Arg Arg Asn Gly Val Val Pro Pro Ser Trp
450                 455                 460 ggt gct tca tct gct aat tct att cca ggt tca tgt tct atg ggt tct   1440
Gly Ala Ser Ser Ala Asn Ser Ile Pro Gly Ser Cys Ser Met Gly Ser
465                 470                 475                 480 gct aca ggt tct tac gct act cca tca gtt ggt tct tgg cca gct act   1488
Ala Thr Gly Ser Tyr Ala Thr Pro Ser Val Gly Ser Trp Pro Ala Thr
                485                 490                 495 ttg act tct ggt act gct gct cca tct tct act tca act act aca aaa   1536
Leu Thr Ser Gly Thr Ala Ala Pro Ser Ser Thr Ser Thr Thr Thr Lys
            500                 505                 510 gct cca act acc act act gct act aca act aca tct gct ggt tca tgt   1584
Ala Pro Thr Thr Thr Thr Ala Thr Thr Thr Thr Ser Ala Gly Ser Cys
                515                 520                 525 act act cca act gct gtt gct gtt act ttc gac gaa att gct act act   1632
Thr Thr Pro Thr Ala Val Ala Val Thr Phe Asp Glu Ile Ala Thr Thr
530                 535                 540 acc ttc ggt gaa aac gtt tac ttg gtt ggt tcc atc tct caa tta ggt   1680
Thr Phe Gly Glu Asn Val Tyr Leu Val Gly Ser Ile Ser Gln Leu Gly
545                 550                 555                 560 aat tgg aat act gcc aac ggt att cca tta tcc gct tct aag tac act   1728
Asn Trp Asn Thr Ala Asn Gly Ile Pro Leu Ser Ala Ser Lys Tyr Thr
                565                 570                 575 tct tct aac cca ttg tgg tac gct act gtt aat ttg cca gct ggt act   1776
Ser Ser Asn Pro Leu Trp Tyr Ala Thr Val Asn Leu Pro Ala Gly Thr
            580                 585                 590 act ttt cag tac aag tac ttc aga aaa gag tcc gac ggt tct att aag   1824
```

```
Thr Phe Gln Tyr Lys Tyr Phe Arg Lys Glu Ser Asp Gly Ser Ile Lys
            595                 600                 605 tgg gaa tct gat cca aac aga tct tac act gtt cca gct aaa tgt ggt    1872
Trp Glu Ser Asp Pro Asn Arg Ser Tyr Thr Val Pro Ala Lys Cys Gly
610                 615                 620 act aca acc gct act gaa aat gac act tgg aga tga                    1908
Thr Thr Thr Ala Thr Glu Asn Asp Thr Trp Arg
625                 630                 635

<210> SEQ ID NO 5
<211> LENGTH: 635
<212> TYPE: PRT
<213> ORGANISM: Penicillium oxalicum

<400> SEQUENCE: 5

Met Ser Arg Leu Leu Tyr Ala Leu Gly Ala Leu Ala Val Gly Gln Ser
1               5                   10                  15

Ala Leu Ala Ala Pro Gln Leu Ser Pro Arg Ala Thr Ser Leu Asp Ser
            20                  25                  30

Trp Leu Ser Ser Glu Thr Thr Phe Ser Leu Asn Gly Ile Leu Ala Asn
        35                  40                  45

Ile Gly Ser Ser Gly Ala Tyr Ser Lys Ser Ala Ala Ser Gly Ala Val
    50                  55                  60

Ile Ala Ser Pro Ser Thr Ser Asn Pro Asp Tyr Tyr Tyr Thr Trp Thr
65                  70                  75                  80

Arg Asp Ala Ala Leu Thr Leu Lys Ala Leu Val Asp Ile Phe Arg Asn
                85                  90                  95

Gly Asn Leu Gly Leu Gln Thr Val Ile Glu Gln Tyr Val Asn Ala Gln
            100                 105                 110

Ala Lys Leu Gln Thr Val Ser Asn Pro Ser Gly Gly Leu Ser Asp Gly
        115                 120                 125

Ala Gly Leu Gly Glu Pro Lys Phe Asn Val Asp Leu Ser Ala Phe Thr
    130                 135                 140

Gly Ala Trp Gly Arg Pro Gln Arg Asp Gly Pro Ala Leu Arg Ala Ile
145                 150                 155                 160

Ala Leu Ile Asp Phe Gly Asn Trp Leu Ile Asp Asn Gly Tyr Lys Ser
                165                 170                 175

Tyr Ala Val Asn Asn Val Trp Pro Ile Val Arg Asn Asp Leu Ala Tyr
            180                 185                 190

Val Ala Gln Tyr Trp Ser Gln Ser Gly Phe Asp Leu Trp Glu Glu Val
        195                 200                 205

Asn Ser Met Ser Phe Phe Thr Val Ala Asn Gln His Arg Ser Leu Val
    210                 215                 220

Glu Gly Ser Ala Phe Ala Ser Arg Val Gly Ala Ser Cys Ser Gly Cys
225                 230                 235                 240

Asp Ser Gln Ala Pro Gln Ile Leu Cys Tyr Met Gln Ser Phe Trp Thr
                245                 250                 255

Gly Ser Tyr Ile Asn Ala Asn Thr Gly Gly Arg Ser Gly Lys Asp
            260                 265                 270

Ser Asn Thr Ile Leu Ala Ser Ile His Thr Phe Asp Pro Ala Ala Ser
        275                 280                 285

Cys Asp Asp Val Thr Phe Gln Pro Cys Ser Arg Ala Leu Ala Asn
    290                 295                 300

His Lys Val Tyr Thr Asp Ser Phe Arg Ser Val Tyr Ala Leu Asn Ser
305                 310                 315                 320
```

Gly Ile Ala Gln Gly Lys Ala Val Ser Val Gly Arg Tyr Pro Glu Asp
            325                 330                 335

Ser Tyr Tyr Gly Gly Asn Pro Trp Phe Leu Ser Asn Leu Ala Ala Ala
        340                 345                 350

Glu Gln Leu Tyr Asp Ala Ile Tyr Gln Trp Asn Lys Ile Gly Ser Ile
    355                 360                 365

Thr Ile Thr Ser Thr Ser Leu Ala Phe Phe Lys Asp Val Tyr Pro Ser
370                 375                 380

Ala Ala Thr Gly Thr Tyr Ala Ser Gly Ser Thr Phe Asn Ala Ile
385                 390                 395                 400

Ile Ser Ala Val Lys Thr Tyr Ala Asp Gly Tyr Val Ser Ile Val Gln
                405                 410                 415

Ser His Ser Tyr Ala Asn Gly Ser Leu Ser Glu Gln Phe Asp Arg Thr
            420                 425                 430

Thr Gly Leu Ser Ile Ser Ala Arg Asp Leu Thr Trp Ser Tyr Ala Ala
        435                 440                 445

Leu Leu Thr Ala Asn Asp Arg Asn Gly Val Pro Pro Ser Trp
    450                 455                 460

Gly Ala Ser Ser Ala Asn Ser Ile Pro Gly Ser Cys Ser Met Gly Ser
465                 470                 475                 480

Ala Thr Gly Ser Tyr Ala Thr Pro Ser Val Gly Ser Trp Pro Ala Thr
                485                 490                 495

Leu Thr Ser Gly Thr Ala Ala Pro Ser Ser Thr Ser Thr Thr Thr Lys
            500                 505                 510

Ala Pro Thr Thr Thr Thr Ala Thr Thr Thr Ser Ala Gly Ser Cys
        515                 520                 525

Thr Thr Pro Thr Ala Val Ala Val Thr Phe Asp Glu Ile Ala Thr Thr
530                 535                 540

Thr Phe Gly Glu Asn Val Tyr Leu Val Gly Ser Ile Ser Gln Leu Gly
545                 550                 555                 560

Asn Trp Asn Thr Ala Asn Gly Ile Pro Leu Ser Ala Ser Lys Tyr Thr
                565                 570                 575

Ser Ser Asn Pro Leu Trp Tyr Ala Thr Val Asn Leu Pro Ala Gly Thr
            580                 585                 590

Thr Phe Gln Tyr Lys Tyr Phe Arg Lys Glu Ser Asp Gly Ser Ile Lys
        595                 600                 605

Trp Glu Ser Asp Pro Asn Arg Ser Tyr Thr Val Pro Ala Lys Cys Gly
    610                 615                 620

Thr Thr Thr Ala Thr Glu Asn Asp Thr Trp Arg
625                 630                 635

<210> SEQ ID NO 6
<211> LENGTH: 616
<212> TYPE: PRT
<213> ORGANISM: Penicillium oxalicum

<400> SEQUENCE: 6

Ala Pro Gln Leu Ser Pro Arg Ala Thr Ser Leu Asp Ser Trp Leu Ser
1               5                   10                  15

Ser Glu Thr Thr Phe Ser Leu Asn Gly Ile Leu Ala Asn Ile Gly Ser
            20                  25                  30

Ser Gly Ala Tyr Ser Lys Ser Ala Ala Ser Gly Ala Val Ile Ala Ser
        35                  40                  45

Pro Ser Thr Ser Asn Pro Asp Tyr Tyr Thr Trp Thr Arg Asp Ala
    50                  55                  60

```
Ala Leu Thr Leu Lys Ala Leu Val Asp Ile Phe Arg Asn Gly Asn Leu
 65                  70                  75                  80

Gly Leu Gln Thr Val Ile Glu Gln Tyr Val Asn Ala Gln Ala Lys Leu
                 85                  90                  95

Gln Thr Val Ser Asn Pro Ser Gly Gly Leu Ser Asp Gly Ala Gly Leu
            100                 105                 110

Gly Glu Pro Lys Phe Asn Val Asp Leu Ser Ala Phe Thr Gly Ala Trp
        115                 120                 125

Gly Arg Pro Gln Arg Asp Gly Pro Ala Leu Arg Ala Ile Ala Leu Ile
130                 135                 140

Asp Phe Gly Asn Trp Leu Ile Asp Asn Gly Tyr Lys Ser Tyr Ala Val
145                 150                 155                 160

Asn Asn Val Trp Pro Ile Val Arg Asn Asp Leu Ala Tyr Val Ala Gln
                165                 170                 175

Tyr Trp Ser Gln Ser Gly Phe Asp Leu Trp Glu Val Asn Ser Met
            180                 185                 190

Ser Phe Phe Thr Val Ala Asn Gln His Arg Ser Leu Val Glu Gly Ser
        195                 200                 205

Ala Phe Ala Ser Arg Val Gly Ala Ser Cys Ser Gly Cys Asp Ser Gln
210                 215                 220

Ala Pro Gln Ile Leu Cys Tyr Met Gln Ser Phe Trp Thr Gly Ser Tyr
225                 230                 235                 240

Ile Asn Ala Asn Thr Gly Gly Arg Ser Gly Lys Asp Ser Asn Thr
                245                 250                 255

Ile Leu Ala Ser Ile His Thr Phe Asp Pro Ala Ala Ser Cys Asp Asp
            260                 265                 270

Val Thr Phe Gln Pro Cys Ser Ser Arg Ala Leu Ala Asn His Lys Val
        275                 280                 285

Tyr Thr Asp Ser Phe Arg Ser Val Tyr Ala Leu Asn Ser Gly Ile Ala
290                 295                 300

Gln Gly Lys Ala Val Ser Val Gly Arg Tyr Pro Glu Asp Ser Tyr Tyr
305                 310                 315                 320

Gly Gly Asn Pro Trp Phe Leu Ser Asn Leu Ala Ala Ala Glu Gln Leu
                325                 330                 335

Tyr Asp Ala Ile Tyr Gln Trp Asn Lys Ile Gly Ser Ile Thr Ile Thr
            340                 345                 350

Ser Thr Ser Leu Ala Phe Phe Lys Asp Val Tyr Pro Ser Ala Ala Thr
        355                 360                 365

Gly Thr Tyr Ala Ser Gly Ser Thr Thr Phe Asn Ala Ile Ile Ser Ala
370                 375                 380

Val Lys Thr Tyr Ala Asp Gly Tyr Val Ser Ile Val Gln Ser His Ser
385                 390                 395                 400

Tyr Ala Asn Gly Ser Leu Ser Glu Gln Phe Asp Arg Thr Thr Gly Leu
                405                 410                 415

Ser Ile Ser Ala Arg Asp Leu Thr Trp Ser Tyr Ala Ala Leu Leu Thr
            420                 425                 430

Ala Asn Asp Arg Arg Asn Gly Val Val Pro Pro Ser Trp Gly Ala Ser
        435                 440                 445

Ser Ala Asn Ser Ile Pro Gly Ser Cys Ser Met Gly Ser Ala Thr Gly
450                 455                 460

Ser Tyr Ala Thr Pro Ser Val Gly Ser Trp Pro Ala Thr Leu Thr Ser
465                 470                 475                 480
```

```
Gly Thr Ala Ala Pro Ser Ser Thr Ser Thr Thr Lys Ala Pro Thr
                485             490             495

Thr Thr Thr Ala Thr Thr Thr Ser Ala Gly Ser Cys Thr Thr Pro
            500             505             510

Thr Ala Val Ala Val Thr Phe Asp Glu Ile Ala Thr Thr Phe Gly
        515             520             525

Glu Asn Val Tyr Leu Val Gly Ser Ile Ser Gln Leu Gly Asn Trp Asn
    530             535             540

Thr Ala Asn Gly Ile Pro Leu Ser Ala Ser Lys Tyr Thr Ser Ser Asn
545             550             555             560

Pro Leu Trp Tyr Ala Thr Val Asn Leu Pro Ala Gly Thr Thr Phe Gln
                565             570             575

Tyr Lys Tyr Phe Arg Lys Glu Ser Asp Gly Ser Ile Lys Trp Glu Ser
            580             585             590

Asp Pro Asn Arg Ser Tyr Thr Val Pro Ala Lys Cys Gly Thr Thr Thr
            595             600             605

Ala Thr Glu Asn Asp Thr Trp Arg
    610             615
```

<210> SEQ ID NO 7
<211> LENGTH: 633
<212> TYPE: PRT
<213> ORGANISM: Bacillus amyloliquefaciens

<400> SEQUENCE: 7

```
Gly Pro Ala Ala Ala Asn Ala Glu Thr Ala Asn Lys Ser Asn Lys Val
1               5                   10                  15

Thr Ala Ser Ser Val Lys Asn Gly Thr Ile Leu His Ala Trp Asn Trp
                20                  25                  30

Ser Phe Asn Thr Leu Thr Gln Asn Met Lys Asp Ile Arg Asp Ala Gly
            35                  40                  45

Tyr Ala Ala Ile Gln Thr Ser Pro Ile Asn Gln Val Lys Glu Gly Asn
        50                  55                  60

Gln Gly Asp Lys Ser Met Arg Asn Trp Tyr Trp Leu Tyr Gln Pro Thr
65              70                  75                  80

Ser Tyr Gln Ile Gly Asn Arg Tyr Leu Gly Thr Glu Gln Glu Phe Lys
                85                  90                  95

Asp Met Cys Ala Ala Glu Lys Tyr Gly Val Lys Val Ile Val Asp
            100                 105                 110

Ala Val Ile Asn His Thr Thr Ser Asp Tyr Gly Ala Ile Ser Asp Glu
        115                 120                 125

Ile Lys Arg Ile Pro Asn Trp Thr His Gly Asn Thr Gln Ile Lys Asn
    130                 135                 140

Trp Ser Asp Arg Trp Asp Val Thr Gln Asn Ser Leu Leu Gly Leu Tyr
145                 150                 155                 160

Asp Trp Asn Thr Gln Asn Thr Glu Val Gln Val Tyr Leu Lys Arg Phe
                165                 170                 175

Leu Glu Arg Ala Leu Asn Asp Gly Ala Asp Gly Phe Arg Tyr Asp Ala
            180                 185                 190

Ala Lys His Ile Glu Leu Pro Asp Asp Gly Asn Tyr Gly Ser Gln Phe
        195                 200                 205

Trp Pro Asn Ile Thr Asn Thr Ser Ala Glu Phe Gln Tyr Gly Glu Ile
    210                 215                 220

Leu Gln Asp Ser Ala Ser Arg Asp Thr Ala Tyr Ala Asn Tyr Met Asn
225                 230                 235                 240
```

-continued

Val Thr Ala Ser Asn Tyr Gly His Ser Ile Arg Ser Ala Leu Lys Asn
            245                 250                 255

Arg Asn Leu Ser Val Ser Asn Ile Ser His Tyr Ala Ser Asp Val Ser
            260                 265                 270

Ala Asp Lys Leu Val Thr Trp Val Glu Ser His Asp Thr Tyr Ala Asn
            275                 280                 285

Asp Asp Glu Glu Ser Thr Trp Met Ser Asp Asp Ile Arg Leu Gly
            290                 295                 300

Trp Ala Val Ile Gly Ser Arg Ser Gly Ser Thr Pro Leu Phe Phe Ser
305                 310                 315                 320

Arg Pro Glu Gly Gly Asn Gly Val Arg Phe Pro Gly Lys Ser Gln
                325                 330                 335

Ile Gly Asp Arg Gly Ser Ala Leu Phe Lys Asp Gln Ala Ile Thr Ala
                340                 345                 350

Val Asn Thr Phe His Asn Val Met Ala Gly Gln Pro Glu Glu Leu Ser
            355                 360                 365

Asn Pro Asn Gly Asn Asn Gln Val Phe Met Asn Gln Arg Gly Ser Lys
            370                 375                 380

Gly Val Val Leu Ala Asn Ala Gly Ser Ser Val Thr Ile Asn Thr
385                 390                 395                 400

Ser Ala Lys Leu Pro Asp Gly Arg Tyr Asp Asn Arg Ala Gly Ala Gly
                405                 410                 415

Ser Phe Gln Val Ala Asn Gly Lys Leu Thr Gly Thr Ile Asn Ala Arg
                420                 425                 430

Ser Ala Ala Val Leu Tyr Pro Asp Asp Ile Gly Asn Ala Pro His Val
                435                 440                 445

Phe Leu Glu Asn Tyr Gln Thr Gly Ala Val His Ser Phe Asn Asp Gln
450                 455                 460

Leu Thr Val Thr Leu Arg Ala Asn Ala Lys Thr Thr Lys Ala Val Tyr
465                 470                 475                 480

Gln Ile Asn Asn Gly Gln Gln Thr Ala Phe Lys Asp Gly Asp Arg Leu
                485                 490                 495

Thr Ile Gly Lys Gly Asp Pro Ile Gly Thr Thr Tyr Asn Ile Lys Leu
                500                 505                 510

Thr Gly Thr Asn Gly Glu Gly Ala Ala Arg Thr Gln Glu Tyr Thr Phe
            515                 520                 525

Val Lys Lys Asp Pro Ser Gln Thr Asn Ile Ile Gly Tyr Gln Asn Pro
530                 535                 540

Asp His Trp Gly Gln Val Asn Ala Tyr Ile Tyr Lys His Asp Gly Gly
545                 550                 555                 560

Arg Ala Ile Glu Leu Thr Gly Ser Trp Pro Gly Lys Ala Met Thr Lys
                565                 570                 575

Asn Ala Asn Gly Met Tyr Thr Leu Thr Leu Pro Glu Asn Thr Asp Thr
            580                 585                 590

Ala Asn Ala Lys Val Ile Phe Asn Asn Gly Ser Ala Gln Val Pro Gly
            595                 600                 605

Gln Asn Gln Pro Gly Phe Asp Tyr Val Gln Asn Gly Leu Tyr Asn Asn
            610                 615                 620

Ser Gly Leu Asn Gly Tyr Leu Pro His
625                 630

<210> SEQ ID NO 8
<211> LENGTH: 463

```
<212> TYPE: PRT
<213> ORGANISM: Thermococcus gammatolerans

<400> SEQUENCE: 8

Met Arg Arg Tyr Thr Arg Val Leu Ile Leu Leu Met Ala Leu Phe Leu
1               5                   10                  15

Leu Ala Gly Leu Tyr Tyr Pro Ser Ala Ser Ala Lys Tyr Ser Glu
            20                  25                  30

Leu Glu Gln Gly Gly Val Ile Met Gln Ala Phe Tyr Trp Asp Val Pro
            35                  40                  45

Ala Gly Gly Ile Trp Trp Asp Thr Ile Arg Gln Lys Ile Pro Glu Trp
        50                  55                  60

Tyr Asp Ala Gly Ile Ser Ala Ile Trp Ile Pro Pro Ala Ser Lys Gly
65                  70                  75                  80

Met Gly Gly Ala Tyr Ser Met Gly Tyr Asp Pro Tyr Asp Tyr Phe Asp
                85                  90                  95

Leu Gly Glu Phe Tyr Gln Lys Gly Thr Val Glu Thr Arg Phe Gly Ser
            100                 105                 110

Lys Glu Glu Leu Val Asn Met Ile Ser Thr Ala His Arg Tyr Gly Ile
        115                 120                 125

Lys Val Ile Ala Asp Ile Val Ile Asn His Arg Ala Gly Gly Asp Leu
        130                 135                 140

Glu Trp Asn Pro Tyr Val Gly Asp Tyr Thr Trp Thr Asp Phe Ser Gln
145                 150                 155                 160

Val Ala Ser Gly Lys Tyr Lys Ala His Tyr Met Asp Phe His Pro Asn
                165                 170                 175

Asn Tyr Ser Thr Ser Asp Glu Gly Thr Phe Gly Gly Phe Pro Asp Ile
            180                 185                 190

Asp His Leu Val Pro Phe Asn Lys Tyr Trp Leu Trp Ala Ser Asp Glu
        195                 200                 205

Ser Tyr Ala Ala Tyr Leu Arg Ser Ile Gly Val Asp Ala Trp Arg Phe
    210                 215                 220

Asp Tyr Val Lys Gly Tyr Gly Ala Trp Val Val Lys Asp Trp Leu Ser
225                 230                 235                 240

Trp Trp Gly Gly Trp Ala Val Gly Glu Tyr Trp Asp Thr Asp Val Asn
                245                 250                 255

Ala Leu Leu Asn Trp Ala Tyr Asp Ser Gly Ala Lys Val Phe Asp Phe
            260                 265                 270

Pro Leu Tyr Tyr Lys Met Asp Glu Ala Phe Asp Asn Lys Asn Ile Pro
        275                 280                 285

Ala Leu Val Tyr Ala Ile Gln Asn Gly Gly Thr Val Val Ser Arg Asp
    290                 295                 300

Pro Phe Lys Ala Val Thr Phe Val Ala Asn His Asp Thr Asn Ile Ile
305                 310                 315                 320

Trp Asn Lys Tyr Pro Ala Tyr Ala Phe Ile Leu Thr Tyr Glu Gly Gln
                325                 330                 335

Pro Val Ile Phe Tyr Arg Asp Tyr Glu Glu Trp Leu Asn Lys Asp Lys
            340                 345                 350

Leu Asn Asn Leu Ile Trp Ile His Glu His Leu Ala Gly Gly Ser Thr
        355                 360                 365

Lys Ile Leu Tyr Tyr Asp Asp Asp Glu Leu Ile Phe Met Arg Glu Gly
370                 375                 380

Tyr Gly Asp Arg Pro Gly Leu Ile Thr Tyr Ile Asn Leu Gly Ser Gly
385                 390                 395                 400
```

Trp Ala Glu Arg Trp Val Asn Val Gly Ser Lys Phe Ala Gly Tyr Thr
            405                 410                 415

Ile His Glu Tyr Thr Gly Asn Leu Gly Gly Trp Val Asp Arg Tyr Val
            420                 425                 430

Tyr Tyr Asn Gly Trp Val Lys Leu Thr Ala Pro Pro His Asp Pro Ala
            435                 440                 445

Asn Gly Tyr Tyr Gly Tyr Ser Val Trp Ser Tyr Ala Gly Val Gly
    450                 455                 460

<210> SEQ ID NO 9
<211> LENGTH: 457
<212> TYPE: PRT
<213> ORGANISM: Thermococcus thioreducens

<400> SEQUENCE: 9

Met Ala Arg Lys Val Thr Val Ala Leu Leu Val Leu Val Leu Val Leu
1               5                   10                  15

Ser Leu Ser Ala Val Pro Ala Lys Ala Glu Thr Leu Glu Asn Gly Gly
            20                  25                  30

Val Ile Met Gln Ala Phe Tyr Trp Asp Val Pro Met Gly Gly Ile Trp
        35                  40                  45

Trp Asp Thr Ile Ala Gln Lys Ile Pro Asp Trp Ala Ser Ala Gly Ile
    50                  55                  60

Ser Ala Ile Trp Ile Pro Pro Ala Ser Lys Gly Met Ser Gly Gly Tyr
65                  70                  75                  80

Ser Met Gly Tyr Asp Pro Tyr Asp Tyr Phe Asp Leu Gly Glu Tyr Tyr
                85                  90                  95

Gln Lys Gly Thr Val Glu Thr Arg Phe Gly Ser Lys Gln Glu Leu Val
            100                 105                 110

Asn Met Ile Asn Thr Ala His Ala Tyr Gly Met Lys Val Ile Ala Asp
        115                 120                 125

Ile Val Ile Asn His Arg Ala Gly Gly Asp Leu Glu Trp Asn Pro Phe
    130                 135                 140

Val Asn Asp Tyr Thr Trp Thr Asp Phe Ser Lys Val Ala Ser Gly Lys
145                 150                 155                 160

Tyr Thr Ala Asn Tyr Leu Asp Phe His Pro Asn Glu Leu His Ala Gly
                165                 170                 175

Asp Ser Gly Thr Phe Gly Gly Tyr Pro Asp Ile Cys His Asp Lys Ser
            180                 185                 190

Trp Asp Gln Tyr Trp Leu Trp Ala Ser Asn Glu Ser Tyr Ala Ala Tyr
        195                 200                 205

Leu Arg Ser Ile Gly Ile Asp Ala Trp Arg Phe Asp Tyr Val Lys Gly
    210                 215                 220

Tyr Ala Pro Trp Val Val Lys Asp Trp Leu Asn Trp Trp Gly Gly Trp
225                 230                 235                 240

Ala Val Gly Glu Tyr Trp Asp Thr Asn Val Asp Ala Leu Leu Asn Trp
                245                 250                 255

Ala Tyr Ala Ser Gly Ala Lys Val Phe Asp Phe Pro Leu Tyr Tyr Lys
            260                 265                 270

Met Asp Glu Ala Phe Asp Asn Asn Ile Pro Ala Leu Val Asp Ala
        275                 280                 285

Leu Arg Tyr Gly Gln Thr Val Val Ser Arg Asp Pro Phe Lys Ala Val
    290                 295                 300

Thr Phe Val Ala Asn His Asp Thr Asp Ile Ile Trp Asn Lys Tyr Pro

```
            305                 310                 315                 320
Ala Tyr Ala Phe Ile Leu Thr Tyr Glu Gly Gln Pro Met Ile Phe Tyr
                325                 330                 335

Arg Asp Tyr Glu Glu Trp Leu Asn Lys Asp Arg Leu Lys Asn Leu Ile
                340                 345                 350

Trp Ile His Asp His Leu Ala Gly Gly Ser Thr Asp Ile Val Tyr Tyr
                355                 360                 365

Asp Ser Asp Glu Leu Ile Phe Val Arg Asn Gly Tyr Gly Ser Lys Pro
            370                 375                 380

Gly Leu Ile Thr Tyr Ile Asn Leu Gly Ser Ser Lys Ala Gly Arg Trp
385                 390                 395                 400

Val Tyr Val Pro Lys Phe Ala Gly Ser Cys Ile His Glu Tyr Thr Gly
                405                 410                 415

Asn Leu Gly Gly Trp Val Asp Lys Trp Val Asp Ser Ser Gly Trp Val
            420                 425                 430

Tyr Leu Glu Ala Pro Ala His Asp Pro Ala Asn Gly Gln Tyr Gly Tyr
                435                 440                 445

Ser Val Trp Ser Tyr Cys Gly Val Gly
    450                 455

<210> SEQ ID NO 10
<211> LENGTH: 461
<212> TYPE: PRT
<213> ORGANISM: Thermococcus eurythermalis

<400> SEQUENCE: 10

Met Lys Pro Ala Lys Leu Leu Val Phe Val Leu Val Val Ser Ile Leu
1               5                   10                  15

Ala Gly Leu Tyr Ala Gln Pro Ala Gly Ala Ala Lys Tyr Leu Glu Leu
            20                  25                  30

Glu Glu Gly Gly Val Ile Met Gln Ala Phe Tyr Trp Asp Val Pro Ser
        35                  40                  45

Gly Gly Ile Trp Trp Asp Thr Ile Arg Gln Lys Ile Pro Glu Trp Tyr
    50                  55                  60

Asp Ala Gly Ile Ser Ala Ile Trp Ile Pro Pro Ala Ser Lys Gly Met
65                  70                  75                  80

Gly Gly Ala Tyr Ser Met Gly Tyr Asp Pro Tyr Asp Phe Phe Asp Leu
                85                  90                  95

Gly Glu Tyr Asp Gln Lys Gly Thr Val Glu Thr Arg Phe Gly Ser Lys
            100                 105                 110

Gln Glu Leu Val Asn Met Ile Asn Thr Ala His Ala Tyr Gly Ile Lys
        115                 120                 125

Val Ile Ala Asp Ile Val Ile Asn His Arg Ala Gly Gly Asp Leu Glu
    130                 135                 140

Trp Asn Pro Phe Val Asn Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
                165                 170                 175

Val Lys Cys Cys Asp Glu Gly Thr Phe Gly Gly Phe Pro Asp Ile Ala
            180                 185                 190

His Glu Lys Ser Trp Asp Gln Tyr Trp Leu Trp Ala Ser Asn Glu Ser
        195                 200                 205

Tyr Ala Ala Tyr Leu Arg Ser Ile Gly Val Asp Ala Trp Arg Phe Asp
    210                 215                 220
```

```
Tyr Val Lys Gly Tyr Gly Ala Trp Val Val Lys Asp Trp Leu Asp Trp
225                 230                 235                 240

Trp Gly Gly Trp Ala Val Gly Glu Tyr Trp Asp Thr Asn Val Asp Ala
            245                 250                 255

Leu Leu Asn Trp Ala Tyr Ser Ser Asp Ala Lys Val Phe Asp Phe Pro
        260                 265                 270

Leu Tyr Tyr Lys Met Asp Ala Ala Phe Asp Asn Lys Asn Ile Pro Ala
    275                 280                 285

Leu Val Glu Ala Leu Lys Asn Gly Gly Thr Val Val Ser Arg Asp Pro
290                 295                 300

Phe Lys Ala Val Thr Phe Val Ala Asn His Asp Thr Asp Ile Ile Trp
305                 310                 315                 320

Asn Lys Tyr Pro Ala Tyr Ala Phe Ile Leu Thr Tyr Glu Gly Gln Pro
                325                 330                 335

Thr Ile Phe Tyr Arg Asp Tyr Glu Glu Trp Leu Asn Lys Asp Arg Leu
            340                 345                 350

Lys Asn Leu Ile Trp Ile His Asp His Leu Ala Gly Gly Ser Thr Asp
        355                 360                 365

Ile Val Tyr Tyr Asp Asn Asp Glu Leu Ile Phe Val Arg Asn Gly Tyr
370                 375                 380

Gly Asp Lys Pro Gly Leu Ile Thr Tyr Ile Asn Leu Gly Ser Ser Lys
385                 390                 395                 400

Ala Gly Arg Trp Val Tyr Val Pro Lys Phe Ala Gly Ala Cys Ile His
                405                 410                 415

Glu Tyr Thr Gly Asn Leu Gly Gly Trp Val Asp Lys Trp Val Asp Ser
            420                 425                 430

Ser Gly Trp Val Tyr Leu Glu Ala Pro Ala His Asp Pro Ala Asn Gly
        435                 440                 445

Tyr Tyr Gly Tyr Ser Val Trp Ser Tyr Cys Gly Val Gly
450                 455                 460

<210> SEQ ID NO 11
<211> LENGTH: 457
<212> TYPE: PRT
<213> ORGANISM: Thermococcus hydrothermalis

<400> SEQUENCE: 11

Met Ala Arg Lys Val Leu Val Ala Leu Leu Val Phe Leu Val Val Leu
1               5                   10                  15

Ser Val Ser Ala Val Pro Ala Lys Ala Glu Thr Leu Glu Asn Gly Gly
            20                  25                  30

Val Ile Met Gln Ala Phe Tyr Trp Asp Val Pro Gly Gly Gly Ile Trp
        35                  40                  45

Trp Asp Thr Ile Ala Gln Lys Ile Pro Asp Trp Ala Ser Ala Gly Ile
    50                  55                  60

Ser Ala Ile Trp Ile Pro Pro Ala Ser Lys Gly Met Ser Gly Gly Tyr
65                  70                  75                  80

Ser Met Gly Tyr Asp Pro Tyr Asp Phe Phe Asp Leu Gly Glu Tyr Tyr
            85                  90                  95

Gln Lys Gly Ser Val Glu Thr Arg Phe Gly Ser Lys Glu Glu Leu Val
        100                 105                 110

Asn Met Ile Asn Thr Ala His Ala His Asn Met Lys Val Ile Ala Asp
    115                 120                 125

Ile Val Ile Asn His Arg Ala Gly Gly Asp Leu Glu Trp Asn Pro Phe
130                 135                 140
```

Thr Asn Ser Tyr Thr Trp Thr Asp Phe Ser Lys Val Ala Ser Gly Lys
145                 150                 155                 160

Tyr Thr Ala Asn Tyr Leu Asp Phe His Pro Asn Glu Leu His Ala Gly
                165                 170                 175

Asp Ser Gly Thr Phe Gly Gly Tyr Pro Asp Ile Cys His Asp Lys Ser
            180                 185                 190

Trp Asp Gln His Trp Leu Trp Ala Ser Asn Glu Ser Tyr Ala Ala Tyr
        195                 200                 205

Leu Arg Ser Ile Gly Ile Asp Ala Trp Arg Phe Asp Tyr Val Lys Gly
210                 215                 220

Tyr Ala Pro Trp Val Val Lys Asn Trp Leu Asn Arg Trp Gly Gly Trp
225                 230                 235                 240

Ala Val Gly Glu Tyr Trp Asp Thr Asn Val Asp Ala Leu Leu Ser Trp
                245                 250                 255

Ala Tyr Asp Ser Gly Ala Lys Val Phe Asp Phe Pro Leu Tyr Tyr Lys
            260                 265                 270

Met Asp Glu Ala Phe Asp Asn Asn Ile Pro Ala Leu Val Asp Ala
        275                 280                 285

Leu Lys Asn Gly Gly Thr Val Val Ser Arg Asp Pro Phe Lys Ala Val
290                 295                 300

Thr Phe Val Ala Asn His Asp Thr Asn Ile Ile Trp Asn Lys Tyr Pro
305                 310                 315                 320

Ala Tyr Ala Phe Ile Leu Thr Tyr Glu Gly Gln Pro Ala Ile Phe Tyr
                325                 330                 335

Arg Asp Tyr Glu Glu Trp Leu Asn Lys Asp Arg Leu Arg Asn Leu Ile
            340                 345                 350

Trp Ile His Asp His Leu Ala Gly Gly Ser Thr Asp Ile Ile Tyr Tyr
        355                 360                 365

Asp Ser Asp Glu Leu Ile Phe Val Arg Asn Gly Tyr Gly Asp Lys Pro
370                 375                 380

Gly Leu Ile Thr Tyr Ile Asn Leu Gly Ser Ser Lys Ala Gly Arg Trp
385                 390                 395                 400

Val Tyr Val Pro Lys Phe Ala Gly Ser Cys Ile His Glu Tyr Thr Gly
                405                 410                 415

Asn Leu Gly Gly Trp Ile Asp Lys Trp Val Asp Ser Ser Gly Arg Val
            420                 425                 430

Tyr Leu Glu Ala Pro Ala His Asp Pro Ala Asn Gly Gln Tyr Gly Tyr
        435                 440                 445

Ser Val Trp Ser Tyr Cys Gly Val Gly
450                 455

<210> SEQ ID NO 12
<211> LENGTH: 460
<212> TYPE: PRT
<213> ORGANISM: Pyrococcus furiosus

<400> SEQUENCE: 12

Met Asn Ile Lys Lys Leu Thr Pro Leu Leu Thr Leu Leu Leu Phe Phe
1               5                   10                  15

Ile Val Leu Ala Ser Pro Val Ser Ala Ala Lys Tyr Leu Glu Leu Glu
                20                  25                  30

Glu Gly Gly Val Ile Met Gln Ala Phe Tyr Trp Asp Val Pro Gly Gly
            35                  40                  45

Gly Ile Trp Trp Asp His Ile Arg Ser Lys Ile Pro Glu Trp Tyr Glu

```
            50                  55                  60
Ala Gly Ile Ser Ala Ile Trp Leu Pro Pro Ser Lys Gly Met Ser
 65                  70                  75                  80

Gly Gly Tyr Ser Met Gly Tyr Asp Pro Tyr Asp Phe Asp Leu Gly
                 85                  90                  95

Glu Tyr Tyr Gln Lys Gly Thr Val Glu Thr Arg Phe Gly Ser Lys Glu
                    100                 105                 110

Glu Leu Val Arg Leu Ile Gln Thr Ala His Ala Tyr Gly Ile Lys Val
                115                 120                 125

Ile Ala Asp Val Val Ile Asn His Arg Ala Gly Gly Asp Leu Glu Trp
130                 135                 140

Asn Pro Phe Val Gly Asp Tyr Thr Trp Thr Asp Phe Ser Lys Val Ala
145                 150                 155                 160

Ser Gly Lys Tyr Thr Ala Asn Tyr Leu Asp Phe His Pro Asn Glu Leu
                165                 170                 175

His Cys Cys Asp Glu Gly Thr Phe Gly Gly Phe Pro Asp Ile Cys His
                180                 185                 190

His Lys Glu Trp Asp Gln Tyr Trp Leu Trp Lys Ser Asn Glu Ser Tyr
                195                 200                 205

Ala Ala Tyr Leu Arg Ser Ile Gly Phe Asp Gly Trp Arg Phe Asp Tyr
210                 215                 220

Val Lys Gly Tyr Gly Ala Trp Val Val Arg Asp Trp Leu Asn Trp Trp
225                 230                 235                 240

Gly Gly Trp Ala Val Gly Glu Tyr Trp Asp Thr Asn Val Asp Ala Leu
                245                 250                 255

Leu Ser Trp Ala Tyr Glu Ser Gly Ala Lys Val Phe Asp Phe Pro Leu
                260                 265                 270

Tyr Tyr Lys Met Asp Glu Ala Phe Asp Asn Asn Ile Pro Ala Leu
                275                 280                 285

Val Tyr Ala Leu Gln Asn Gly Gln Thr Val Val Ser Arg Asp Pro Phe
290                 295                 300

Lys Ala Val Thr Phe Val Ala Asn His Asp Thr Asp Ile Ile Trp Asn
305                 310                 315                 320

Lys Tyr Pro Ala Tyr Ala Phe Ile Leu Thr Tyr Glu Gly Gln Pro Val
                325                 330                 335

Ile Phe Tyr Arg Asp Phe Glu Glu Trp Leu Asn Lys Asp Lys Leu Ile
                340                 345                 350

Asn Leu Ile Trp Ile His Asp His Leu Ala Gly Gly Ser Thr Thr Ile
                355                 360                 365

Val Tyr Tyr Asp Asn Asp Glu Leu Ile Phe Val Arg Asn Gly Asp Ser
370                 375                 380

Arg Arg Pro Gly Leu Ile Thr Tyr Ile Asn Leu Ser Pro Asn Trp Val
385                 390                 395                 400

Gly Arg Trp Val Tyr Val Pro Lys Phe Ala Gly Ala Cys Ile His Glu
                405                 410                 415

Tyr Thr Gly Asn Leu Gly Gly Trp Val Asp Lys Arg Val Asp Ser Ser
                420                 425                 430

Gly Trp Val Tyr Leu Glu Ala Pro Pro His Asp Pro Ala Asn Gly Tyr
                435                 440                 445

Tyr Gly Tyr Ser Val Trp Ser Tyr Cys Gly Val Gly
450                 455                 460

<210> SEQ ID NO 13
```

<211> LENGTH: 1344
<212> TYPE: PRT
<213> ORGANISM: Thermococcus onnurineus
<220> FEATURE:
<221> NAME/KEY: SIGNAL
<222> LOCATION: (1)..(19)

<400> SEQUENCE: 13

```
Met Leu Leu Gln Ala Phe Leu Phe Leu Leu Ala Gly Phe Ala Ala Lys
 1               5                  10                  15

Ile Ser Ala Val Gln Pro Ser Val Thr Ala Glu Glu Pro Lys Pro Leu
            20                  25                  30

Asn Val Ile Ile Val Trp His Gln His Gln Pro Tyr Tyr Tyr Asp Pro
        35                  40                  45

Ile Gln Asp Ile Tyr Thr Arg Pro Trp Val Arg Leu His Ala Ala Asn
50                  55                  60

Asn Tyr Trp Lys Met Ala Tyr Tyr Leu Ser Gln Tyr Pro Glu Val His
65                  70                  75                  80

Ala Thr Ile Asp Leu Ser Gly Ser Leu Ile Ala Gln Leu Ala Asp Tyr
                85                  90                  95

Met Asn Gly Ala Lys Asp Asn Tyr Gln Ile Ile Thr Glu Lys Ile Ala
            100                 105                 110

Asn Gly Glu Pro Leu Thr Val Asp Glu Lys Trp Phe Met Leu Gln Ala
        115                 120                 125

Pro Gly Gly Phe Phe Asp His Thr Ile Pro Trp Asn Gly Glu Pro Ile
130                 135                 140

Thr Asp Pro Asn Gly Asn Pro Ile Arg Asp Phe Trp Asn Arg Tyr Thr
145                 150                 155                 160

Glu Leu Lys Asn Lys Met Met Gln Ala Lys Ala Lys Tyr Ala Asn Leu
                165                 170                 175

Pro Leu Glu Glu Gln Lys Ile Ala Val Thr Asn Glu Phe Thr Glu Gln
            180                 185                 190

Asp Tyr Ile Asp Leu Ala Val Leu Phe Asn Leu Ala Trp Ile Asp Tyr
        195                 200                 205

Gly Tyr Ile Met Ser His Pro Glu Leu Lys Ala Leu Tyr Asp Lys Val
210                 215                 220

Asp Glu Gly Gly Tyr Thr Arg Glu Asp Val Lys Thr Val Leu Asp Ala
225                 230                 235                 240

Gln Met Trp Leu Leu Asn His Thr Phe Glu Glu His Glu Ala Ile Asn
                245                 250                 255

Leu Leu Leu Gly Asn Gly Asn Val Glu Val Thr Val Pro Tyr Ala
            260                 265                 270

His Pro Ile Gly Pro Ile Leu Asn Asp Phe Gly Trp Glu Ser Asp Phe
        275                 280                 285

Asn Asp Gln Val Lys Lys Ala Asp Glu Leu Tyr Lys Glu Tyr Leu Gly
290                 295                 300

Gly Gly Gln Val Glu Pro Val Gly Gly Trp Ala Ala Glu Ser Ala Leu
305                 310                 315                 320

Asn Asp Lys Thr Leu Glu Ile Leu Ala Gly Asn Gly Trp Thr Trp Val
                325                 330                 335

Met Thr Asp Gln Leu Val Leu Gln Lys Leu Gly Ile Glu Gly Thr Val
            340                 345                 350

Glu Asn Tyr His Lys Pro Trp Val Ala Glu Phe Asp Glu Lys Lys Ile
        355                 360                 365

Tyr Leu Phe Pro Arg Asp His Ala Leu Ser Asp Arg Val Gly Phe Thr
```

-continued

```
            370                 375                 380
Tyr Gly Gly Met Asn Gln Tyr Asp Ala Val Glu Asp Phe Ile Asn Glu
385                 390                 395                 400

Leu Leu Lys Leu Gln Lys Gln Asn Tyr Asp Gly Ser Leu Val Tyr Val
            405                 410                 415

Ile Thr Leu Asp Gly Glu Asn Pro Trp Glu His Tyr Pro Tyr Asp Gly
            420                 425                 430

Lys Leu Phe Leu Glu Thr Leu Tyr Lys Arg Leu Thr Glu Leu Gln Glu
            435                 440                 445

Gln Gly Leu Ile Arg Thr Leu Thr Pro Ser Glu Tyr Ile Gln Leu Tyr
450                 455                 460

Gly Asp Gln Ala Asn Lys Leu Thr Pro Gln Met Met Glu Arg Leu Asp
465                 470                 475                 480

Leu Thr Gly Asp Lys Val Glu Ala Leu Lys Lys Ala Gln Ser Leu Gly
            485                 490                 495

Asp Leu Tyr Asp Met Val Gly Val Lys Glu Met Gln Trp Pro Glu
            500                 505                 510

Ser Ser Trp Ile Asp Gly Thr Leu Ser Thr Trp Ile Gly Glu Pro Gln
            515                 520                 525

Glu Asn Tyr Gly Trp Tyr Trp Leu Tyr Leu Ala Arg Lys Ala Leu Met
530                 535                 540

Glu His Lys Asp Glu Met Ser Gln Thr Tyr Trp Glu Lys Ala Tyr Glu
545                 550                 555                 560

Tyr Leu Leu Arg Ala Glu Ala Ser Asp Trp Phe Trp Trp Tyr Gly Ser
            565                 570                 575

Asp Gln Ser Ser Gly Gln Asp Tyr Thr Phe Asp Arg Tyr Leu Lys Thr
            580                 585                 590

Tyr Leu Tyr Glu Met Tyr Arg Leu Ala Gly Leu Glu Pro Pro Gly Tyr
            595                 600                 605

Leu Tyr Gly Asn Phe Phe Pro Asp Gly Glu Pro Tyr Thr Val Arg Ala
            610                 615                 620

Leu Asp Gly Leu Gly Glu Gly Gln Val Lys Asn Tyr Ser Ser Met Ser
625                 630                 635                 640

Ser Leu Ala Glu Gly Val Ser Val Tyr Phe Asp Gly Asp Gly Ile His
            645                 650                 655

Phe Ile Val Lys Gly Glu Leu Asn Glu Phe Glu Ile Ser Ile Tyr Glu
            660                 665                 670

Lys Gly Glu Arg Val Gly Asn Thr Phe Thr Ile Leu Gln Asp Lys Pro
            675                 680                 685

Thr Glu Leu Arg Tyr Ser Met Phe Pro Phe Ser Lys Asp Ser Val Gly
            690                 695                 700

Leu Met Ile Thr Lys His Ile Val Tyr Lys Asp Asn Lys Ala Glu Val
705                 710                 715                 720

Tyr Gln Ala Thr Asn Tyr Glu Asp Ser Glu Lys Ile Gly Asp Ala Val
            725                 730                 735

Val Lys Thr Val Asn Gly Arg Val Glu Ile Val Pro Phe Glu Tyr
            740                 745                 750

Ile Lys Thr Pro Glu Asp Phe Tyr Phe Ala Val Ser Thr Val Lys Asp
            755                 760                 765

Gly Glu Leu Glu Val Ile Thr Thr Pro Ile Glu Leu Lys Leu Pro Thr
            770                 775                 780

Glu Val Lys Gly Val Thr Leu Val Asp Ile Ala Asp Pro Glu Gly Asp
785                 790                 795                 800
```

```
Asp Tyr Gly Pro Gly Thr Tyr Thr Tyr Pro Thr Asp Lys Val Phe Val
            805                 810                 815

Glu Gly Ala Phe Asp Leu Leu Arg Phe Arg Met Leu Glu Gln Thr Asp
            820                 825                 830

Ala Tyr Val Met Glu Phe Tyr Phe Lys Asp Leu Gly Gly Asn Pro Trp
            835                 840                 845

Asn Gly Pro Asn Gly Phe Ser Leu Gln Ile Ile Glu Val Tyr Leu Asp
            850                 855                 860

Phe Lys Glu Gly Gly Asn Ser Ser Ala Ile Lys Met Phe Pro Asp Gly
865                 870                 875                 880

Pro Gly Ala Asn Val Asn Leu Asp Pro Glu His Pro Trp Asp Val Ala
                885                 890                 895

Leu Arg Ile Ala Gly Trp Asp Tyr Gly Asn Leu Ile Val Leu Pro Asn
            900                 905                 910

Gly Thr Val Tyr Gln Gly Glu Met Gln Ile Ser Ala Asp Pro Val Lys
            915                 920                 925

Ser Ala Ile Ile Val Lys Ile Pro Lys Lys Tyr Ile Gln Ile Asn Glu
930                 935                 940

Asp Tyr Gly Phe Trp Gly Asp Val Leu Val Gly Ser Gln Asp Gly Tyr
945                 950                 955                 960

Gly Pro Asp Lys Trp Arg Pro Val Ala Val Glu Ala Glu Gln Trp Lys
                965                 970                 975

Leu Gly Gly Ala Asp Pro Gln Ala Val Ile Asn Asn Val Ala Pro Arg
            980                 985                 990

Val Val Asp Glu Leu Val Pro Glu Gly Phe Lys Pro Thr Gln Glu Glu
            995                 1000                1005

Gln Leu Ser Ser Tyr Asp Ala Asn Glu Ile Lys Leu Ala Thr Val
            1010                1015                1020

Lys Ala Ile Pro Leu Leu Lys Gln Gly Ile Thr Met Leu Asp Pro
            1025                1030                1035

Glu Gly Asp Asp His Gly Pro Gly Thr Tyr Thr Tyr Pro Thr Asp
            1040                1045                1050

Lys Val Phe Val Pro Gly His Leu Asp Leu Leu Lys Phe Lys Met
            1055                1060                1065

Ile Glu Gly Asp Asp Ala Trp Thr Leu Glu Phe Tyr Phe Lys Asp
            1070                1075                1080

Leu Gly Gly Asn Pro Trp Asn Gly Pro Asn Gly Phe Ser Leu Gln
            1085                1090                1095

Ile Ile Glu Val Tyr Phe Asp Phe Thr Asp Gly Gly Asn Thr Ser
            1100                1105                1110

Ala Ile Lys Met Phe Pro Asp Gly Pro Gly Ser Asn Val Gln Leu
            1115                1120                1125

Asp Pro Gly His Pro Trp Asp Leu Ala Leu Arg Ile Ala Gly Trp
            1130                1135                1140

Asp Tyr Gly Asn Leu Ile Val Leu Pro Asp Gly Thr Val Tyr Gln
            1145                1150                1155

Gly Glu Met Gln Ile Ser Ala Asp Pro Val Lys Asn Ala Ile Ile
            1160                1165                1170

Val Lys Val Pro Lys Lys Tyr Leu Ser Val Thr Asp Tyr Gly Leu
            1175                1180                1185

Tyr Thr Ala Val Leu Val Gly Ser Gln Asp Gly Tyr Gly Pro Asp
            1190                1195                1200
```

-continued

```
Lys Trp Arg Pro Val Ala Val Glu Ala Glu Gln Trp Lys Leu Gly
    1205                1210                1215

Gly Ala Asp Pro Asn Ala Val Ile Asp Asn Leu Ala Pro Arg Val
    1220                1225                1230

Val Asp Met Leu Val Pro Glu Gly Leu Lys Pro Thr Gln Glu Glu
    1235                1240                1245

Gln Leu Ser Ser Tyr Asp Leu Glu Lys Lys Thr Leu Ala Thr Val
    1250                1255                1260

Leu Met Ile Pro Leu Val Glu Gly Thr Gly Gly Glu Glu Val Thr
    1265                1270                1275

Pro Thr Glu Thr Pro Thr Glu Thr Pro Ser Glu Thr Thr Thr Thr
    1280                1285                1290

Pro Ser Glu Thr Thr Thr Thr Pro Gln Glu Thr Thr Thr Thr Pro
    1295                1300                1305

Ala Glu Thr Thr Thr Ser Thr Thr Thr Pro Gly Glu Glu Gly Gly
    1310                1315                1320

Ile Cys Gly Pro Ala Val Leu Leu Gly Leu Ala Leu Thr Pro Leu
    1325                1330                1335

Leu Leu Arg Arg Arg Arg
    1340

<210> SEQ ID NO 14
<211> LENGTH: 564
<212> TYPE: PRT
<213> ORGANISM: Aspergillus niger
<220> FEATURE:
<221> NAME/KEY: SIGNAL
<222> LOCATION: (1)..(19)

<400> SEQUENCE: 14

Met Arg Ser Thr Gly Tyr Leu Leu Thr Leu Ser Ala Ala Phe Gln Val
1               5                   10                  15

Ala Gln Ala Ala Val Thr Ala Asn Asn Ser Gln Leu Leu Thr Trp Trp
                20                  25                  30

His Asn Thr Gly Glu Ile Asn Thr Gln Thr Pro Val Ala Asp Gly Asn
            35                  40                  45

Val Arg Gln Ser Gly Leu Tyr Ser Val Lys Val Gln Thr Thr Pro Ala
        50                  55                  60

Ser Ser Ser Leu Tyr Tyr Asp Ser Phe Val Tyr Leu Ala Ile Pro Gly
65                  70                  75                  80

Asn Gly Met Ser Asp Gln Leu Gln Tyr Thr Gln Gly Tyr Asn Gln Thr
                85                  90                  95

Gln Ala Trp Thr Ser Phe Leu Tyr Ser His Asp Ala Thr Val Lys Ile
            100                 105                 110

Ser Arg Asn Gly Ser Ser Ala Asn Ser Asn Val Val Ile Arg Pro Thr
        115                 120                 125

Ser Leu Asn Phe Pro Val Arg Tyr Asp Asn Gln Ser Val Tyr Ile Thr
    130                 135                 140

Val Pro Tyr Ser Pro Thr Gly Tyr Arg Phe Ser Val Glu Phe Asp Asp
145                 150                 155                 160

Asp Leu Ile Ser Leu Ala Pro Ser Gly Ala Arg Gln Pro Glu Asn Ala
                165                 170                 175

Leu Leu Ile Phe Ala Ser Pro Phe Glu Asn Ser Ser Thr Lys Pro Gln
            180                 185                 190

Pro Gly Ser Pro Asn Ser Ile Ala Pro Ala Pro Gly Arg Val Leu Gly
        195                 200                 205
```

```
Leu Asn Thr Thr Ser Ala Ser Thr Val Val Phe Asn Pro Gly Val Tyr
    210                 215                 220

Tyr Phe Thr Gly His Asp His Met Val Leu Ser Ser Val Thr Trp
225                 230                 235                 240

Val Tyr Phe Ala Pro Gly Ala Tyr Val Lys Gly Ala Val Glu Phe Leu
                245                 250                 255

Ser Thr Ala Ser Glu Val Lys Ala Ser Gly His Gly Val Leu Ser Gly
            260                 265                 270

Glu Gln Tyr Val Trp Tyr Ala Asp Pro Asp Glu Gly Tyr Gln Lys Ala
        275                 280                 285

Ser Gly Ala Asn Asn Asn Gly Leu Arg Met Trp Arg Gly Thr Leu Gly
    290                 295                 300

Asn Ser Ser Gln Thr Phe Val Leu Asn Gly Val Thr Val Ser Ala Pro
305                 310                 315                 320

Pro Phe Asn Ser Met Asp Trp Ser Gly Asn Ser Leu Asp Leu Ile Thr
                325                 330                 335

Cys Arg Val Asp Asp Tyr Lys Gln Val Gly Ala Phe Tyr Gly Gln Thr
            340                 345                 350

Asp Gly Leu Glu Met Tyr Pro Gly Thr Ile Leu Gln Asp Val Phe Tyr
        355                 360                 365

His Thr Asp Asp Asp Gly Leu Lys Met Tyr Tyr Ser Asn Val Thr Ala
    370                 375                 380

Arg Asn Ile Val Met Trp Lys Glu Ser Val Ala Pro Val Val Glu Phe
385                 390                 395                 400

Gly Trp Thr Pro Arg Asn Thr Glu Asn Val Leu Phe Asp Asn Val Asp
                405                 410                 415

Val Ile His Gln Ala Tyr Ala Asn Ala Gly Asn Asn Pro Gly Ile Phe
            420                 425                 430

Gly Ala Val Asn Asn Tyr Leu Tyr Ala Pro Asp Gly Leu Ser Ser Asn
        435                 440                 445

His Ser Thr Gly Asn Ser Asn Met Thr Val Arg Asn Ile Thr Trp Ser
    450                 455                 460

Asn Phe Arg Ala Glu Gly Ser Ser Ser Ala Leu Phe Arg Ile Asn Pro
465                 470                 475                 480

Ile Gln Asn Leu Asp Asn Ile Ser Ile Lys Asn Val Ser Ile Glu Ser
                485                 490                 495

Phe Glu Pro Leu Ser Ile Asn Thr Thr Glu Ser Trp Met Pro Val Trp
            500                 505                 510

Tyr Asp Leu Asn Asn Gly Lys Gln Ile Thr Val Thr Asp Phe Ser Ile
        515                 520                 525

Glu Gly Phe Thr Val Gly Asn Thr Thr Ile Thr Ala Ser Asn Ala Ala
    530                 535                 540

Ser Val Gly Arg Ile Asp Gly Val Asp Pro Ala Tyr Ala Gly Ser Val
545                 550                 555                 560

His Tyr Ile Asp

<210> SEQ ID NO 15
<211> LENGTH: 504
<212> TYPE: PRT
<213> ORGANISM: Artificial Sequence
<220> FEATURE:
<223> OTHER INFORMATION: Catalytic domain of SEQ ID NO: 5

<400> SEQUENCE: 15
```

```
Met Ser Arg Leu Leu Tyr Ala Leu Gly Ala Leu Ala Val Gly Gln Ser
1               5                   10                  15

Ala Leu Ala Ala Pro Gln Leu Ser Pro Arg Ala Thr Ser Leu Asp Ser
            20                  25                  30

Trp Leu Ser Ser Glu Thr Thr Phe Ser Leu Asn Gly Ile Leu Ala Asn
        35                  40                  45

Ile Gly Ser Ser Gly Ala Tyr Ser Lys Ser Ala Ser Gly Ala Val
50                  55                  60

Ile Ala Ser Pro Ser Thr Ser Asn Pro Asp Tyr Tyr Thr Trp Thr
65                  70                  75                  80

Arg Asp Ala Ala Leu Thr Leu Lys Ala Leu Val Asp Ile Phe Arg Asn
                85                  90                  95

Gly Asn Leu Gly Leu Gln Thr Val Ile Glu Gln Tyr Val Asn Ala Gln
            100                 105                 110

Ala Lys Leu Gln Thr Val Ser Asn Pro Ser Gly Gly Leu Ser Asp Gly
        115                 120                 125

Ala Gly Leu Gly Glu Pro Lys Phe Asn Val Asp Leu Ser Ala Phe Thr
    130                 135                 140

Gly Ala Trp Gly Arg Pro Gln Arg Asp Gly Pro Ala Leu Arg Ala Ile
145                 150                 155                 160

Ala Leu Ile Asp Phe Gly Asn Trp Leu Ile Asp Asn Gly Tyr Lys Ser
                165                 170                 175

Tyr Ala Val Asn Asn Val Trp Pro Ile Val Arg Asn Asp Leu Ala Tyr
            180                 185                 190

Val Ala Gln Tyr Trp Ser Gln Ser Gly Phe Asp Leu Trp Glu Glu Val
        195                 200                 205

Asn Ser Met Ser Phe Phe Thr Val Ala Asn Gln His Arg Ser Leu Val
    210                 215                 220

Glu Gly Ser Ala Phe Ala Ser Arg Val Gly Ala Ser Cys Ser Gly Cys
225                 230                 235                 240

Asp Ser Gln Ala Pro Gln Ile Leu Cys Tyr Met Gln Ser Phe Trp Thr
                245                 250                 255

Gly Ser Tyr Ile Asn Ala Asn Thr Gly Gly Gly Arg Ser Gly Lys Asp
            260                 265                 270

Ser Asn Thr Ile Leu Ala Ser Ile His Thr Phe Asp Pro Ala Ala Ser
    275                 280                 285

Cys Asp Asp Val Thr Phe Gln Pro Cys Ser Ser Arg Ala Leu Ala Asn
290                 295                 300

His Lys Val Tyr Thr Asp Ser Phe Arg Ser Val Tyr Ala Leu Asn Ser
305                 310                 315                 320

Gly Ile Ala Gln Gly Lys Ala Val Ser Val Gly Arg Tyr Pro Glu Asp
            325                 330                 335

Ser Tyr Tyr Gly Gly Asn Pro Trp Phe Leu Ser Asn Leu Ala Ala Ala
        340                 345                 350

Glu Gln Leu Tyr Asp Ala Ile Tyr Gln Trp Asn Lys Ile Gly Ser Ile
    355                 360                 365

Thr Ile Thr Ser Thr Ser Leu Ala Phe Phe Lys Asp Val Tyr Pro Ser
    370                 375                 380

Ala Ala Thr Gly Thr Tyr Ala Ser Gly Ser Thr Thr Phe Asn Ala Ile
385                 390                 395                 400

Ile Ser Ala Val Lys Thr Tyr Ala Asp Gly Tyr Val Ser Ile Val Gln
            405                 410                 415

Ser His Ser Tyr Ala Asn Gly Ser Leu Ser Glu Gln Phe Asp Arg Thr
```

420                 425                 430
Thr Gly Leu Ser Ile Ser Ala Arg Asp Leu Thr Trp Ser Tyr Ala Ala
            435                 440                 445

Leu Leu Thr Ala Asn Asp Arg Arg Asn Gly Val Val Pro Pro Ser Trp
    450                 455                 460

Gly Ala Ser Ser Ala Asn Ser Ile Pro Gly Ser Cys Ser Met Gly Ser
465                 470                 475                 480

Ala Thr Gly Ser Tyr Ala Thr Pro Ser Val Gly Ser Trp Pro Ala Thr
                485                 490                 495

Leu Thr Ser Gly Thr Ala Ala Pro
            500

<210> SEQ ID NO 16
<211> LENGTH: 105
<212> TYPE: PRT
<213> ORGANISM: Artificial Sequence
<220> FEATURE:
<223> OTHER INFORMATION: Starch binding domain of SEQ ID NO: 5

<400> SEQUENCE: 16

Pro Thr Ala Val Ala Val Thr Phe Asp Glu Ile Ala Thr Thr Thr Phe
1               5                   10                  15

Gly Glu Asn Val Tyr Leu Val Gly Ser Ile Ser Gln Leu Gly Asn Trp
            20                  25                  30

Asn Thr Ala Asn Gly Ile Pro Leu Ser Ala Ser Lys Tyr Thr Ser Ser
        35                  40                  45

Asn Pro Leu Trp Tyr Ala Thr Val Asn Leu Pro Ala Gly Thr Thr Phe
    50                  55                  60

Gln Tyr Lys Tyr Phe Arg Lys Glu Ser Asp Gly Ser Ile Lys Trp Glu
65                  70                  75                  80

Ser Asp Pro Asn Arg Ser Tyr Thr Val Pro Ala Lys Cys Gly Thr Thr
                85                  90                  95

Thr Ala Thr Glu Asn Asp Thr Trp Arg
            100                 105

<210> SEQ ID NO 17
<211> LENGTH: 485
<212> TYPE: PRT
<213> ORGANISM: Artificial Sequence
<220> FEATURE:
<223> OTHER INFORMATION: Catalytic domain of SEQ ID NO: 6

<400> SEQUENCE: 17

Ala Pro Gln Leu Ser Pro Arg Ala Thr Ser Leu Asp Ser Trp Leu Ser
1               5                   10                  15

Ser Glu Thr Thr Phe Ser Leu Asn Gly Ile Leu Ala Asn Ile Gly Ser
            20                  25                  30

Ser Gly Ala Tyr Ser Lys Ser Ala Ala Ser Gly Ala Val Ile Ala Ser
        35                  40                  45

Pro Ser Thr Ser Asn Pro Asp Tyr Tyr Tyr Thr Trp Thr Arg Asp Ala
    50                  55                  60

Ala Leu Thr Leu Lys Ala Leu Val Asp Ile Phe Arg Asn Gly Asn Leu
65                  70                  75                  80

Gly Leu Gln Thr Val Ile Glu Gln Tyr Val Asn Ala Gln Ala Lys Leu
                85                  90                  95

Gln Thr Val Ser Asn Pro Ser Gly Gly Leu Ser Asp Gly Ala Gly Leu
            100                 105                 110

Gly Glu Pro Lys Phe Asn Val Asp Leu Ser Ala Phe Thr Gly Ala Trp
            115                 120                 125

Gly Arg Pro Gln Arg Asp Gly Pro Ala Leu Arg Ala Ile Ala Leu Ile
130                 135                 140

Asp Phe Gly Asn Trp Leu Ile Asp Asn Gly Tyr Lys Ser Tyr Ala Val
145                 150                 155                 160

Asn Asn Val Trp Pro Ile Val Arg Asn Asp Leu Ala Tyr Val Ala Gln
                165                 170                 175

Tyr Trp Ser Gln Ser Gly Phe Asp Leu Trp Glu Glu Val Asn Ser Met
            180                 185                 190

Ser Phe Phe Thr Val Ala Asn Gln His Arg Ser Leu Val Glu Gly Ser
            195                 200                 205

Ala Phe Ala Ser Arg Val Gly Ala Ser Cys Ser Gly Cys Asp Ser Gln
210                 215                 220

Ala Pro Gln Ile Leu Cys Tyr Met Gln Ser Phe Trp Thr Gly Ser Tyr
225                 230                 235                 240

Ile Asn Ala Asn Thr Gly Gly Arg Ser Gly Lys Asp Ser Asn Thr
                245                 250                 255

Ile Leu Ala Ser Ile His Thr Phe Asp Pro Ala Ala Ser Cys Asp Asp
            260                 265                 270

Val Thr Phe Gln Pro Cys Ser Ser Arg Ala Leu Ala Asn His Lys Val
            275                 280                 285

Tyr Thr Asp Ser Phe Arg Ser Val Tyr Ala Leu Asn Ser Gly Ile Ala
            290                 295                 300

Gln Gly Lys Ala Val Ser Val Gly Arg Tyr Pro Glu Asp Ser Tyr Tyr
305                 310                 315                 320

Gly Gly Asn Pro Trp Phe Leu Ser Asn Leu Ala Ala Ala Glu Gln Leu
                325                 330                 335

Tyr Asp Ala Ile Tyr Gln Trp Asn Lys Ile Gly Ser Ile Thr Ile Thr
            340                 345                 350

Ser Thr Ser Leu Ala Phe Phe Lys Asp Val Tyr Pro Ser Ala Ala Thr
            355                 360                 365

Gly Thr Tyr Ala Ser Gly Ser Thr Thr Phe Asn Ala Ile Ile Ser Ala
370                 375                 380

Val Lys Thr Tyr Ala Asp Gly Tyr Val Ser Ile Val Gln Ser His Ser
385                 390                 395                 400

Tyr Ala Asn Gly Ser Leu Ser Glu Gln Phe Asp Arg Thr Thr Gly Leu
                405                 410                 415

Ser Ile Ser Ala Arg Asp Leu Thr Trp Ser Tyr Ala Ala Leu Leu Thr
            420                 425                 430

Ala Asn Asp Arg Arg Asn Gly Val Val Pro Pro Ser Trp Gly Ala Ser
            435                 440                 445

Ser Ala Asn Ser Ile Pro Gly Ser Cys Ser Met Gly Ser Ala Thr Gly
450                 455                 460

Ser Tyr Ala Thr Pro Ser Val Gly Ser Trp Pro Ala Thr Leu Thr Ser
465                 470                 475                 480

Gly Thr Ala Ala Pro
            485

<210> SEQ ID NO 18
<211> LENGTH: 105
<212> TYPE: PRT
<213> ORGANISM: Artificial Sequence
<220> FEATURE:
<223> OTHER INFORMATION: Starch binding domain of SEQ ID NO: 6

<400> SEQUENCE: 18

| Pro | Thr | Ala | Val | Ala | Val | Thr | Phe | Asp | Glu | Ile | Ala | Thr | Thr | Thr | Phe |
|---|---|---|---|---|---|---|---|---|---|---|---|---|---|---|---|
| 1 | | | | 5 | | | | | 10 | | | | | 15 | |

Gly Glu Asn Val Tyr Leu Val Gly Ser Ile Ser Gln Leu Gly Asn Trp
            20                25                30

Asn Thr Ala Asn Gly Ile Pro Leu Ser Ala Ser Lys Tyr Thr Ser Ser
        35                  40              45

Asn Pro Leu Trp Tyr Ala Thr Val Asn Leu Pro Ala Gly Thr Thr Phe
  50                    55              60

Gln Tyr Lys Tyr Phe Arg Lys Glu Ser Asp Gly Ser Ile Lys Trp Glu
65              70              75             80

Ser Asp Pro Asn Arg Ser Tyr Thr Val Pro Ala Lys Cys Gly Thr Thr
            85              90             95

Thr Ala Thr Glu Asn Asp Thr Trp Arg
        100            105

<210> SEQ ID NO 19
<211> LENGTH: 616
<212> TYPE: PRT
<213> ORGANISM: Penicillium oxalicum

<400> SEQUENCE: 19

Ala Pro Gln Leu Ser Pro Arg Ala Thr Ser Leu Asp Ser Trp Leu Ser
1              5                10              15

Ser Glu Thr Thr Phe Ser Leu Asn Gly Ile Leu Ala Asn Ile Gly Ser
            20                25              30

Ser Gly Ala Tyr Ser Lys Ser Ala Ser Gly Ala Val Ile Ala Ser
        35                  40              45

Pro Ser Thr Ser Asn Pro Asp Tyr Tyr Tyr Thr Trp Thr Arg Asp Ala
  50                    55              60

Ala Leu Thr Leu Lys Ala Leu Val Asp Ile Phe Arg Asn Gly Asn Leu
65              70              75             80

Gly Leu Gln Thr Val Ile Glu Gln Tyr Val Asn Ala Gln Ala Lys Leu
            85              90             95

Gln Thr Val Ser Asn Pro Ser Gly Gly Leu Ser Asp Gly Ala Gly Leu
            100              105            110

Gly Glu Pro Lys Phe Asn Val Asp Leu Ser Ala Phe Thr Gly Ala Trp
        115                120            125

Gly Arg Pro Gln Arg Asp Gly Pro Ala Leu Arg Ala Ile Ala Leu Ile
        130                135            140

Asp Phe Gly Asn Trp Leu Ile Asp Asn Gly Tyr Lys Ser Tyr Ala Val
145             150              155            160

Asn Asn Val Trp Pro Ile Val Arg Asn Asp Leu Ala Tyr Val Ala Gln
            165              170            175

Tyr Trp Ser Gln Ser Gly Phe Asp Leu Trp Glu Glu Val Asn Ser Met
        180                185            190

Ser Phe Phe Thr Val Ala Asn Gln His Arg Ser Leu Val Glu Gly Ser
        195                200            205

Ala Phe Ala Ser Arg Val Gly Ala Ser Cys Ser Gly Cys Asp Ser Gln
        210                215            220

Ala Pro Gln Ile Leu Cys Tyr Met Gln Ser Phe Trp Thr Gly Ser Tyr
225             230              235            240

Ile Asn Ala Asn Thr Gly Gly Arg Ser Gly Lys Asp Ser Asn Thr
            245              250            255

```
Ile Leu Ala Ser Ile His Thr Phe Asp Pro Ala Ala Ser Cys Asp Asp
            260                 265                 270

Val Thr Phe Gln Pro Cys Ser Arg Ala Leu Ala Asn His Lys Val
        275                 280                 285

Tyr Thr Asp Ser Phe Arg Ser Val Tyr Ala Leu Asn Ser Gly Ile Ala
        290                 295                 300

Gln Gly Lys Ala Val Ser Val Gly Arg Tyr Pro Glu Asp Ser Tyr Tyr
305                 310                 315                 320

Gly Gly Asn Pro Trp Phe Leu Ser Asn Leu Ala Ala Glu Gln Leu
                325                 330                 335

Tyr Asp Ala Ile Tyr Gln Trp Asn Lys Ile Gly Ser Ile Thr Ile Thr
            340                 345                 350

Ser Thr Ser Leu Ala Phe Phe Lys Asp Val Tyr Pro Ser Ala Ala Thr
        355                 360                 365

Gly Thr Tyr Ala Ser Gly Ser Thr Thr Phe Asn Ala Ile Ile Ser Ala
    370                 375                 380

Val Lys Thr Tyr Ala Asp Gly Tyr Val Ser Ile Val Gln Ser His Ser
385                 390                 395                 400

Tyr Ala Asn Gly Ser Leu Ser Glu Gln Phe Asp Arg Thr Thr Gly Leu
                405                 410                 415

Ser Ile Ser Ala Arg Asp Leu Thr Trp Ser Tyr Ala Ala Leu Leu Thr
            420                 425                 430

Ala Asn Asp Arg Arg Asn Gly Val Val Pro Pro Ser Trp Gly Ala Ser
        435                 440                 445

Ser Ala Asn Ser Ile Pro Gly Ser Cys Ser Met Gly Ser Ala Thr Gly
    450                 455                 460

Ser Tyr Ala Thr Pro Ser Val Gly Ser Trp Pro Ala Thr Leu Thr Ser
465                 470                 475                 480

Gly Thr Ala Ala Pro Ser Ser Thr Ser Thr Thr Lys Ala Pro Thr
                485                 490                 495

Thr Thr Thr Ala Thr Thr Thr Ser Ala Gly Ser Cys Thr Thr Pro
            500                 505                 510

Thr Ala Val Ala Val Thr Phe Asp Glu Ile Ala Thr Thr Thr Phe Gly
        515                 520                 525

Glu Asn Val Tyr Leu Val Gly Ser Ile Ser Gln Leu Gly Asn Trp Asn
    530                 535                 540

Thr Ala Asn Gly Ile Pro Leu Ser Ala Ser Lys Tyr Thr Ser Ser Asn
545                 550                 555                 560

Pro Leu Trp Tyr Ala Thr Val Asn Leu Pro Ala Gly Thr Thr Phe Gln
                565                 570                 575

Tyr Lys Tyr Phe Arg Lys Glu Ser Asp Gly Ser Ile Lys Trp Glu Ser
            580                 585                 590

Asp Pro Asn Arg Ser Tyr Thr Val Pro Ala Lys Cys Gly Thr Thr Thr
        595                 600                 605

Ala Thr Glu Asn Asp Thr Trp Arg
    610                 615

<210> SEQ ID NO 20
<211> LENGTH: 1851
<212> TYPE: DNA
<213> ORGANISM: Penicillium oxalicum

<400> SEQUENCE: 20
gctccacaat tgtctccaag agctacttct ttggattctt ggttgtcatc tgaaaccacc        60
```

```
ttttctttga acggtatctt ggctaatatc ggttcttctg gtgcttactc taaatctgct      120
gcttcaggtg ctgttattgc ttctccatct acttctaatc cagactacta ttacacttgg      180
actagagatg ctgctttgac tttgaaagct ttggttgaca ttttccgtaa tggtaacttg      240
ggcttgcaaa ccgttattga acaatacgtt aatgcccaag ctaagttgca aactgtttca      300
aatccatctg gtggtttgtc tgatggtgct ggtttgggtg aacctaagtt taatgttgat      360
ttgtctgctt tcactggtgc ttggggtaga ccacaaagag atggtccagc tttgagagct      420
attgctttga ttgattttgg caactggttg atcgataacg ctacaaatc ttacgctgtt       480 aacaatgttt ggcccatcgt tagaaatgat ttggcttatg ttgctcagta ctggtcccaa      540
tctggttttg atttgtggga agaagtcaac tccatgtctt ttttcaccgt tgccaatcaa      600
cacagatcat tggttgaagg ttctgctttt gcttctagag ttggtgcttc ttgttctggt      660
tgtgattctc aagctccaca aattttgtgc tacatgcaat cttttggac cggctcttac       720 attaacgcta atactggtgg tggtagatct ggtaaagatt ccaacactat tttggcctcc      780
attcatactt ttgatccagc tgcttcatgt gatgatgtta cttttcaacc atgttcctct      840
agagctttgg ctaaccataa ggtttacacc gattctttca gatccgttta cgctttgaat      900
tccggtattg ctcaaggtaa agctgtttct gttggtagat atccagagga ttcttactat      960
ggtggtaatc catggttctt gtctaatttg gctgctgctg aacaattata cgatgcaatc     1020
taccaatgga acaagatcgg ttccattact attacctcta cctctttggc tttcttcaag     1080
gatgtttatc catcagctgc tactggtact tatgcttctg gttctactac tttcaacgcc     1140
attatttctg ctgttaagac ttacgctgat ggctacgttt ctatcgttca atctcattct     1200
tacgccaacg gttctttgtc cgaacaattt gatagaacta ccggcttgtc tatttccgct     1260
agagatttga cttggtctta tgcagctttg ttgactgcca atgatagaag aaatggtgtt     1320
gttcctcctt cttggggtgc ttcatctgct aattctattc caggttcatg ttctatgggt     1380
tctgctacag gttcttacgc tactccatca gttggttctt ggccagctac tttgacttct     1440
ggtactgctg ctccatcttc tacttcaact actacaaaag ctccaactac cactactgct     1500
actacaacta catctgctgg ttcatgtact actccaactc tgttgctgt tactttcgac      1560 gaaattgcta ctactacctt cggtgaaaac gtttacttgg ttggttccat ctctcaatta     1620
ggtaattgga atactgccaa cggtattcca ttatccgctt ctaagtacac ttcttctaac     1680
ccattgtggt acgctactgt taatttgcca gctggtacta cttttcagta caagtacttc     1740
agaaaagagt ccgacggttc tattaagtgg gaatctgatc aaacagatc ttacactgtt      1800 ccagctaaat gtggtactac aaccgctact gaaaatgaca cttggagatg a              1851
```

<210> SEQ ID NO 21
<211> LENGTH: 92
<212> TYPE: PRT
<213> ORGANISM: Artificial Sequence
<220> FEATURE:
<223> OTHER INFORMATION: Hybrid signal sequence between the OST1 signal
      sequence and the mutated alpha mating factor protein signal
      sequence

<400> SEQUENCE: 21

Met Arg Gln Val Trp Phe Ser Trp Ile Val Gly Leu Phe Leu Cys Phe
1               5                   10                  15

Phe Asn Val Ser Ser Ala Ala Pro Val Asn Thr Thr Thr Glu Asp Glu
            20                  25                  30

```
Thr Ala Gln Ile Pro Ala Glu Ala Val Ile Gly Tyr Ser Asp Leu Glu
        35                  40                  45

Gly Asp Phe Asp Val Ala Val Leu Pro Phe Ser Asn Ser Thr Asn Asn
 50                  55                  60

Gly Leu Leu Phe Ile Asn Thr Thr Ile Ala Ser Ile Ala Ala Lys Glu
 65                  70                  75                  80

Glu Gly Val Ser Leu Glu Lys Arg Glu Ala Glu Ala
                85                  90

<210> SEQ ID NO 22
<211> LENGTH: 276
<212> TYPE: DNA
<213> ORGANISM: Artificial Sequence
<220> FEATURE:
<223> OTHER INFORMATION: Encoding SEQ ID NO: 21

<400> SEQUENCE: 22
atgagacaag tttggttctc ttggatcgtt ggtttgttct tgtgtttctt caacgtttct      60
tctgctgctc cagttaacac tactactgaa gacgaaactg ctcaaatccc agctgaagct     120
gttatcggtt actctgactt ggaaggtgac ttcgacgttg ctgttttgcc attctctaac     180
tctactaaca acggtttgtt gttcatcaac actactatcg cttctatcgc tgctaaggaa     240
gaaggtgttt ctttggaaaa gagagaagct gaagct                               276

<210> SEQ ID NO 23
<211> LENGTH: 22
<212> TYPE: PRT
<213> ORGANISM: Artificial Sequence
<220> FEATURE:
<223> OTHER INFORMATION: OST1 signal sequence

<400> SEQUENCE: 23

Met Arg Gln Val Trp Phe Ser Trp Ile Val Gly Leu Phe Leu Cys Phe
 1               5                  10                  15

Phe Asn Val Ser Ser Ala
            20

<210> SEQ ID NO 24
<211> LENGTH: 70
<212> TYPE: PRT
<213> ORGANISM: Artificial Sequence
<220> FEATURE:
<223> OTHER INFORMATION: Mutated alpha mating factor protein signal
      sequence without first level signal sequence

<400> SEQUENCE: 24

Ala Pro Val Asn Thr Thr Thr Glu Asp Glu Thr Ala Gln Ile Pro Ala
 1               5                  10                  15

Glu Ala Val Ile Gly Tyr Ser Asp Leu Glu Gly Asp Phe Asp Val Ala
                20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Leu Glu
 50                  55                  60

Lys Arg Glu Ala Glu Ala
 65                  70

<210> SEQ ID NO 25
<211> LENGTH: 85
<212> TYPE: PRT
<213> ORGANISM: Artificial Sequence
```

-continued

```
<220> FEATURE:
<223> OTHER INFORMATION: Wild-type alpha mating factor protein signal
      sequence with first level signal sequence

<400> SEQUENCE: 25

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg
                85

<210> SEQ ID NO 26
<211> LENGTH: 19
<212> TYPE: PRT
<213> ORGANISM: Artificial Sequence
<220> FEATURE:
<223> OTHER INFORMATION: Alpha mating factor first level signal sequence

<400> SEQUENCE: 26

Met Arg Phe Pro Ser Ile Phe Thr Ala Val Leu Phe Ala Ala Ser Ser
1               5                   10                  15

Ala Leu Ala

<210> SEQ ID NO 27
<211> LENGTH: 66
<212> TYPE: PRT
<213> ORGANISM: Artificial Sequence
<220> FEATURE:
<223> OTHER INFORMATION: Wild-type alpha mating factor protein signal
      sequence without first level signal sequence

<400> SEQUENCE: 27

Ala Pro Val Asn Thr Thr Thr Glu Asp Glu Thr Ala Gln Ile Pro Ala
1               5                   10                  15

Glu Ala Val Ile Gly Tyr Leu Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Leu Asp
    50                  55                  60

Lys Arg
65

<210> SEQ ID NO 28
<211> LENGTH: 19
<212> TYPE: PRT
<213> ORGANISM: Artificial Sequence
<220> FEATURE:
<223> OTHER INFORMATION: Penicillium oxalicum glucoamylase native signal
      sequence

<400> SEQUENCE: 28

Met Ser Arg Leu Leu Tyr Ala Leu Gly Ala Leu Ala Val Gly Gln Ser
1               5                   10                  15
```

Ala Leu Ala

<210> SEQ ID NO 29
<211> LENGTH: 708
<212> TYPE: PRT
<213> ORGANISM: Artificial Sequence
<220> FEATURE:
<223> OTHER INFORMATION: Penicillium oxalicum glucoamylase with hybrid
      OST1/aMF signal sequence

<400> SEQUENCE: 29

```
Met Arg Gln Val Trp Phe Ser Trp Ile Val Gly Leu Phe Leu Cys Phe
1               5                   10                  15

Phe Asn Val Ser Ser Ala Ala Pro Val Asn Thr Thr Thr Glu Asp Glu
            20                  25                  30

Thr Ala Gln Ile Pro Ala Glu Ala Val Ile Gly Tyr Ser Asp Leu Glu
        35                  40                  45

Gly Asp Phe Asp Val Ala Val Leu Pro Phe Ser Asn Ser Thr Asn Asn
    50                  55                  60

Gly Leu Leu Phe Ile Asn Thr Thr Ile Ala Ser Ile Ala Ala Lys Glu
65                  70                  75                  80

Glu Gly Val Ser Leu Glu Lys Arg Glu Ala Glu Ala Pro Gln Leu
                85                  90                  95

Ser Pro Arg Ala Thr Ser Leu Asp Ser Trp Leu Ser Ser Glu Thr Thr
            100                 105                 110

Phe Ser Leu Asn Gly Ile Leu Ala Asn Ile Gly Ser Ser Gly Ala Tyr
        115                 120                 125

Ser Lys Ser Ala Ala Ser Gly Ala Val Ile Ala Ser Pro Ser Thr Ser
130                 135                 140

Asn Pro Asp Tyr Tyr Tyr Thr Trp Thr Arg Asp Ala Ala Leu Thr Leu
145                 150                 155                 160

Lys Ala Leu Val Asp Ile Phe Arg Asn Gly Asn Leu Gly Leu Gln Thr
                165                 170                 175

Val Ile Glu Gln Tyr Val Asn Ala Gln Ala Lys Leu Gln Thr Val Ser
            180                 185                 190

Asn Pro Ser Gly Gly Leu Ser Asp Gly Ala Gly Leu Gly Glu Pro Lys
        195                 200                 205

Phe Asn Val Asp Leu Ser Ala Phe Thr Gly Ala Trp Gly Arg Pro Gln
    210                 215                 220

Arg Asp Gly Pro Ala Leu Arg Ala Ile Ala Leu Ile Asp Phe Gly Asn
225                 230                 235                 240

Trp Leu Ile Asp Asn Gly Tyr Lys Ser Tyr Ala Val Asn Asn Val Trp
                245                 250                 255

Pro Ile Val Arg Asn Asp Leu Ala Tyr Val Ala Gln Tyr Trp Ser Gln
            260                 265                 270

Ser Gly Phe Asp Leu Trp Glu Glu Val Asn Ser Met Ser Phe Phe Thr
        275                 280                 285

Val Ala Asn Gln His Arg Ser Leu Val Glu Gly Ser Ala Phe Ala Ser
    290                 295                 300

Arg Val Gly Ala Ser Cys Ser Gly Cys Asp Ser Gln Ala Pro Gln Ile
305                 310                 315                 320

Leu Cys Tyr Met Gln Ser Phe Trp Thr Gly Ser Tyr Ile Asn Ala Asn
                325                 330                 335

Thr Gly Gly Gly Arg Ser Gly Lys Asp Ser Asn Thr Ile Leu Ala Ser
            340                 345                 350
```

Ile His Thr Phe Asp Pro Ala Ser Cys Asp Val Thr Phe Gln
355                 360                 365

Pro Cys Ser Ser Arg Ala Leu Ala Asn His Lys Val Tyr Thr Asp Ser
370                 375                 380

Phe Arg Ser Val Tyr Ala Leu Asn Ser Gly Ile Ala Gln Gly Lys Ala
385                 390                 395                 400

Val Ser Val Gly Arg Tyr Pro Glu Asp Ser Tyr Gly Gly Asn Pro
                405                 410                 415

Trp Phe Leu Ser Asn Leu Ala Ala Ala Glu Gln Leu Tyr Asp Ala Ile
                420                 425                 430

Tyr Gln Trp Asn Lys Ile Gly Ser Ile Thr Ile Thr Ser Thr Ser Leu
                435                 440                 445

Ala Phe Phe Lys Asp Val Tyr Pro Ser Ala Ala Thr Gly Thr Tyr Ala
450                 455                 460

Ser Gly Ser Thr Thr Phe Asn Ala Ile Ile Ser Ala Val Lys Thr Tyr
465                 470                 475                 480

Ala Asp Gly Tyr Val Ser Ile Val Gln Ser His Ser Tyr Ala Asn Gly
                485                 490                 495

Ser Leu Ser Glu Gln Phe Asp Arg Thr Thr Gly Leu Ser Ile Ser Ala
                500                 505                 510

Arg Asp Leu Thr Trp Ser Tyr Ala Ala Leu Leu Thr Ala Asn Asp Arg
                515                 520                 525

Arg Asn Gly Val Val Pro Pro Ser Trp Gly Ala Ser Ser Ala Asn Ser
                530                 535                 540

Ile Pro Gly Ser Cys Ser Met Gly Ser Ala Thr Gly Ser Tyr Ala Thr
545                 550                 555                 560

Pro Ser Val Gly Ser Trp Pro Ala Thr Leu Thr Ser Gly Thr Ala Ala
                565                 570                 575

Pro Ser Ser Thr Ser Thr Thr Thr Lys Ala Pro Thr Thr Thr Thr Ala
                580                 585                 590

Thr Thr Thr Thr Ser Ala Gly Ser Cys Thr Thr Pro Thr Ala Val Ala
                595                 600                 605

Val Thr Phe Asp Glu Ile Ala Thr Thr Thr Phe Gly Glu Asn Val Tyr
610                 615                 620

Leu Val Gly Ser Ile Ser Gln Leu Gly Asn Trp Asn Thr Ala Asn Gly
625                 630                 635                 640

Ile Pro Leu Ser Ala Ser Lys Tyr Thr Ser Ser Asn Pro Leu Trp Tyr
                645                 650                 655

Ala Thr Val Asn Leu Pro Ala Gly Thr Thr Phe Gln Tyr Lys Tyr Phe
                660                 665                 670

Arg Lys Glu Ser Asp Gly Ser Ile Lys Trp Glu Ser Asp Pro Asn Arg
                675                 680                 685

Ser Tyr Thr Val Pro Ala Lys Cys Gly Thr Thr Ala Thr Glu Asn
                690                 695                 700

Asp Thr Trp Arg
705

<210> SEQ ID NO 30
<211> LENGTH: 2127
<212> TYPE: DNA
<213> ORGANISM: Artificial Sequence
<220> FEATURE:
<223> OTHER INFORMATION: Encoding SEQ ID NO: 29

<400> SEQUENCE: 30

```
atgagacaag tttggttctc ttggatcgtt ggtttgttct tgtgtttctt caacgtttct    60
tctgctgctc cagttaacac tactactgaa gacgaaactg ctcaaatccc agctgaagct   120
gttatcggtt actctgactt ggaaggtgac ttcgacgttg ctgttttgcc attctctaac   180
tctactaaca acgtttgtt gttcatcaac actactatcg cttctatcgc tgctaaggaa   240
gaaggtgttt cttttggaaaa gagagaagct gaagctgctc acaattgtc tccaagagct   300
acttcttttgg attcttggtt gtcatctgaa accaccttttt ctttgaacgg tatcttggct   360
aatatcggtt cttctggtgc ttactctaaa tctgctgctt caggtgctgt tattgcttct   420
ccatctactt ctaatccaga ctactattac acttggacta gagatgctgc tttgactttg   480
aaagctttgg ttgacatttt ccgtaatggt aacttgggct gcaaaccgt tattgaacaa   540
tacgttaatg cccaagctaa gttgcaaact gtttcaaatc catctggtgg tttgtctgat   600
ggtgctggtt tgggtgaacc taagtttaat gttgatttgt ctgctttcac tggtgcttgg   660
ggtagaccac aaagagatgg tccagctttg agagctattg ctttgattga ttttggcaac   720
tggttgatcg ataacggcta caaatcttac gctgttaaca atgtttggcc catcgttaga   780
aatgatttgg cttatgttgc tcagtactgg tcccaatctg gttttgattt gtgggaagaa   840
gtcaactcca tgtctttttt caccgttgcc aatcaacaca gatcattggt tgaaggttct   900
gcttttgctt ctagagttgg tgcttcttgt tctggttgtg attctcaagc tccacaaatt   960
ttgtgctaca tgcaatcttt ttggaccggc tcttacatta acgctaatac tggtggtggt  1020
agatctggta agattccaa cactattttg gcctccattc atactttga tccagctgct  1080
tcatgtgatg atgttacttt tcaaccatgt tcctctagag ctttggctaa ccataaggtt  1140
tacaccgatt ctttcagatc cgtttacgct ttgaattccg gtattgctca aggtaaagct  1200
gtttctgttg gtagatatcc agaggattct tactatggtg gtaatccatg gttcttgtct  1260
aatttggctg ctgctgaaca attatacgat gcaatctacc aatggaacaa gatcggttcc  1320
attactatta cctctacctc tttggctttc ttcaaggatg tttatccatc agctgctact  1380
ggtacttatg cttctggttc tactactttc aacgccatta tttctgctgt taagacttac  1440
gctgatggct acgtttctat cgttcaatct cattcttacg ccaacggttc tttgtccgaa  1500
caatttgata gaactaccgg cttgtctatt tccgctagag atttgacttg gtcttatgca  1560
gctttgttga ctgccaatga tagaagaaat ggtgttgttc ctccttcttg gggtgcttca  1620
tctgctaatt ctattccagg ttcatgttct atgggttctg ctacaggttc ttacgctact  1680
ccatcagttg gttcttggcc agctactttg acttctggta ctgctgctcc atcttctact  1740
tcaactacta caaaagctcc aactaccact actgctacta caactacatc tgctggttca  1800
tgtactactc caactgctgt tgctgttact ttcgacgaaa ttgctactac taccttcggt  1860
gaaaacgttt acttggttgg ttccatctct caattaggta attggaatac tgccaacggt  1920
attccattat ccgcttctaa gtacacttct tctaacccat gtggtacgc tactgttaat  1980
ttgccagctg gtactacttt tcagtacaag tacttcaaga aagagtccga cggttctatt  2040
aagtgggaat ctgatccaaa cagatcttac actgttccag ctaaatgtgg tactacaacc  2100
gctactgaaa atgacacttg gagatga                                       2127
```

<210> SEQ ID NO 31
<211> LENGTH: 701
<212> TYPE: PRT
<213> ORGANISM: Artificial Sequence
<220> FEATURE:
<223> OTHER INFORMATION: Penicillium oxalicum glucoamylase with wildtype alpha mating factor signal sequence with first level signal
sequence

<400> SEQUENCE: 31

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Ala Pro Gln Leu Ser Pro Arg Ala Thr Ser Leu
                85                  90                  95

Asp Ser Trp Leu Ser Ser Glu Thr Thr Phe Ser Leu Asn Gly Ile Leu
            100                 105                 110

Ala Asn Ile Gly Ser Ser Gly Ala Tyr Ser Lys Ser Ala Ala Ser Gly
        115                 120                 125

Ala Val Ile Ala Ser Pro Ser Thr Ser Asn Pro Asp Tyr Tyr Tyr Thr
    130                 135                 140

Trp Thr Arg Asp Ala Ala Leu Thr Leu Lys Ala Leu Val Asp Ile Phe
145                 150                 155                 160

Arg Asn Gly Asn Leu Gly Leu Gln Thr Val Ile Glu Gln Tyr Val Asn
                165                 170                 175

Ala Gln Ala Lys Leu Gln Thr Val Ser Asn Pro Ser Gly Gly Leu Ser
            180                 185                 190

Asp Gly Ala Gly Leu Gly Glu Pro Lys Phe Asn Val Asp Leu Ser Ala
        195                 200                 205

Phe Thr Gly Ala Trp Gly Arg Pro Gln Arg Asp Gly Pro Ala Leu Arg
    210                 215                 220

Ala Ile Ala Leu Ile Asp Phe Gly Asn Trp Leu Ile Asp Asn Gly Tyr
225                 230                 235                 240

Lys Ser Tyr Ala Val Asn Asn Val Trp Pro Ile Val Arg Asn Asp Leu
                245                 250                 255

Ala Tyr Val Ala Gln Tyr Trp Ser Gln Ser Gly Phe Asp Leu Trp Glu
            260                 265                 270

Glu Val Asn Ser Met Ser Phe Phe Thr Val Ala Asn Gln His Arg Ser
        275                 280                 285

Leu Val Glu Gly Ser Ala Phe Ala Ser Arg Val Gly Ala Ser Cys Ser
    290                 295                 300

Gly Cys Asp Ser Gln Ala Pro Gln Ile Leu Cys Tyr Met Gln Ser Phe
305                 310                 315                 320

Trp Thr Gly Ser Tyr Ile Asn Ala Asn Thr Gly Gly Arg Ser Gly
                325                 330                 335

Lys Asp Ser Asn Thr Ile Leu Ala Ser Ile His Thr Phe Asp Pro Ala
            340                 345                 350

Ala Ser Cys Asp Asp Val Thr Phe Gln Pro Cys Ser Ser Arg Ala Leu
        355                 360                 365

Ala Asn His Lys Val Tyr Thr Asp Ser Phe Arg Ser Val Tyr Ala Leu
    370                 375                 380

Asn Ser Gly Ile Ala Gln Gly Lys Ala Val Ser Val Gly Arg Tyr Pro
385                 390                 395                 400

Glu Asp Ser Tyr Tyr Gly Gly Asn Pro Trp Phe Leu Ser Asn Leu Ala
            405                 410                 415

Ala Ala Glu Gln Leu Tyr Asp Ala Ile Tyr Gln Trp Asn Lys Ile Gly
        420                 425                 430

Ser Ile Thr Ile Thr Ser Thr Leu Ala Phe Phe Lys Asp Val Tyr
            435                 440                 445

Pro Ser Ala Ala Thr Gly Thr Tyr Ala Ser Gly Ser Thr Thr Phe Asn
    450                 455                 460

Ala Ile Ile Ser Ala Val Lys Thr Tyr Ala Asp Gly Tyr Val Ser Ile
465                 470                 475                 480

Val Gln Ser His Ser Tyr Ala Asn Gly Ser Leu Ser Glu Gln Phe Asp
                485                 490                 495

Arg Thr Thr Gly Leu Ser Ile Ser Ala Arg Asp Leu Thr Trp Ser Tyr
            500                 505                 510

Ala Ala Leu Leu Thr Ala Asn Asp Arg Arg Asn Gly Val Val Pro Pro
        515                 520                 525

Ser Trp Gly Ala Ser Ser Ala Asn Ser Ile Pro Gly Ser Cys Ser Met
    530                 535                 540

Gly Ser Ala Thr Gly Ser Tyr Ala Thr Pro Ser Val Gly Ser Trp Pro
545                 550                 555                 560

Ala Thr Leu Thr Ser Gly Thr Ala Ala Pro Ser Ser Thr Ser Thr Thr
                565                 570                 575

Thr Lys Ala Pro Thr Thr Thr Ala Thr Thr Thr Ser Ala Gly
            580                 585                 590

Ser Cys Thr Thr Pro Thr Ala Val Ala Val Thr Phe Asp Glu Ile Ala
                595                 600                 605

Thr Thr Thr Phe Gly Glu Asn Val Tyr Leu Val Gly Ser Ile Ser Gln
    610                 615                 620

Leu Gly Asn Trp Asn Thr Ala Asn Gly Ile Pro Leu Ser Ala Ser Lys
625                 630                 635                 640

Tyr Thr Ser Ser Asn Pro Leu Trp Tyr Ala Thr Val Asn Leu Pro Ala
                645                 650                 655

Gly Thr Thr Phe Gln Tyr Lys Tyr Phe Arg Lys Glu Ser Asp Gly Ser
            660                 665                 670

Ile Lys Trp Glu Ser Asp Pro Asn Arg Ser Tyr Thr Val Pro Ala Lys
        675                 680                 685

Cys Gly Thr Thr Thr Ala Thr Glu Asn Asp Thr Trp Arg
    690                 695                 700

<210> SEQ ID NO 32
<211> LENGTH: 638
<212> TYPE: PRT
<213> ORGANISM: Artificial Sequence
<220> FEATURE:
<223> OTHER INFORMATION: Penicillium oxalicum glucoamylase with OST1
      signal sequence

<400> SEQUENCE: 32

Met Arg Gln Val Trp Phe Ser Trp Ile Val Gly Leu Phe Leu Cys Phe
1               5                   10                  15

Phe Asn Val Ser Ser Ala Ala Pro Gln Leu Ser Pro Arg Ala Thr Ser
            20                  25                  30

Leu Asp Ser Trp Leu Ser Glu Thr Thr Phe Ser Leu Asn Gly Ile
        35                  40                  45

Leu Ala Asn Ile Gly Ser Ser Gly Ala Tyr Ser Lys Ser Ala Ala Ser

```
                 50                  55                  60
Gly Ala Val Ile Ala Ser Pro Ser Thr Ser Asn Pro Asp Tyr Tyr Tyr
 65                  70                  75                  80

Thr Trp Thr Arg Asp Ala Ala Leu Thr Leu Lys Ala Leu Val Asp Ile
                 85                  90                  95

Phe Arg Asn Gly Asn Leu Gly Leu Gln Thr Val Ile Glu Gln Tyr Val
                100                 105                 110

Asn Ala Gln Ala Lys Leu Gln Thr Val Ser Asn Pro Ser Gly Gly Leu
                115                 120                 125

Ser Asp Gly Ala Gly Leu Gly Glu Pro Lys Phe Asn Val Asp Leu Ser
130                 135                 140

Ala Phe Thr Gly Ala Trp Gly Arg Pro Gln Arg Asp Gly Pro Ala Leu
145                 150                 155                 160

Arg Ala Ile Ala Leu Ile Asp Phe Gly Asn Trp Leu Ile Asp Asn Gly
                165                 170                 175

Tyr Lys Ser Tyr Ala Val Asn Asn Val Trp Pro Ile Val Arg Asn Asp
                180                 185                 190

Leu Ala Tyr Val Ala Gln Tyr Trp Ser Gln Ser Gly Phe Asp Leu Trp
                195                 200                 205

Glu Glu Val Asn Ser Met Ser Phe Phe Thr Val Ala Asn Gln His Arg
210                 215                 220

Ser Leu Val Glu Gly Ser Ala Phe Ala Ser Arg Val Gly Ala Ser Cys
225                 230                 235                 240

Ser Gly Cys Asp Ser Gln Ala Pro Gln Ile Leu Cys Tyr Met Gln Ser
                245                 250                 255

Phe Trp Thr Gly Ser Tyr Ile Asn Ala Asn Thr Gly Gly Arg Ser
                260                 265                 270

Gly Lys Asp Ser Asn Thr Ile Leu Ala Ser Ile His Thr Phe Asp Pro
                275                 280                 285

Ala Ala Ser Cys Asp Asp Val Thr Phe Gln Pro Cys Ser Ser Arg Ala
290                 295                 300

Leu Ala Asn His Lys Val Tyr Thr Asp Ser Phe Arg Ser Val Tyr Ala
305                 310                 315                 320

Leu Asn Ser Gly Ile Ala Gln Gly Lys Ala Val Ser Val Gly Arg Tyr
                325                 330                 335

Pro Glu Asp Ser Tyr Tyr Gly Gly Asn Pro Trp Phe Leu Ser Asn Leu
                340                 345                 350

Ala Ala Ala Glu Gln Leu Tyr Asp Ala Ile Tyr Gln Trp Asn Lys Ile
                355                 360                 365

Gly Ser Ile Thr Ile Thr Ser Thr Ser Leu Ala Phe Phe Lys Asp Val
370                 375                 380

Tyr Pro Ser Ala Ala Thr Gly Thr Tyr Ala Ser Gly Ser Thr Thr Phe
385                 390                 395                 400

Asn Ala Ile Ile Ser Ala Val Lys Thr Tyr Ala Asp Gly Tyr Val Ser
                405                 410                 415

Ile Val Gln Ser His Ser Tyr Ala Asn Gly Ser Leu Ser Glu Gln Phe
                420                 425                 430

Asp Arg Thr Thr Gly Leu Ser Ile Ser Ala Arg Asp Leu Thr Trp Ser
                435                 440                 445

Tyr Ala Ala Leu Leu Thr Ala Asn Asp Arg Arg Asn Gly Val Val Pro
450                 455                 460

Pro Ser Trp Gly Ala Ser Ser Ala Asn Ser Ile Pro Gly Ser Cys Ser
465                 470                 475                 480
```

Met Gly Ser Ala Thr Gly Ser Tyr Ala Thr Pro Ser Val Gly Ser Trp
                485                 490                 495

Pro Ala Thr Leu Thr Ser Gly Thr Ala Ala Pro Ser Ser Thr Ser Thr
            500                 505                 510

Thr Thr Lys Ala Pro Thr Thr Thr Thr Ala Thr Thr Thr Thr Ser Ala
        515                 520                 525

Gly Ser Cys Thr Thr Pro Thr Ala Val Ala Val Thr Phe Asp Glu Ile
    530                 535                 540

Ala Thr Thr Thr Phe Gly Glu Asn Val Tyr Leu Val Gly Ser Ile Ser
545                 550                 555                 560

Gln Leu Gly Asn Trp Asn Thr Ala Asn Gly Ile Pro Leu Ser Ala Ser
                565                 570                 575

Lys Tyr Thr Ser Ser Asn Pro Leu Trp Tyr Ala Thr Val Asn Leu Pro
            580                 585                 590

Ala Gly Thr Thr Phe Gln Tyr Lys Tyr Phe Arg Lys Glu Ser Asp Gly
        595                 600                 605

Ser Ile Lys Trp Glu Ser Asp Pro Asn Arg Ser Tyr Thr Val Pro Ala
    610                 615                 620

Lys Cys Gly Thr Thr Ala Thr Glu Asn Asp Thr Trp Arg
625                 630                 635

<210> SEQ ID NO 33
<211> LENGTH: 1512
<212> TYPE: DNA
<213> ORGANISM: Artificial Sequence
<220> FEATURE:
<223> OTHER INFORMATION: Encoding SEQ ID NO: 15

<400> SEQUENCE: 33
atgtccaggt tgttgtatgc tttgggtgct ttggctgttg gtcaatctgc tttagctgct        60
ccacaattgt ctccaagagc tacttctttg gattcttggt tgtcatctga accacccttt       120
tctttgaacg gtatcttggc taatatcggt tcttctggtg cttactctaa atctgctgct       180
tcaggtgctg ttattgcttc tccatctact tctaatccag actactatta cacttggact       240
agagatgctg ctttgacttt gaaagctttg gttgacattt ccgtaatgg taacttgggc        300 ttgcaaaccg ttattgaaca atacgttaat gcccaagcta agttgcaaac tgtttcaaat       360
ccatctggtg gtttgtctga tggtgctggt ttgggtgaac taagtttaa tgttgatttg        420 tctgctttca ctggtgcttg gggtagacca caaagagatg gtccagcttt gagagctatt       480
gctttgattg attttggcaa ctggttgatc gataacggct acaaatctta cgctgttaac       540
aatgtttggc ccatcgttag aaatgatttg gcttatgttg ctcagtactg gtcccaatct       600
ggttttgatt tgtgggaaga agtcaactcc atgtcttttt tcaccgttgc caatcaacac       660
agatcattgg ttgaaggttc tgcttttgct tctagagttg gtgcttcttg ttctggttgt       720
gattctcaag ctccacaaat tttgtgctac atgcaatctt tttggaccgg ctcttacatt       780
aacgctaata ctggtggtgg tagatctggt aaagattcca acactatttt ggcctccatt       840
catacttttg atccagctgc ttcatgtgat gatgttactt tcaaccatg ttcctctaga        900 gctttggcta accataaggt ttacaccgat tctttcagat ccgtttacgc tttgaattcc       960
ggtattgctc aaggtaaagc tgtttctgtt ggtagatatc agaggattc ttactatggt       1020 ggtaatccat ggttcttgtc taatttggct gctgctgaac aattatacga tgcaatctac      1080
caatggaaca gatcggttc cattactatt acctctacct ctttggcttt cttcaaggat       1140

| | |
|---|---:|
| gtttatccat cagctgctac tggtacttat gcttctggtt ctactacttt caacgccatt | 1200 |
| atttctgctg ttaagactta cgctgatggc tacgtttcta tcgttcaatc tcattcttac | 1260 |
| gccaacggtt ctttgtccga acaatttgat agaactaccg gcttgtctat tccgctaga | 1320 |
| gatttgactt ggtctatgc agctttgttg actgccaatg atagaagaaa tggtgttgtt | 1380 |
| cctccttctt ggggtgcttc atctgctaat tctattccag gttcatgttc tatgggttct | 1440 |
| gctacaggtt cttacgctac tccatcagtt ggttcttggc cagctacttt gacttctggt | 1500 |
| actgctgctc ca | 1512 |

<210> SEQ ID NO 34
<211> LENGTH: 1455
<212> TYPE: DNA
<213> ORGANISM: Artificial Sequence
<220> FEATURE:
<223> OTHER INFORMATION: Encoding SEQ ID NO: 17

<400> SEQUENCE: 34

| | |
|---|---:|
| gctccacaat tgtctccaag agctacttct ttggattctt ggttgtcatc tgaaaccacc | 60 |
| ttttctttga acggtatctt ggctaatatc ggttcttctg gtgcttactc taaatctgct | 120 |
| gcttcaggtg ctgttattgc ttctccatct acttctaatc cagactacta ttacacttgg | 180 |
| actagagatg ctgctttgac tttgaaagct ttggttgaca ttttccgtaa tggtaacttg | 240 |
| ggcttgcaaa ccgttattga acaatacgtt aatgcccaag ctaagttgca aactgtttca | 300 |
| aatccatctg gtggtttgtc tgatggtgct ggtttgggtg aacctaagtt taatgttgat | 360 |
| ttgtctgctt tcactggtgc ttggggtaga ccacaaagag atggtccagc tttgagagct | 420 |
| attgctttga ttgattttgg caactggttg atcgataacg ctacaaatc ttacgctgtt | 480 |
| aacaatgttt ggcccatcgt tagaaatgat ttggcttatg ttgctcagta ctggtcccaa | 540 |
| tctggttttg atttgtggga agaagtcaac tccatgtctt ttttcaccgt tgccaatcaa | 600 |
| cacagatcat tggttgaagg ttctgctttt gcttctagag ttggtgcttc ttgttctggt | 660 |
| tgtgattctc aagctccaca aattttgtgc tacatgcaat cttttttggac cggctcttac | 720 |
| attaacgcta atactggtgg tggtagatct ggtaaagatt ccaacactat tttggcctcc | 780 |
| attcatactt ttgatccagc tgcttcatgt gatgatgtta cttttcaacc atgttcctct | 840 |
| agagctttgg ctaaccataa ggtttacacc gattcttttca gatccgttta cgctttgaat | 900 |
| tccggtattg ctcaaggtaa agctgtttct gttggtagat atccagagga ttcttactat | 960 |
| ggtggtaatc catggttctt gtctaatttg gctgctgctg aacaattata cgatgcaatc | 1020 |
| taccaatgga acaagatcgg ttccattact attacctcta cctctttggc tttcttcaag | 1080 |
| gatgtttatc catcagctgc tactggtact tatgcttctg gttctactac tttcaacgcc | 1140 |
| attatttctg ctgttaagac ttacgctgat ggctacgttt ctatcgttca atctcattct | 1200 |
| tacgccaacg gttctttgtc cgaacaattt gatagaacta ccggcttgtc tatttccgct | 1260 |
| agagatttga cttggtctta tgcagctttg ttgactgcca atgatagaag aaatggtgtt | 1320 |
| gttcctcctt cttggggtgc ttcatctgct aattctattc caggttcatg ttctatgggt | 1380 |
| tctgctacag gttcttacgc tactccatca gttggttctt ggccagctac tttgacttct | 1440 |
| ggtactgctg ctcca | 1455 |

<210> SEQ ID NO 35
<211> LENGTH: 318
<212> TYPE: DNA
<213> ORGANISM: Artificial Sequence

```
<220> FEATURE:
<223> OTHER INFORMATION: Encoding SEQ ID NO: 16

<400> SEQUENCE: 35
ccaactgctg ttgctgttac tttcgacgaa attgctacta ctaccttcgg tgaaaacgtt      60
tacttggttg gttccatctc tcaattaggt aattggaata ctgccaacgg tattccatta     120
tccgcttcta agtacacttc ttctaaccca ttgtggtacg ctactgttaa tttgccagct     180
ggtactactt ttcagtacaa gtacttcaga aaagagtccg acggttctat taagtgggaa     240
tctgatccaa acagatctta cactgttcca gctaaatgtg gtactacaac cgctactgaa     300
aatgacactt ggagatga                                                  318

<210> SEQ ID NO 36
<211> LENGTH: 318
<212> TYPE: DNA
<213> ORGANISM: Artificial Sequence
<220> FEATURE:
<223> OTHER INFORMATION: Encoding SEQ ID NO: 18

<400> SEQUENCE: 36
ccaactgctg ttgctgttac tttcgacgaa attgctacta ctaccttcgg tgaaaacgtt      60
tacttggttg gttccatctc tcaattaggt aattggaata ctgccaacgg tattccatta     120
tccgcttcta agtacacttc ttctaaccca ttgtggtacg ctactgttaa tttgccagct     180
ggtactactt ttcagtacaa gtacttcaga aaagagtccg acggttctat taagtgggaa     240
tctgatccaa acagatctta cactgttcca gctaaatgtg gtactacaac cgctactgaa     300
aatgacactt ggagatga                                                  318

<210> SEQ ID NO 37
<211> LENGTH: 57
<212> TYPE: DNA
<213> ORGANISM: Artificial Sequence
<220> FEATURE:
<223> OTHER INFORMATION: Encoding SEQ ID NO: 28

<400> SEQUENCE: 37
atgtccaggt tgttgtatgc tttgggtgct ttggctgttg gtcaatctgc tttagct          57

<210> SEQ ID NO 38
<211> LENGTH: 2127
<212> TYPE: DNA
<213> ORGANISM: Artificial Sequence
<220> FEATURE:
<223> OTHER INFORMATION: Encoding SEQ ID NO: 29

<400> SEQUENCE: 38
atgagacaag tttggttctc ttggatcgtt ggtttgttct tgtgtttctt caacgtttct      60
tctgctgctc cagttaacac tactactgaa gacgaaactg ctcaaatccc agctgaagct     120
gttatcggtt actctgactt ggaaggtgac ttcgacgttg ctgttttgcc attctctaac     180
tctactaaca acggtttgtt gttcatcaac actactatcg cttctatcgc tgctaaggaa     240
gaaggtgttt ctttggaaaa gagagaagct gaagctgctc cacaattgtc tccaagagct     300
acttctttgg attcttggtt gtcatctgaa accacctttt ctttgaacgg tatcttggct     360
aatatcggtt cttctggtgc ttactctaaa tctgctgctt caggtgctgt tattgcttct     420
ccatctactt ctaatccaga ctactattac acttggacta gagatgctgc tttgactttg     480
aaagctttgg ttgacatttt ccgtaatggt aacttgggct tgcaaaccgt tattgaacaa     540
```

```
tacgttaatg cccaagctaa gttgcaaact gtttcaaatc catctggtgg tttgtctgat      600
ggtgctggtt tgggtgaacc taagtttaat gttgatttgt ctgctttcac tggtgcttgg      660
ggtagaccac aaagagatgg tccagctttg agagctattg ctttgattga ttttggcaac      720
tggttgatcg ataacggcta caaatcttac gctgttaaca atgtttggcc catcgttaga      780
aatgatttgg cttatgttgc tcagtactgg tcccaatctg gttttgattt gtgggaagaa      840
gtcaactcca tgtctttttt caccgttgcc aatcaacaca gatcattggt tgaaggttct      900
gcttttgctt ctagagttgg tgcttcttgt tctggttgtg attctcaagc tccacaaatt      960
ttgtgctaca tgcaatcttt ttggaccggc tcttacatta cgctaatac tggtggtggt     1020 agatctggta aagattccaa cactattttg gcctccattc atactttga tccagctgct     1080 tcatgtgatg atgttacttt tcaaccatgt tcctctagag ctttggctaa ccataaggtt     1140
tacaccgatt ctttcagatc cgtttacgct ttgaattccg gtattgctca aggtaaagct     1200
gtttctgttg gtagatatcc agaggattct tactatggtg gtaatccatg gttcttgtct     1260
aatttggctg ctgctgaaca attatacgat gcaatctacc aatggaacaa gatcggttcc     1320
attactatta cctctacctc tttggctttc ttcaaggatg tttatccatc agctgctact     1380
ggtacttatg cttctggttc tactactttc aacgccatta tttctgctgt taagacttac     1440
gctgatggct acgtttctat cgttcaatct cattcttacg ccaacggttc tttgtccgaa     1500
caatttgata gaactaccgg cttgtctatt ccgctagag atttgacttg gtcttatgca     1560
gctttgttga ctgccaatga tagaagaaat ggtgttgttc ctccttcttg gggtgcttca     1620
tctgctaatt ctattccagg ttcatgttct atgggtctg ctacaggttc ttacgctact     1680
ccatcagttg gttcttggcc agctactttg acttctggta ctgctgctcc atcttctact     1740
tcaactacta caaaagctcc aactaccact actgctacta caactacatc tgctggttca     1800
tgtactactc caactgctgt tgctgttact ttcgacgaaa ttgctactac taccttcggt     1860
gaaaacgttt acttggttgg ttccatctct caattaggta attggaatac tgccaacggt     1920
attccattat ccgcttctaa gtacacttct tctaacccat gtggtacgc tactgttaat     1980 ttgccagctg gtactacttt tcagtacaag tacttcagaa aagagtccga cggttctatt     2040
aagtgggaat ctgatccaaa cagatcttac actgttccag ctaaatgtgg tactacaacc     2100
gctactgaaa atgacacttg gagatga                                         2127
```

<210> SEQ ID NO 39
<211> LENGTH: 1917
<212> TYPE: DNA
<213> ORGANISM: Artificial Sequence
<220> FEATURE:
<223> OTHER INFORMATION: Encoding SEQ ID NO: 32

<400> SEQUENCE: 39

```
atgagacaag tttggttctc ttggatcgtt ggtttgttct tgtgtttctt caacgtttct       60
tctgctgctc cacaattgtc tccaagagct acttctttgg attcttggtt gtcatctgaa      120
accacctttt ctttgaacgg tatcttggct aatatcggtt cttctggtgc ttactctaaa      180
tctgctgctt caggtgctgt tattgcttct ccatctactt ctaatccaga ctactattac      240
acttggacta gagatgctgc tttgactttg aaagctttgg ttgacatttt ccgtaatggt      300
aacttgggct tgcaaaccgt tattgaacaa tacgttaatg cccaagctaa gttgcaaact      360
gtttcaaatc catctggtgg tttgtctgat ggtgctggtt tgggtgaacc taagtttaat      420
gttgatttgt ctgctttcac tggtgcttgg ggtagaccac aaagagatgg tccagctttg      480
```

```
agagctattg ctttgattga ttttggcaac tggttgatcg ataacggcta caaatcttac    540
gctgttaaca atgtttggcc catcgttaga aatgatttgg cttatgttgc tcagtactgg    600
tcccaatctg gttttgattt gtgggaagaa gtcaactcca tgtcttttt  caccgttgcc    660 aatcaacaca gatcattggt tgaaggttct gcttttgctt ctagagttgg tgcttcttgt    720
tctggttgtg attctcaagc tccacaaatt ttgtgctaca tgcaatcttt ttggaccggc    780
tcttacatta acgctaatac tggtggtggt agatctggta aagattccaa cactattttg    840
gcctccattc atactttga  tccagctgct tcatgtgatg atgttacttt tcaaccatgt    900
tcctctagag ctttggctaa ccataaggtt tacaccgatt ctttcagatc cgtttacgct    960
ttgaattccg gtattgctca aggtaaagct gtttctgttg gtagatatcc agaggattct   1020
tactatggtg gtaatccatg gttcttgtct aatttggctg ctgctgaaca attatacgat   1080
gcaatctacc aatggaacaa gatcggttcc attactatta cctctacctc tttggctttc   1140
ttcaaggatg tttatccatc agctgctact ggtacttatg cttctggttc tactactttc   1200
aacgccatta tttctgctgt taagacttac gctgatggct acgtttctat cgttcaatct   1260
cattcttacg ccaacggttc tttgtccgaa caatttgata gaactaccgg cttgtctatt   1320
tccgctagag atttgacttg gtcttatgca gctttgttga ctgccaatga tagaagaaat   1380
ggtgttgttc ctccttcttg gggtgcttca tctgctaatt ctattccagg ttcatgttct   1440
atgggttctg ctacaggttc ttacgctact ccatcagttg gttcttggcc agctactttg   1500
acttctggta ctgctgctcc atcttctact tcaactacta caaaagctcc aactaccact   1560
actgctacta caactacatc tgctggttca tgtactactc caactgctgt tgctgttact   1620
ttcgacgaaa ttgctactac taccttcggt gaaaacgttt acttggttgg ttccatctct   1680
caattaggta attggaatac tgccaacggt attccattat ccgcttctaa gtacacttct   1740
tctaacccat gtggtacgc  tactgttaat ttgccagctg gtactacttt tcagtacaag   1800
tacttcagaa aagagtccga cggttctatt aagtgggaat ctgatccaaa cagatcttac   1860
actgttccag ctaaatgtgg tactacaacc gctactgaaa atgacacttg gagatga      1917
```

<210> SEQ ID NO 40
<211> LENGTH: 66
<212> TYPE: DNA
<213> ORGANISM: Artificial Sequence
<220> FEATURE:
<223> OTHER INFORMATION: Encoding SEQ ID NO: 23

<400> SEQUENCE: 40

```
atgagacaag tttggttctc ttggatcgtt ggtttgttct tgtgtttctt caacgtttct    60
tctgct                                                              66
```

<210> SEQ ID NO 41
<211> LENGTH: 57
<212> TYPE: DNA
<213> ORGANISM: Artificial Sequence
<220> FEATURE:
<223> OTHER INFORMATION: Encoding SEQ ID NO: 26

<400> SEQUENCE: 41

```
atgaggttcc catctatttt caccgctgtt ttgtttgctg cttcttctgc tttggct       57
```

<210> SEQ ID NO 42
<211> LENGTH: 255
<212> TYPE: DNA

<213> ORGANISM: Artificial Sequence
<220> FEATURE:
<223> OTHER INFORMATION: Encoding SEQ ID NO: 25

<400> SEQUENCE: 42

```
atgaggttcc catctatttt caccgctgtt ttgtttgctg cttcttctgc tttggctgct      60
ccagttaaca ctactactga agatgagact gctcaaattc cagctgaagc tgttattggt     120
tacttggatt tggaaggtga tttcgatgtt gctgttttgc cattctctaa ctctaccaac     180
aatggcttgt tgttcatcaa cactaccatt gcttctattg ccgctaaaga agaaggcgtt     240
tctttggata agagg                                                      255
```

<210> SEQ ID NO 43
<211> LENGTH: 682
<212> TYPE: PRT
<213> ORGANISM: Artificial Sequence
<220> FEATURE:
<223> OTHER INFORMATION: Penicillium oxalicum glucoamylase with wild-
      type amF signal sequence without first level

<400> SEQUENCE: 43

```
Ala Pro Val Asn Thr Thr Thr Glu Asp Glu Thr Ala Gln Ile Pro Ala
1               5                   10                  15

Glu Ala Val Ile Gly Tyr Leu Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Leu Asp
    50                  55                  60

Lys Arg Ala Pro Gln Leu Ser Pro Arg Ala Thr Ser Leu Asp Ser Trp
65                  70                  75                  80

Leu Ser Ser Glu Thr Thr Phe Ser Leu Asn Gly Ile Leu Ala Asn Ile
                85                  90                  95

Gly Ser Ser Gly Ala Tyr Ser Lys Ser Ala Ala Ser Gly Ala Val Ile
            100                 105                 110

Ala Ser Pro Ser Thr Ser Asn Pro Asp Tyr Tyr Tyr Thr Trp Thr Arg
        115                 120                 125

Asp Ala Ala Leu Thr Leu Lys Ala Leu Val Asp Ile Phe Arg Asn Gly
    130                 135                 140

Asn Leu Gly Leu Gln Thr Val Ile Glu Gln Tyr Val Asn Ala Gln Ala
145                 150                 155                 160

Lys Leu Gln Thr Val Ser Asn Pro Ser Gly Gly Leu Ser Asp Gly Ala
                165                 170                 175

Gly Leu Gly Glu Pro Lys Phe Asn Val Asp Leu Ser Ala Phe Thr Gly
            180                 185                 190

Ala Trp Gly Arg Pro Gln Arg Asp Gly Pro Ala Leu Arg Ala Ile Ala
        195                 200                 205

Leu Ile Asp Phe Gly Asn Trp Leu Ile Asp Asn Gly Tyr Lys Ser Tyr
    210                 215                 220

Ala Val Asn Asn Val Trp Pro Ile Val Arg Asn Asp Leu Ala Tyr Val
225                 230                 235                 240

Ala Gln Tyr Trp Ser Gln Ser Gly Phe Asp Leu Trp Glu Glu Val Asn
                245                 250                 255

Ser Met Ser Phe Phe Thr Val Ala Asn Gln His Arg Ser Leu Val Glu
            260                 265                 270

Gly Ser Ala Phe Ala Ser Arg Val Gly Ala Ser Cys Ser Gly Cys Asp
```

```
                275                 280                 285
Ser Gln Ala Pro Gln Ile Leu Cys Tyr Met Gln Ser Phe Trp Thr Gly
290                 295                 300

Ser Tyr Ile Asn Ala Asn Thr Gly Gly Gly Arg Ser Gly Lys Asp Ser
305                 310                 315                 320

Asn Thr Ile Leu Ala Ser Ile His Thr Phe Asp Pro Ala Ala Ser Cys
                325                 330                 335

Asp Asp Val Thr Phe Gln Pro Cys Ser Ser Arg Ala Leu Ala Asn His
                340                 345                 350

Lys Val Tyr Thr Asp Ser Phe Arg Ser Val Tyr Ala Leu Asn Ser Gly
                355                 360                 365

Ile Ala Gln Gly Lys Ala Val Ser Val Gly Arg Tyr Pro Glu Asp Ser
370                 375                 380

Tyr Tyr Gly Gly Asn Pro Trp Phe Leu Ser Asn Leu Ala Ala Ala Glu
385                 390                 395                 400

Gln Leu Tyr Asp Ala Ile Tyr Gln Trp Asn Lys Ile Gly Ser Ile Thr
                405                 410                 415

Ile Thr Ser Thr Ser Leu Ala Phe Phe Lys Asp Val Tyr Pro Ser Ala
                420                 425                 430

Ala Thr Gly Thr Tyr Ala Ser Gly Ser Thr Thr Phe Asn Ala Ile Ile
                435                 440                 445

Ser Ala Val Lys Thr Tyr Ala Asp Gly Tyr Val Ser Ile Val Gln Ser
450                 455                 460

His Ser Tyr Ala Asn Gly Ser Leu Ser Glu Gln Phe Asp Arg Thr Thr
465                 470                 475                 480

Gly Leu Ser Ile Ser Ala Arg Asp Leu Thr Trp Ser Tyr Ala Ala Leu
                485                 490                 495

Leu Thr Ala Asn Asp Arg Arg Asn Gly Val Val Pro Pro Ser Trp Gly
                500                 505                 510

Ala Ser Ser Ala Asn Ser Ile Pro Gly Ser Cys Ser Met Gly Ser Ala
                515                 520                 525

Thr Gly Ser Tyr Ala Thr Pro Ser Val Gly Ser Trp Pro Ala Thr Leu
                530                 535                 540

Thr Ser Gly Thr Ala Ala Pro Ser Ser Thr Ser Thr Thr Thr Lys Ala
545                 550                 555                 560

Pro Thr Thr Thr Thr Ala Thr Thr Thr Ser Ala Gly Ser Cys Thr
                565                 570                 575

Thr Pro Thr Ala Val Ala Val Thr Phe Asp Glu Ile Ala Thr Thr Thr
                580                 585                 590

Phe Gly Glu Asn Val Tyr Leu Val Gly Ser Ile Ser Gln Leu Gly Asn
                595                 600                 605

Trp Asn Thr Ala Asn Gly Ile Pro Leu Ser Ala Ser Lys Tyr Thr Ser
                610                 615                 620

Ser Asn Pro Leu Trp Tyr Ala Thr Val Asn Leu Pro Ala Gly Thr Thr
625                 630                 635                 640

Phe Gln Tyr Lys Tyr Phe Arg Lys Glu Ser Asp Gly Ser Ile Lys Trp
                645                 650                 655

Glu Ser Asp Pro Asn Arg Ser Tyr Thr Val Pro Ala Lys Cys Gly Thr
                660                 665                 670

Thr Thr Ala Thr Glu Asn Asp Thr Trp Arg
                675                 680
```

<210> SEQ ID NO 44

<211> LENGTH: 2049
<212> TYPE: DNA
<213> ORGANISM: Artificial Sequence
<220> FEATURE:
<223> OTHER INFORMATION: Encoding SEQ ID NO: 43

<400> SEQUENCE: 44

| | | | | | |
|---|---|---|---|---|---|
| gctccagtta | acactactac | tgaagatgag | actgctcaaa | ttccagctga | agctgttatt | 60 |
| ggttacttgg | atttggaagg | tgatttcgat | gttgctgttt | tgccattctc | taactctacc | 120 |
| aacaatggct | tgttgttcat | caacactacc | attgcttcta | ttgccgctaa | agaagaaggc | 180 |
| gtttctttgg | ataagagggc | tccacaattg | tctccaagag | ctacttcttt | ggattcttgg | 240 |
| ttgtcatctg | aaaccacctt | tctttgaac | ggtatcttgg | ctaatatcgg | ttcttctggt | 300 |
| gcttactcta | atctgctgc | ttcaggtgct | gttattgctt | ctccatctac | ttctaatcca | 360 |
| gactactatt | acacttggac | tagagatgct | gctttgactt | tgaaagcttt | ggttgacatt | 420 |
| ttccgtaatg | gtaacttggg | cttgcaaacc | gttattgaac | aatacgttaa | tgcccaagct | 480 |
| aagttgcaaa | ctgtttcaaa | tccatctggt | ggtttgtctg | atggtgctgg | tttgggtgaa | 540 |
| cctaagttta | atgttgattt | gtctgctttc | actggtgctt | ggggtagacc | acaaagagat | 600 |
| ggtccagctt | tgagagctat | tgctttgatt | gattttggca | actggttgat | cgataacggc | 660 |
| tacaaatctt | acgctgttaa | caatgtttgg | cccatcgtta | gaaatgattt | ggcttatgtt | 720 |
| gctcagtact | ggtcccaatc | tggttttgat | ttgtgggaag | aagtcaactc | catgtctttt | 780 |
| ttcaccgttg | ccaatcaaca | cagatcattg | gttgaaggtt | ctgcttttgc | ttctagagtt | 840 |
| ggtgcttctt | gttctggttg | tgattctcaa | gctccacaaa | ttttgtgcta | catgcaatct | 900 |
| ttttggaccg | gctcttacat | taacgctaat | actggtggtg | gtagatctgg | taaagattcc | 960 |
| aacactattt | tggcctccat | tcatactttt | gatccagctg | cttcatgtga | tgatgttact | 1020 |
| tttcaaccat | gttcctctag | agctttggct | aaccataagg | tttacaccga | ttctttcaga | 1080 |
| tccgtttacg | ctttgaattc | cggtattgct | caaggtaaag | ctgtttctgt | tggtagatat | 1140 |
| ccagaggatt | cttactatgg | tggtaatcca | tggttcttgt | ctaatttggc | tgctgctgaa | 1200 |
| caattatacg | atgcaatcta | ccaatggaac | aagatcggtt | ccattactat | tacctctacc | 1260 |
| tctttggctt | tcttcaagga | tgtttatcca | tcagctgcta | ctggtactta | tgcttctggt | 1320 |
| tctactactt | tcaacgccat | tatttctgct | gttaagactt | acgctgatgg | ctacgttttct | 1380 |
| atcgttcaat | ctcattctta | cgccaacggt | tctttgtccg | aacaatttga | tagaactacc | 1440 |
| ggcttgtcta | tttccgctag | agatttgact | tggtcttatg | cagctttgtt | gactgccaat | 1500 |
| gatagaagaa | atggtgttgt | tcctccttct | tggggtgctt | catctgctaa | ttctattcca | 1560 |
| ggttcatgtt | ctatgggttc | tgctacaggt | tcttacgcta | ctccatcagt | tggttcttgg | 1620 |
| ccagctactt | tgacttctgg | tactgctgct | ccatcttcta | cttcaactac | tacaaaagct | 1680 |
| ccaactacca | ctactgctac | tacaactaca | tctgctggtt | catgtactac | tccaactgct | 1740 |
| gttgctgtta | ctttcgacga | aattgctact | actaccttcg | gtgaaaacgt | ttacttggtt | 1800 |
| ggttccatct | ctcaattagg | taattggaat | actgccaacg | tattccatt | atccgcttct | 1860 |
| aagtacactt | cttctaaccc | attgtggtac | gctactgtta | atttgccagc | tggtactact | 1920 |
| tttcagtaca | agtacttcag | aaaagagtcc | gacggttcta | ttaagtggga | atctgatcca | 1980 |
| aacagatctt | acactgttcc | agctaaatgt | ggtactacaa | ccgctactga | aaatgacact | 2040 |
| tggagatga | | | | | | 2049 |

<210> SEQ ID NO 45
<211> LENGTH: 705
<212> TYPE: PRT
<213> ORGANISM: Artificial Sequence
<220> FEATURE:
<223> OTHER INFORMATION: Penicillium oxalicum glucoamylase with mutant amF signal sequence with first level signal sequence

<400> SEQUENCE: 45

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Pro Gln Leu Ser Pro Arg
                85                  90                  95

Ala Thr Ser Leu Asp Ser Trp Leu Ser Ser Glu Thr Thr Phe Ser Leu
            100                 105                 110

Asn Gly Ile Leu Ala Asn Ile Gly Ser Ser Gly Ala Tyr Ser Lys Ser
        115                 120                 125

Ala Ala Ser Gly Ala Val Ile Ala Ser Pro Ser Thr Ser Asn Pro Asp
    130                 135                 140

Tyr Tyr Tyr Thr Trp Thr Arg Asp Ala Ala Leu Thr Leu Lys Ala Leu
145                 150                 155                 160

Val Asp Ile Phe Arg Asn Gly Asn Leu Gly Leu Gln Thr Val Ile Glu
                165                 170                 175

Gln Tyr Val Asn Ala Gln Ala Lys Leu Gln Thr Val Ser Asn Pro Ser
            180                 185                 190

Gly Gly Leu Ser Asp Gly Ala Gly Leu Gly Glu Pro Lys Phe Asn Val
        195                 200                 205

Asp Leu Ser Ala Phe Thr Gly Ala Trp Gly Arg Pro Gln Arg Asp Gly
    210                 215                 220

Pro Ala Leu Arg Ala Ile Ala Leu Ile Asp Phe Gly Asn Trp Leu Ile
225                 230                 235                 240

Asp Asn Gly Tyr Lys Ser Tyr Ala Val Asn Asn Val Trp Pro Ile Val
                245                 250                 255

Arg Asn Asp Leu Ala Tyr Val Ala Gln Tyr Trp Ser Gln Ser Gly Phe
            260                 265                 270

Asp Leu Trp Glu Glu Val Asn Ser Met Ser Phe Phe Thr Val Ala Asn
        275                 280                 285

Gln His Arg Ser Leu Val Glu Gly Ser Ala Phe Ala Ser Arg Val Gly
    290                 295                 300

Ala Ser Cys Ser Gly Cys Asp Ser Gln Ala Pro Gln Ile Leu Cys Tyr
305                 310                 315                 320

Met Gln Ser Phe Trp Thr Gly Ser Tyr Ile Asn Ala Asn Thr Gly Gly
                325                 330                 335

Gly Arg Ser Gly Lys Asp Ser Asn Thr Ile Leu Ala Ser Ile His Thr
            340                 345                 350

Phe Asp Pro Ala Ala Ser Cys Asp Asp Val Thr Phe Gln Pro Cys Ser
        355                 360                 365
```

| Ser | Arg | Ala | Leu | Ala | Asn | His | Lys | Val | Tyr | Thr | Asp | Ser | Phe | Arg | Ser |
| --- | --- | --- | --- | --- | --- | --- | --- | --- | --- | --- | --- | --- | --- | --- | --- |
| 370 | | | | | 375 | | | | | 380 | | | | | |

| Val | Tyr | Ala | Leu | Asn | Ser | Gly | Ile | Ala | Gln | Gly | Lys | Ala | Val | Ser | Val |
| --- | --- | --- | --- | --- | --- | --- | --- | --- | --- | --- | --- | --- | --- | --- | --- |
| 385 | | | | | 390 | | | | | 395 | | | | | 400 |

| Gly | Arg | Tyr | Pro | Glu | Asp | Ser | Tyr | Tyr | Gly | Gly | Asn | Pro | Trp | Phe | Leu |
| --- | --- | --- | --- | --- | --- | --- | --- | --- | --- | --- | --- | --- | --- | --- | --- |
| | | | | 405 | | | | | 410 | | | | | 415 | |

| Ser | Asn | Leu | Ala | Ala | Ala | Glu | Gln | Leu | Tyr | Asp | Ala | Ile | Tyr | Gln | Trp |
| --- | --- | --- | --- | --- | --- | --- | --- | --- | --- | --- | --- | --- | --- | --- | --- |
| | | | 420 | | | | | 425 | | | | | 430 | | |

| Asn | Lys | Ile | Gly | Ser | Ile | Thr | Ile | Ser | Thr | Ser | Leu | Ala | Phe | Phe |
| --- | --- | --- | --- | --- | --- | --- | --- | --- | --- | --- | --- | --- | --- | --- |
| | | 435 | | | | | 440 | | | | | 445 | | |

| Lys | Asp | Val | Tyr | Pro | Ser | Ala | Ala | Thr | Gly | Thr | Tyr | Ala | Ser | Gly | Ser |
| --- | --- | --- | --- | --- | --- | --- | --- | --- | --- | --- | --- | --- | --- | --- | --- |
| | 450 | | | | | 455 | | | | | 460 | | | | |

| Thr | Thr | Phe | Asn | Ala | Ile | Ile | Ser | Ala | Val | Lys | Thr | Tyr | Ala | Asp | Gly |
| --- | --- | --- | --- | --- | --- | --- | --- | --- | --- | --- | --- | --- | --- | --- | --- |
| 465 | | | | | 470 | | | | | 475 | | | | | 480 |

| Tyr | Val | Ser | Ile | Val | Gln | Ser | His | Ser | Tyr | Ala | Asn | Gly | Ser | Leu | Ser |
| --- | --- | --- | --- | --- | --- | --- | --- | --- | --- | --- | --- | --- | --- | --- | --- |
| | | | | 485 | | | | | 490 | | | | | 495 | |

| Glu | Gln | Phe | Asp | Arg | Thr | Thr | Gly | Leu | Ser | Ile | Ser | Ala | Arg | Asp | Leu |
| --- | --- | --- | --- | --- | --- | --- | --- | --- | --- | --- | --- | --- | --- | --- | --- |
| | | | | 500 | | | | | 505 | | | | | 510 | |

| Thr | Trp | Ser | Tyr | Ala | Ala | Leu | Leu | Thr | Ala | Asn | Asp | Arg | Arg | Asn | Gly |
| --- | --- | --- | --- | --- | --- | --- | --- | --- | --- | --- | --- | --- | --- | --- | --- |
| | | 515 | | | | | 520 | | | | | 525 | | | |

| Val | Val | Pro | Pro | Ser | Trp | Gly | Ala | Ser | Ser | Ala | Asn | Ser | Ile | Pro | Gly |
| --- | --- | --- | --- | --- | --- | --- | --- | --- | --- | --- | --- | --- | --- | --- | --- |
| | 530 | | | | | 535 | | | | | 540 | | | | |

| Ser | Cys | Ser | Met | Gly | Ser | Ala | Thr | Gly | Ser | Tyr | Ala | Thr | Pro | Ser | Val |
| --- | --- | --- | --- | --- | --- | --- | --- | --- | --- | --- | --- | --- | --- | --- | --- |
| 545 | | | | | 550 | | | | | 555 | | | | | 560 |

| Gly | Ser | Trp | Pro | Ala | Thr | Leu | Thr | Ser | Gly | Thr | Ala | Ala | Pro | Ser | Ser |
| --- | --- | --- | --- | --- | --- | --- | --- | --- | --- | --- | --- | --- | --- | --- | --- |
| | | | | 565 | | | | | 570 | | | | | 575 | |

| Thr | Ser | Thr | Thr | Thr | Lys | Ala | Pro | Thr | Thr | Thr | Thr | Ala | Thr | Thr | Thr |
| --- | --- | --- | --- | --- | --- | --- | --- | --- | --- | --- | --- | --- | --- | --- | --- |
| | | | 580 | | | | | 585 | | | | | 590 | | |

| Thr | Ser | Ala | Gly | Ser | Cys | Thr | Thr | Pro | Thr | Ala | Val | Ala | Val | Thr | Phe |
| --- | --- | --- | --- | --- | --- | --- | --- | --- | --- | --- | --- | --- | --- | --- | --- |
| | | 595 | | | | | 600 | | | | | 605 | | | |

| Asp | Glu | Ile | Ala | Thr | Thr | Thr | Phe | Gly | Glu | Asn | Val | Tyr | Leu | Val | Gly |
| --- | --- | --- | --- | --- | --- | --- | --- | --- | --- | --- | --- | --- | --- | --- | --- |
| | 610 | | | | | 615 | | | | | 620 | | | | |

| Ser | Ile | Ser | Gln | Leu | Gly | Asn | Trp | Asn | Thr | Ala | Asn | Gly | Ile | Pro | Leu |
| --- | --- | --- | --- | --- | --- | --- | --- | --- | --- | --- | --- | --- | --- | --- | --- |
| 625 | | | | | 630 | | | | | 635 | | | | | 640 |

| Ser | Ala | Ser | Lys | Tyr | Thr | Ser | Ser | Asn | Pro | Leu | Trp | Tyr | Ala | Thr | Val |
| --- | --- | --- | --- | --- | --- | --- | --- | --- | --- | --- | --- | --- | --- | --- | --- |
| | | | | 645 | | | | | 650 | | | | | 655 | |

| Asn | Leu | Pro | Ala | Gly | Thr | Thr | Phe | Gln | Tyr | Lys | Tyr | Phe | Arg | Lys | Glu |
| --- | --- | --- | --- | --- | --- | --- | --- | --- | --- | --- | --- | --- | --- | --- | --- |
| | | | 660 | | | | | 665 | | | | | 670 | | |

| Ser | Asp | Gly | Ser | Ile | Lys | Trp | Glu | Ser | Asp | Pro | Asn | Arg | Ser | Tyr | Thr |
| --- | --- | --- | --- | --- | --- | --- | --- | --- | --- | --- | --- | --- | --- | --- | --- |
| | 675 | | | | | 680 | | | | | 685 | | | | |

| Val | Pro | Ala | Lys | Cys | Gly | Thr | Thr | Thr | Ala | Thr | Glu | Asn | Asp | Thr | Trp |
| --- | --- | --- | --- | --- | --- | --- | --- | --- | --- | --- | --- | --- | --- | --- | --- |
| 690 | | | | | 695 | | | | | 700 | | | | | |

| Arg |
| --- |
| 705 |

<210> SEQ ID NO 46
<211> LENGTH: 1851
<212> TYPE: DNA
<213> ORGANISM: Artificial Sequence
<220> FEATURE:
<223> OTHER INFORMATION: Encoding SEQ ID NO: 45

<400> SEQUENCE: 46

| gctccacaat tgtctccaag agctacttct ttggattctt ggttgtcatc tgaaaccacc | 60 |
| --- | --- |
| ttttctttga acggtatctt ggctaatatc ggttcttctg gtgcttactc taaatctgct | 120 |

```
gcttcaggtg ctgttattgc ttctccatct acttctaatc cagactacta ttacacttgg    180
actagagatg ctgctttgac tttgaaagct ttggttgaca ttttccgtaa tggtaacttg    240
ggcttgcaaa ccgttattga acaatacgtt aatgcccaag ctaagttgca aactgtttca    300
aatccatctg gtggtttgtc tgatggtgct ggtttgggtg aacctaagtt taatgttgat    360
ttgtctgctt tcactggtgc ttggggtaga ccacaaagag atggtccagc tttgagagct    420
attgctttga ttgattttgg caactggttg atcgataacg ctacaaatc ttacgctgtt     480 aacaatgttt ggcccatcgt tagaaatgat ttggcttatg ttgctcagta ctggtcccaa    540
tctggttttg atttgtggga agaagtcaac tccatgtctt ttttcaccgt tgccaatcaa    600
cacagatcat ggttgaagg ttctgctttt gcttctagag ttggtgcttc ttgttctggt     660
tgtgattctc aagctccaca aattttgtgc tacatgcaat ctttttggac cggctcttac    720
attaacgcta atactggtgg tgtagatct ggtaaagatt ccaacactat tttggcctcc     780
attcatactt ttgatccagc tgcttcatgt gatgatgtta cttttcaacc atgttcctct    840
agagctttgg ctaaccataa ggtttacacc gattctttca gatccgttta cgctttgaat    900
tccggtattg ctcaaggtaa agctgtttct gttggtagat atccagagga ttcttactat    960
ggtggtaatc catggttctt gtctaatttg ctgctgctg aacaattata cgatgcaatc    1020
taccaatgga acaagatcgg ttccattact attacctcta cctctttggc tttcttcaag   1080
gatgtttatc catcagctgc tactggtact tatgcttctg gttctactac tttcaacgcc   1140
attatttctg ctgttaagac ttacgctgat ggctacgttt ctatcgttca atctcattct   1200
tacgccaacg gttctttgtc cgaacaattt gatagaacta ccggcttgtc tatttccgct   1260
agagatttga cttggtctta tgcagctttg ttgactgcca atgatagaag aaatggtgtt   1320
gttcctcctt cttggggtgc ttcatctgct aattctattc caggttcatg ttctatgggt   1380
tctgctacag gttcttacgc tactccatca gttggttctt ggccagctac tttgacttct   1440
ggtactgctg ctccatcttc tacttcaact actacaaaag ctccaactac cactactgct   1500
actacaacta catctgctgg ttcatgtact actccaactg ctgttgctgt tactttcgac   1560
gaaattgcta ctactacctt cggtgaaaac gtttacttgg ttggttccat ctctcaatta   1620
ggtaattgga atactgccaa cggtattcca ttatccgctt ctaagtacac ttcttctaac   1680
ccattgtggt acgctactgt taatttgcca gctggtacta cttttcagta caagtacttc   1740
agaaaagagt ccgacggttc tattaagtgg gaatctgatc caaacagatc ttacactgtt   1800
ccagctaaat gtggtactac aaccgctact gaaaatgaca cttggagatg a             1851
```

<210> SEQ ID NO 47
<211> LENGTH: 89
<212> TYPE: PRT
<213> ORGANISM: Artificial Sequence
<220> FEATURE:
<223> OTHER INFORMATION: Mutated aMF signal sequence with first level
      signal sequence

<400> SEQUENCE: 47

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

```
Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala
                 85
```

```
<210> SEQ ID NO 48
<211> LENGTH: 267
<212> TYPE: DNA
<213> ORGANISM: Artificial Sequence
<220> FEATURE:
<223> OTHER INFORMATION: Encoding SEQ ID NO: 47

<400> SEQUENCE: 48
atgaggttcc catctatttt caccgctgtt ttgtttgctg cttcttctgc tttggctgct      60
ccagttaaca ctactactga agacgaaact gctcaaatcc agctgaagc tgttatcggt     120 tactctgact tggaaggtga cttcgacgtt gctgttttgc cattctctaa ctctactaac    180
aacggtttgt tgttcatcaa cactactatc gcttctatcg ctgctaagga agaaggtgtt    240
tctttggaaa agagagaagc tgaagct                                         267
```

```
<210> SEQ ID NO 49
<211> LENGTH: 686
<212> TYPE: PRT
<213> ORGANISM: Artificial Sequence
<220> FEATURE:
<223> OTHER INFORMATION: Penicillum oxalicum glucoamylse with mutated
      aMF signal sequence without first level signal sequence

<400> SEQUENCE: 49

Ala Pro Val Asn Thr Thr Thr Glu Asp Glu Thr Ala Gln Ile Pro Ala
 1               5                  10                  15

Glu Ala Val Ile Gly Tyr Ser Asp Leu Glu Gly Asp Phe Asp Val Ala
                 20                  25                  30

Val Leu Pro Phe Ser Asn Ser Thr Asn Asn Gly Leu Leu Phe Ile Asn
             35                  40                  45

Thr Thr Ile Ala Ser Ile Ala Ala Lys Glu Glu Gly Val Ser Leu Glu
 50                  55                  60

Lys Arg Glu Ala Glu Ala Ala Pro Gln Leu Ser Pro Arg Ala Thr Ser
 65                  70                  75                  80

Leu Asp Ser Trp Leu Ser Ser Glu Thr Thr Phe Ser Leu Asn Gly Ile
                 85                  90                  95

Leu Ala Asn Ile Gly Ser Ser Gly Ala Tyr Ser Lys Ser Ala Ala Ser
                100                 105                 110

Gly Ala Val Ile Ala Ser Pro Ser Thr Ser Asn Pro Asp Tyr Tyr Tyr
            115                 120                 125

Thr Trp Thr Arg Asp Ala Ala Leu Thr Leu Lys Ala Leu Val Asp Ile
    130                 135                 140

Phe Arg Asn Gly Asn Leu Gly Leu Gln Thr Val Ile Glu Gln Tyr Val
145                 150                 155                 160

Asn Ala Gln Ala Lys Leu Gln Thr Val Ser Asn Pro Ser Gly Gly Leu
                165                 170                 175

Ser Asp Gly Ala Gly Leu Gly Glu Pro Lys Phe Asn Val Asp Leu Ser
            180                 185                 190

Ala Phe Thr Gly Ala Trp Gly Arg Pro Gln Arg Asp Gly Pro Ala Leu
        195                 200                 205
```

```
Arg Ala Ile Ala Leu Ile Asp Phe Gly Asn Trp Leu Ile Asp Asn Gly
    210                 215                 220

Tyr Lys Ser Tyr Ala Val Asn Asn Val Trp Pro Ile Val Arg Asn Asp
225                 230                 235                 240

Leu Ala Tyr Val Ala Gln Tyr Trp Ser Gln Ser Gly Phe Asp Leu Trp
                245                 250                 255

Glu Glu Val Asn Ser Met Ser Phe Phe Thr Val Ala Asn Gln His Arg
                260                 265                 270

Ser Leu Val Glu Gly Ser Ala Phe Ala Ser Arg Val Gly Ala Ser Cys
            275                 280                 285

Ser Gly Cys Asp Ser Gln Ala Pro Gln Ile Leu Cys Tyr Met Gln Ser
        290                 295                 300

Phe Trp Thr Gly Ser Tyr Ile Asn Ala Asn Thr Gly Gly Arg Ser
305                 310                 315                 320

Gly Lys Asp Ser Asn Thr Ile Leu Ala Ser Ile His Thr Phe Asp Pro
                325                 330                 335

Ala Ala Ser Cys Asp Asp Val Thr Phe Gln Pro Cys Ser Ser Arg Ala
                340                 345                 350

Leu Ala Asn His Lys Val Tyr Thr Asp Ser Phe Arg Ser Val Tyr Ala
            355                 360                 365

Leu Asn Ser Gly Ile Ala Gln Gly Lys Ala Val Ser Val Gly Arg Tyr
        370                 375                 380

Pro Glu Asp Ser Tyr Tyr Gly Gly Asn Pro Trp Phe Leu Ser Asn Leu
385                 390                 395                 400

Ala Ala Ala Glu Gln Leu Tyr Asp Ala Ile Tyr Gln Trp Asn Lys Ile
                405                 410                 415

Gly Ser Ile Thr Ile Thr Ser Thr Ser Leu Ala Phe Phe Lys Asp Val
            420                 425                 430

Tyr Pro Ser Ala Ala Thr Gly Thr Tyr Ala Ser Gly Ser Thr Thr Phe
        435                 440                 445

Asn Ala Ile Ile Ser Ala Val Lys Thr Tyr Ala Asp Gly Tyr Val Ser
    450                 455                 460

Ile Val Gln Ser His Ser Tyr Ala Asn Gly Ser Leu Ser Glu Gln Phe
465                 470                 475                 480

Asp Arg Thr Thr Gly Leu Ser Ile Ser Ala Arg Asp Leu Thr Trp Ser
                485                 490                 495

Tyr Ala Ala Leu Leu Thr Ala Asn Asp Arg Arg Asn Gly Val Val Pro
                500                 505                 510

Pro Ser Trp Gly Ala Ser Ser Ala Asn Ser Ile Pro Gly Ser Cys Ser
            515                 520                 525

Met Gly Ser Ala Thr Gly Ser Tyr Ala Thr Pro Ser Val Gly Ser Trp
        530                 535                 540

Pro Ala Thr Leu Thr Ser Gly Thr Ala Ala Pro Ser Ser Thr Ser Thr
545                 550                 555                 560

Thr Thr Lys Ala Pro Thr Thr Thr Thr Ala Thr Thr Thr Ser Ala
                565                 570                 575

Gly Ser Cys Thr Thr Pro Thr Ala Val Ala Val Thr Phe Asp Glu Ile
            580                 585                 590

Ala Thr Thr Thr Phe Gly Glu Asn Val Tyr Leu Val Gly Ser Ile Ser
        595                 600                 605

Gln Leu Gly Asn Trp Asn Thr Ala Asn Gly Ile Pro Leu Ser Ala Ser
    610                 615                 620

Lys Tyr Thr Ser Ser Asn Pro Leu Trp Tyr Ala Thr Val Asn Leu Pro
```

```
                625                 630                 635                 640
    Ala Gly Thr Thr Phe Gln Tyr Lys Tyr Phe Arg Lys Glu Ser Asp Gly
                    645                 650                 655

Ser Ile Lys Trp Glu Ser Asp Pro Asn Arg Ser Tyr Thr Val Pro Ala
                660                 665                 670

Lys Cys Gly Thr Thr Ala Thr Glu Asn Asp Thr Trp Arg
                    675                 680                 685

<210> SEQ ID NO 50
<211> LENGTH: 2061
<212> TYPE: DNA
<213> ORGANISM: Artificial Sequence
<220> FEATURE:
<223> OTHER INFORMATION: Encoding SEQ ID NO: 49

<400> SEQUENCE: 50
gctccagtta acactactac tgaagacgaa actgctcaaa tcccagctga agctgttatc      60
ggttactctg acttggaagg tgacttcgac gttgctgttt tgccattctc taactctact     120
aacaacggtt tgttgttcat caacactact atcgcttcta tcgctgctaa ggaagaaggt     180
gtttctttgg aaaagagaga agctgaagct gctccacaat tgtctccaag agctacttct     240
ttggattctt ggttgtcatc tgaaaccacc ttttctttga acggtatctt ggctaatatc     300
ggttcttctg tgcttactc taaatctgct gcttcaggtg ctgttattgc ttctccatct     360
acttctaatc cagactacta ttacacttgg actagagatg ctgctttgac tttgaaagct     420
ttggttgaca ttttccgtaa tggtaacttg ggcttgcaaa ccgttattga acaaatacgtt    480 aatgcccaag ctaagttgca aactgtttca atccatctg gtggtttgtc tgatggtgct     540
ggtttgggtg aacctaagtt taatgttgat tgtctgctt tcactggtgc ttggggtaga     600
ccacaaagag atggtccagc tttgagagct attgctttga ttgattttgg caactggttg     660
atcgataacg ctacaaatc ttacgctgtt aacaatgttt ggcccatcgt tagaaatgat     720
ttggcttatg ttgctcagta ctggtcccaa tctggttttg atttgtggga agaagtcaac     780
tccatgtctt tttcaccgt tgccaatcaa cacagatcat tggttgaagg ttctgctttt     840
gcttctagag ttggtgcttc ttgttctggt tgtgattctc aagctccaca aattttgtgc     900
tacatgcaat cttttggac cggctcttac attaacgcta atactggtgg tggtagatct     960
ggtaaagatt ccaacactat tttggcctcc attcatactt ttgatccagc tgcttcatgt    1020
gatgatgtta cttttcaacc atgttcctct agagctttgg ctaaccataa ggtttacacc    1080
gattctttca gatccgttta cgctttgaat tccggtattg ctcaaggtaa agctgtttct    1140
gttggtagat atccagagga ttcttactat ggtggtaatc catggttctt gtctaatttg    1200
gctgctgctg aacaattata cgatgcaatc taccaatgga acaagatcgg ttccattact    1260
attacctcta cctctttggc tttcttcaag gatgtttatc catcagctgc tactggtact    1320
tatgcttctg gttctactac tttcaacgcc attatttctg ctgttaagac ttacgctgat    1380
ggctacgttt ctatcgttca atctcattct tacgccaacg ttctttgtc cgaacaattt    1440 gatagaacta ccggcttgtc tatttccgct agagatttga cttggtctta tgcagctttg    1500
ttgactgcca atgatagaag aaatggtgtt gttcctcctt cttggggtgc ttcatctgct    1560
aattctattc aggttcatg ttctatgggt tctgctacag gttcttacgc tactccatca    1620
gttggttctt ggccagctac tttgacttct ggtactgctg ctccatcttc tacttcaact    1680
actacaaaag ctccaactac cactactgct actacaacta catctgctgg ttcatgtact    1740
```

```
actccaactg ctgttgctgt tactttcgac gaaattgcta ctactacctt cggtgaaaac    1800
gtttacttgg ttggttccat ctctcaatta ggtaattgga atactgccaa cggtattcca    1860
ttatccgctt ctaagtacac ttcttctaac ccattgtggt acgctactgt taatttgcca    1920
gctggtacta cttttcagta caagtacttc agaaaagagt ccgacggttc tattaagtgg    1980
gaatctgatc caaacagatc ttacactgtt ccagctaaat gtggtactac aaccgctact    2040
gaaaatgaca cttggagatg a                                              2061

<210> SEQ ID NO 51
<211> LENGTH: 210
<212> TYPE: DNA
<213> ORGANISM: Artificial Sequence
<220> FEATURE:
<223> OTHER INFORMATION: Encoding SEQ ID NO: 24

<400> SEQUENCE: 51
gctccagtta acactactac tgaagacgaa actgctcaaa tcccagctga agctgttatc     60
ggttactctg acttggaagg tgacttcgac gttgctgttt tgccattctc taactctact    120
aacaacggtt tgttgttcat caacactact atcgcttcta tcgctgctaa ggaagaaggt    180
gtttctttgg aaaagagaga agctgaagct                                     210

<210> SEQ ID NO 52
<211> LENGTH: 499
<212> TYPE: DNA
<213> ORGANISM: Saccharomyces cerevisiae

<400> SEQUENCE: 52
gggcgccata accaaggtat ctatagaccg ccaatcagca aactacctcc gtacattcct     60
gttgcaccca cacatttata cacccagacc gcgacaaatt acccataagg ttgtttgtga    120
cggcgtcgta caagagaacg tgggaacttt ttaggctcac caaaaaagaa aggaaaaata    180
cgagttgctg acagaagcct caagaaaaaa aaaattcttc ttcgactatg ctggagccag    240
agatgatcga gccggtagtt aactatatat agctaaattg gttccatcac cttcttttct    300
ggtgtcgctc cttctagtgc tatttctggc ttttcctatt ttttttttc cattttctt     360 tctctctttc taatatataa attctcttgc attttctatt tttctctcta tctattctac    420
ttgtttattc ccttcaaggt ttttttttaag gactacttgt ttttagaata tacggtcaac    480
gaactataat taactaaac                                                499

<210> SEQ ID NO 53
<211> LENGTH: 749
<212> TYPE: DNA
<213> ORGANISM: Saccharomyces cerevisiae

<400> SEQUENCE: 53 cgatttttt ctaaaccgtg gaatatttcg gatatccttt tgttgtttcc gggtgtacaa      60
tatggacttc ctcttttctg gcaaccaaac ccatacatcg ggattcctat aataccttcg    120
ttggtctccc taacatgtag gtggcggagg ggagatatac aatagaacag ataccagaca    180
agacataatg ggctaaacaa gactacacca attacactgc ctcattgatg gtggtacata    240
acgaactaat actgtagccc tagacttgat agccatcatc atatcgaagt tcactaccc     300 tttttccatt tgccatctat tgaagtaata ataggcgcat gcaacttctt ttcttttttt    360
ttcttttctc tctcccccgt tgttgtctca ccatatccgc aatgacaaaa aaatgatgga    420
agacactaaa ggaaaaaatt aacgacaaag acagcaccaa cagatgtcgt tgttccagag    480
```

| | |
|---|---|
| ctgatgaggg gtatctcgaa gcacacgaaa cttttccctt ccttcattca cgcacactac | 540 |
| tctctaatga gcaacggtat acggccttcc ttccagttac ttgaatttga aataaaaaaa | 600 |
| gtttgctgtc ttgctatcaa gtataaatag acctgcaatt attaatcttt tgtttcctcg | 660 |
| tcattgttct cgttcccttt cttccttgtt tcttttctg cacaatattt caagctatac | 720 |
| caagcataca atcaactatc tcatataca | 749 |

<210> SEQ ID NO 54
<211> LENGTH: 750
<212> TYPE: DNA
<213> ORGANISM: Saccharomyces cerevisiae

<400> SEQUENCE: 54

| | |
|---|---|
| agtaatagta gtccgtattt gaacaagcgc aaaggtaaac ccgggccgga ttcggccact | 60 |
| tcgctgttcg aattgcccga cagcgttatc ccaactccga aaccgaaacc gaaaccaaag | 120 |
| caatatccga aagttattct gccgtcgaac agcacaagac gcgtatcacc ggtcacggcc | 180 |
| aagaccagca gcagcgcaga aggcgtggtc gtagcaagtg agtctcctgt aatcgcgccg | 240 |
| cacggatcga cccattcgcg gtcgctgagt aagcgacggt catcgggcgc gctcgtggac | 300 |
| gatgacaagc gcgaatcaca caagcatgca gagcaagcac ggcgtaatcg attagcggtc | 360 |
| gcgctgcacg aactggtgtc tttaatcccc gcggagtgga acagcaaaa tgtgtcggcc | 420 |
| gcgccgtcca aagcgaccac cgtggaggcg gcctgccggt acatccgtca cctacagcag | 480 |
| aacgggagca cgtgaccgtg caccaatggg aagcacgctt ccgggcatat cggactgggg | 540 |
| cgcgcctccc ctgcgcggtg cttgttataa gaggcgcttt gctggaaagt ggcccacacc | 600 |
| gggttttcga gattaggacc tacctactca gtcttaaggg cagtattggt tggcgcttat | 660 |
| ttgcacatat tgtatacacg cactcacatt aacagaagca cacatataca cttacaccta | 720 |
| cacacacgga taagaaaaa gaaatagaaa | 750 |

<210> SEQ ID NO 55
<211> LENGTH: 198
<212> TYPE: DNA
<213> ORGANISM: Artificial Sequence
<220> FEATURE:
<223> OTHER INFORMATION: Encoding SEQ ID NO: 27

<400> SEQUENCE: 55

| | |
|---|---|
| gctccagtta acactactac tgaagatgag actgctcaaa ttccagctga agctgttatt | 60 |
| ggttacttgg atttggaagg tgatttcgat gttgctgttt tgccattctc taactctacc | 120 |
| aacaatggct tgttgttcat caacactacc attgcttcta ttgccgctaa agaagaaggc | 180 |
| gtttctttgg ataagagg | 198 |

<210> SEQ ID NO 56
<211> LENGTH: 2106
<212> TYPE: DNA
<213> ORGANISM: Artificial Sequence
<220> FEATURE:
<223> OTHER INFORMATION: Encoding SEQ ID NO: 31

<400> SEQUENCE: 56

| | |
|---|---|
| atgaggttcc catctatttt caccgctgtt ttgtttgctg cttcttctgc tttggctgct | 60 |
| ccagttaaca ctactactga agatgagact gctcaaattc cagctgaagc tgttattggt | 120 |
| tacttggatt tggaaggtga tttcgatgtt gctgttttgc cattctctaa ctctaccaac | 180 |

-continued

```
aatggcttgt tgttcatcaa cactaccatt gcttctattg ccgctaaaga agaaggcgtt    240
tctttggata agagggctcc acaattgtct ccaagagcta cttctttgga ttcttggttg    300
tcatctgaaa ccacctttc tttgaacggt atcttggcta atatcggttc ttctggtgct    360
tactctaaat ctgctgcttc aggtgctgtt attgcttctc catctacttc taatccagac    420
tactattaca cttggactag agatgctgct ttgactttga aagctttggt tgacattttc    480
cgtaatggta acttgggctt gcaaaccgtt attgaacaat acgttaatgc ccaagctaag    540
ttgcaaactg tttcaaatcc atctggtggt ttgtctgatg gtgctggttt gggtgaacct    600
aagtttaatg ttgatttgtc tgctttcact ggtgcttggg gtagaccaca aagagatggt    660
ccagctttga gagctattgc tttgattgat tttggcaact ggttgatcga taacggctac    720
aaatcttacg ctgttaacaa tgtttggccc atcgttagaa atgatttggc ttatgttgct    780
cagtactggt cccaatctgg ttttgatttg tgggaagaag tcaactccat gtcttttttc    840
accgttgcca atcaacacag atcattggtt gaaggttctg cttttgcttc tagagttggt    900
gcttcttgtt ctggttgtga ttctcaagct ccacaaattt tgtgctacat gcaatctttt    960
tggaccggct cttacattaa cgctaatact ggtggtggta gatctggtaa agattccaac   1020
actatttgg cctccattca tactttgat ccagctgctt catgtgatga tgttactttt   1080
caaccatgtt cctctagagc tttggctaac cataaggttt acaccgattc tttcagatcc   1140
gtttacgctt tgaattccgg tattgctcaa ggtaaagctg tttctgttgg tagatatcca   1200
gaggattctt actatggtgg taatccatgg ttcttgtcta atttggctgc tgctgaacaa   1260
ttatacgatg caatctacca atggaacaag atcggttcca ttactattac ctctacctct   1320
ttggctttct tcaaggatgt ttatccatca gctgctactg gtacttatgc ttctggttct   1380
actactttca acgccattat ttctgctgtt aagacttacg ctgatggcta cgtttctatc   1440
gttcaatctc attcttacgc caacggttct ttgtccgaac aatttgatag aactaccggc   1500
ttgtctattt ccgctagaga tttgacttgg tcttatgcag ctttgttgac tgccaatgat   1560
agaagaaatg gtgttgttcc tccttcttgg ggtgcttcat ctgctaattc tattccaggt   1620
tcatgttcta tgggttctgc tacaggttct tacgctactc catcagttgg ttcttggcca   1680
gctactttga cttctggtac tgctgctcca tcttctactt caactactac aaaagctcca   1740
actaccacta ctgctactac aactacatct gctggttcat gtactactcc aactgctgtt   1800
gctgttactt tcgacgaaat tgctactact accttcggtg aaaacgttta cttggttggt   1860
tccatctctc aattaggtaa ttggaatact gccaacggta ttccattatc cgcttctaag   1920
tacacttctt ctaacccatt gtggtacgct actgttaatt tgccagctgg tactactttt   1980
cagtacaagt acttcagaaa agagtccgac ggttctatta agtgggaatc tgatccaaac   2040
agatcttaca ctgttccagc taaatgtggt actacaaccg ctactgaaaa tgacacttgg   2100
agatga                                                             2106
```